US010123978B2

(12) United States Patent
Kawahara et al.

(10) Patent No.: US 10,123,978 B2
(45) Date of Patent: Nov. 13, 2018

(54) PATCH FOR TREATING DERMATOPHYTOSIS

(71) Applicants: MEIJI SEIKA PHARMA CO., LTD., Chuo-ku, Tokyo (JP); NICHIBAN COMPANY LIMITED, Bunkyo-ku, Tokyo (JP)

(72) Inventors: Koji Kawahara, Tokyo (JP); Noriko Kan, Tokyo (JP); Shihoko Watanabe, Tokyo (JP); Kyohei Matsuo, Tokyo (JP)

(73) Assignees: MEIJI SEIKA PHARMA CO., LTD., Tokyo (JP); NICHIBAN COMPANY LIMITED, Tokyo (JP)

( * ) Notice: Subject to any disclaimer, the term of this patent is extended or adjusted under 35 U.S.C. 154(b) by 0 days.

(21) Appl. No.: 15/865,650

(22) Filed: Jan. 9, 2018

(65) Prior Publication Data

US 2018/0200199 A1    Jul. 19, 2018

Related U.S. Application Data

(63) Continuation of application No. 14/418,804, filed as application No. PCT/JP2013/070527 on Jul. 30, 2013, now abandoned.

(30) Foreign Application Priority Data

Jul. 30, 2012 (WO) ................. PCT/JP2012/069285

(51) Int. Cl.
*A61K 9/70* (2006.01)
*A61K 31/415* (2006.01)

(52) U.S. Cl.
CPC .......... *A61K 9/7061* (2013.01); *A61K 31/415* (2013.01)

(58) Field of Classification Search
CPC ........................... A61K 31/415; A61K 9/7061
See application file for complete search history.

(56) References Cited

U.S. PATENT DOCUMENTS

| 4,475,944 | A | 10/1984 | Rorer |
| 4,826,867 | A | 5/1989 | Jensen-Korte et al. |
| 6,727,401 | B1 * | 4/2004 | Venkateshwaran ... A61F 13/105 424/448 |
| 6,916,814 | B2 | 7/2005 | Moss et al. |
| 7,265,224 | B2 | 9/2007 | Park et al. |
| 8,889,727 | B2 | 1/2014 | Ohyama |
| 8,771,726 | B2 | 7/2014 | Toshimitsu et al. |
| 2004/0152725 | A1 | 8/2004 | Moss et al. |
| 2006/0193900 | A1 * | 8/2006 | Yasukochi ............. C09J 139/06 424/448 |
| 2010/0282269 | A1 | 11/2010 | Uchida et al. |
| 2010/0291012 | A1 * | 11/2010 | Guy ................... A61K 31/5375 424/61 |
| 2014/0030209 | A1 | 1/2014 | Furuta et al. |

FOREIGN PATENT DOCUMENTS

| EP | 2669274 A1 | 12/2013 |
| ES | 2015648 A6 | 9/1990 |
| JP | 63068569 A | 3/1988 |
| JP | 2003344278 A | 12/2003 |
| JP | 2005118398 A | 5/2005 |
| JP | 2008169155 A | 7/2008 |
| JP | 4284169 B2 | 6/2009 |
| JP | 2010189440 A | 9/2010 |
| JP | 2011140504 A | 7/2011 |
| JP | 2012036198 A | 2/2012 |
| WO | 9503775 A1 | 2/1995 |
| WO | 03005999 A2 | 1/2003 |
| WO | 2004033432 A1 | 4/2004 |
| WO | 2004084826 A2 | 10/2004 |
| WO | 2008024978 A2 | 2/2008 |
| WO | 2012102404 A1 | 8/2012 |

OTHER PUBLICATIONS

RN 83430-98-2, Database Registry Chemical Abstracts Service, Columbus, Ohio, Accession No. RN 83430-98-2, Entered STN: Nov. 16, 1984.
A. K. Gupta, et al., "Prevalence and epidemiology of toenail onychomycosis in diabetic subjects: a multicentre survey", British Journal of Dermatology 1998, 139, pp. 665-671.
BASF, "Kollidon VA64 Fine", Aug. 2011 (abstract).
Extended European Search Report dated Dec. 4, 2015, issued in counterpart European Application No. 13825029.5.
International Search Report (ISR) dated Sep. 3, 2013 issued in International Application no. PCT/JP2013/070527.
K. Anandarajagopal, et al., "Antiepileptic and Antimicrobial Activities of Novel 1-(unsubstituted/substituted)-3,5-dimethyl-1H-pyrazole Derivatives", International Journal of ChemTech Research, Jan.-Mar. 2010, vol. 2, No. 1, pp. 45-49.
Kenzo Sirakawa, et al., "[Pyrazolyl1-(1)-pyrimidine", Annual Report of Takeda Research Center, 1963, vol. 22, pp. 27-46 (and English language translation thereof; pp. 1-29).
Hideyo Yamaguchi, "Pathogenic Fungi and Mycosis", Nanzando Co., Ltd., Revised 2nd Edition, 2003, pp. 42-45, including English language translation thereof.
Hideyo Yamaguchi, "Pathogenic Fungi and Mycosis", Nanzando Co., Ltd., Revised 2nd Edition, 2003, pp. 184-187, including English language translation thereof.
English language translation of (pp. 1-16) of Hideyo Yamaguchi, "Pathogenic Fungus and Mycosis 5", Nanzando, Revised Version 2, 2003, pp. 42-45, 184-187.
Fukata, "Cyclodienones. 9. Reaction of 4-Halo-2, 4, 6-Tri-Tert-Butyl-2, 5-Cyclohexadien-1-Ones With Pyrazoles and Preparation of 1-(2-Hydroxyphenyl) and 1-(4Hydroxyphenyl) Pyrazoles", Heterocycles, 1982, vol. 19, No. 8, pp. 1478-1495.

(Continued)

*Primary Examiner* — Jianfeng Song
(74) *Attorney, Agent, or Firm* — Holtz, Holtz & Volek PC

(57) ABSTRACT

A patch for a nail for treating dermatophytosis which includes a pressure-sensitive adhesive layer containing an acrylic-based pressure-sensitive adhesive and 2-(3, 5-dimethyl-1H-pyrazol-1-yl)-5-methylphenol or a salt thereof, wherein the acrylic-based pressure sensitive adhesive contains a copolymer of 2-ethylhexyl acrylate and N-vinylpyrrolidone, and wherein a mass ratio of the 2-ethylhexyl acrylate and the N-vinylpyrrolidone is 70:30 to 90:10.

10 Claims, No Drawings

(56) References Cited

OTHER PUBLICATIONS

Ito, et al., "A medium-term rat liver bioassay for rapid in vivo detection of carcinogenic potential of chemicals", Cancer Science, 94(1), 3-8 (2003).
Schneider, et al., "Skin Cosmetics", Ullmann's Encyclopedia of Industrial Chemistry; Jan. 15, 2001; Wiley-VCH Verlag GmbH & Co. KGaA.

* cited by examiner

PATCH FOR TREATING DERMATOPHYTOSIS

CROSS REFERENCE TO RELATED APPLICATIONS

This application is a Continuation Application of application Ser. No. 14/418,804 filed on Jan. 30, 2015, which is a United States National Phase application of International Application No. PCT/JP2013/070527 filed on Jul. 30, 2013. The entire contents of application Ser. No. 14/418,804 and International application No. PCT/JP2013/070527 are incorporated by reference herein.

TECHNICAL FIELD

The present invention relates to a patch for prevention or treatment of dermatophytosis comprising a novel 2-(1H-pyrazol-1-yl)phenol derivative or a pharmaceutically acceptable salt thereof as an effective ingredient suitable for an anti-dermatophytosis agent.

BACKGROUND ART

Mycosis is a disease caused by a fungus which infects to human or animals. As representative mycoses in human, there have been known candidiasis due to *Candida*, cryptococcosis due to *Ccusryptococ*, aspergillosis due to *Aspergillus*, zygomycosis due to *Zygomycetes*, dermatophytosis (trichophytia) due to *Trichophyton*, and the like (pathogenic fungi and mycosis (NANZANDO Co., Ltd., Revised 2nd Edition), pp. 42-45; Non-Patent Document 1).

*Trichophyton* which is one of pathogenic fungi of mycosis is dermatophyte which could be pathogenic fungi of trichophytia, and has the keratolytic ability. According to this ability, it invades into a skin, nail or hair to cause trichophytia (Pathogenic fungi and mycosis (NANZANDO Co., Ltd., Revised 2nd Edition), pp. 184-187; Non-Patent Document 2).

Tinea unguium is a disease of a nail caused by dermatophyte, and a disease accompanied by symptoms of turbidity, thickening, destruction, and deformation, etc. of the nail plate. At present, it is said that there is one patient per ten Japaneses, and about 12 million patients in total. This is a disease frequently appearing in aged person, and a further increase in a number of patients will be concerned in the future. There is a report that a diabetic patient easily contracts the disease so that the possibility of causing serious complications is being pointed out.

As a treatment method of onychomycosis in Japan nowadays, only an oral medicine of an antifungal agent (itraconazole and terbinafine, etc.) has been approved. However, the antifungal agent for oral administration has been pointed out that it has drug interaction, liver damage, and side effect(s) due to long term administration. In addition, an aged person, diabetic patient, etc., having a high morbidity of tinea unguium often takes multiple types of drugs, so that oral administration of the anti-fungal agent for the treatment of tinea unguium is difficult in many cases (Br. J. of Dermatol., vol. 139 (4), p. 665, 1998; Non-Patent Document 3).

As for an anti-dermatophytosis drug for external use, to exert the medical effect of the anti-dermatophytosis drug for external use, it is required to deliver the drug to an epidermal horny layer and a nail which are infected portions, with a high level of a drug concentration in addition to have the drug itself having a potent antifungal activity against dermatophytes. However, the antifungal drug for external use to be used for usual skin mycosis cannot reach to the horny or inside of the nail, or to a nail matrix with a sufficient concentration, whereby a sufficient effect cannot be obtained.

In abroad, a nail lacquer for external use of amorolfine or ciclopirox has been approved and used. However, their permeabilities into the nail are very low, so that it cannot be expected to deliver to nail matrix cells by further permeation.

Therefore, a patch for external use of dermatophytosis such as tinea unguium, etc., is required to have not only a potent antifungal activity against dermatophytes, but also high permeability to a nail, but such a patch for external use has not yet been found out.

On the other hand, as a compound having a 2-(1H-pyrazol-1-yl)phenol backbone, 2-(3,5-dimethyl-1H-pyrazol-1-yl)phenol which has methyl groups at the 3-position and 5-position of the pyrazole ring has been known (Annual Report of Takeda Research Center (1963) 22, p. 27; Non-Patent Document 4). These compounds are directed to prevent growth of *Mycobacterium tuberculosis* in human. However, in Non-Patent Document 4, there is no disclosure of the 2-(1H-pyrazol-1-yl)phenol compound other than 2-(3,5-dimethyl-1H-pyrazol-1-yl)phenol.

As the compound having a 2-(1H-pyrazol-1-yl)phenol backbone other than 2-(3,5-dimethyl-1H-pyrazol-1-yl)phenol, 2-(1H-pyrazol-1-yl)phenol, 2-(3,5-dimethyl-1H-pyrazol-1-yl)-1,4-benzenediol and 2-(4-chloro-3,5-dimethyl-1H-pyrazol-1-yl)-1,4-benzenediol have been known. These have been utilized for various kinds of chemical reactions, a starting material as a compound for electroluminescence devices (JP Patent No. 4284169: Patent Document 1), a photostabilizer (Spanish Patent Laid-Open No. 20158648A: Patent Document 2), etc. Also, in WO 2003/005999 (Patent Document 3), 2-(5-amino-3-tert-butyl-1H-pyrazol-1-yl)-5-methylphenol is disclosed.

However, in these prior art literatures, there is neither suggestion nor disclosure about its antifungal activity against dermatophytes of the compound having a 2-(1H-pyrazol-1-yl)phenol backbone.

PRIOR ART LITERATURES

Patent Documents

[Patent Document 1] JP Patent No. 4284169
[Patent Document 2] Spanish Patent Laid-Open No. 2015648A
[Patent Document 3] WO 2003/005999A

Non-Patent Documents

[Non-Patent Document 1] Pathogenic fungi and mycosis (NANZANDO Co., Ltd., Revised 2nd Edition), pp. 42-45
[Non-Patent Document 2] Pathogenic fungi and mycosis (NANZANDO Co., Ltd., Revised 2nd Edition), pp. 184-187
[Non-Patent Document 3] Br. J. of Dermatol., vol. 139 (4), p. 665, 1998
[Non-Patent Document 4] Annual Report of Takeda Research Center (1963) 22, p. 27

DISCLOSURE OF THE INVENTION

Problems to be Solved by the Invention

As mentioned above, a patch for external use of superficial mycosis such as tinea unguium is required to have not only antifungal activity, but also high permeability to a nail whereby development of such a patch for external use has been earnestly desired. Accordingly, an object of the present invention is to provide a patch for nail and/or skin having an antifungal activity against dermatophytes, and having higher nail permeability.

Means for Solving the Problems

The present inventors have found that a patch comprising the compound having a 2-(1H-pyrazol-1-yl)phenol backbone represented by the following formula (I) or a salt thereof in a pressure sensitive adhesive layer has high nail permeability and storability, whereby they have accomplished the present invention based on these findings.

That is, the present invention relates to a patch for nail and/or skin for prevention or treatment of dermatophytosis which comprises in a pressure sensitive adhesive layer a compound represented by the formula:

[Formula 1]

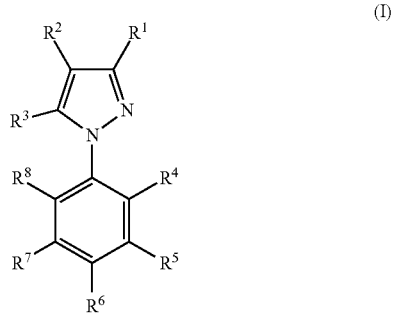

(I)

wherein
$R^1$ represents a hydrogen atom, $C_{1-6}$ alkyl, or trifluoromethyl,
$R^2$ represents a hydrogen atom, $C_{1-6}$ alkyl, halogen, —COO($C_{1-6}$ alkyl), or $(CH_2)_{1-3}$COOR (R represents a hydrogen atom or $C_{1-6}$ alkyl),
$R^3$ represents a hydrogen atom, $C_{1-6}$ alkyl, amino, trifluoromethyl, or OR (R represents a hydrogen atom or $C_{1-6}$ alkyl),
$R^4$ represents a hydroxyl group,
$R^5$ represents a hydrogen atom, $C_{1-6}$ alkyl, a hydroxyl group, or halogen,
$R^6$ represents a hydrogen atom, $C_{1-6}$ alkyl, trifluoromethyl, halogen, amino, —NR$^a$R$^b$, nitro, hydroxy-$C_{1-6}$ alkyl, —CONR$^a$R$^b$, —COO($C_{1-6}$ alkyl), —COOH, —(CH$_2$)$_{1-3}$COOR, or OR$^a$ (R represents a hydrogen atom or $C_{1-6}$ alkyl, R$^a$ and R$^b$ may be the same or different from each other, and each represent a hydrogen atom, $C_{1-6}$ alkyl, or $C_{1-6}$ acyl),
$R^7$ represents a hydrogen atom, $C_{1-6}$ alkyl, —OR (R represents a hydrogen atom or $C_{1-6}$ alkyl), or halogen, and
$R^8$ represents a hydrogen atom, $C_{1-6}$ alkyl, a hydroxyl group, amino, or nitro, or a salt thereof.

Effects of the Invention

The patch of the present invention not only shows potent antifungal activity against dermatophytes, but also has high permeability to a nail, so that it is useful as a patch for nail and/or skin for prevention or treatment of dermatophytosis, particularly tinea unguium.

BEST MODE FOR CARRYING OUT THE INVENTION

The terms "$C_{1-6}$ alkyl", and "$C_{1-6}$ alkyl" as a part of the group to be used in the present specification mean an alkyl group having 1 to 6 carbon atoms. The alkyl group may be either a linear, branched or cyclic one. There may be mentioned, for example, a $C_{1-6}$ alkyl group such as methyl, ethyl, propyl, isopropyl, butyl, isobutyl, sec-butyl, tert-butyl, pentyl, hexyl, etc., and a $C_{3-6}$ cycloalkyl group such as cyclopropyl, cyclobutyl, cyclopentyl and cyclohexyl.

The terms "$C_{1-6}$ acyl", and "$C_{1-6}$ acyl" as a part of the group to be used in the present specification mean an acyl group having 1 to 6 carbon atoms. The acyl group may be either a linear, branched or cyclic one. There may be mentioned, for example, formyl, acetyl, propionyl, butyryl, isobutyryl, etc., and preferably, formyl, acetyl, propionyl, butyryl, etc.

The term "halogen" used in the present specification means fluorine, chlorine, bromine, iodine, etc.

The terms of a group "—OR where R represents a hydrogen atom or $C_{1-6}$ alkyl" or a part of the group to be used in the present specification mean a hydroxyl group, or $C_{1-6}$ alkyloxy. Here, "$C_{1-6}$ alkyl" is the same as the above-mentioned "$C_{1-6}$ alkyl".

In "—OR$^a$" as a group or a part of the group to be used in the present specification, R$^a$ represents a hydrogen atom, $C_{1-6}$ alkyl, or $C_{1-6}$ acyl, and "—OR$^a$" represents a hydroxyl group, $C_{1-6}$ alkyloxy, or $C_{1-6}$ acyloxy. Here, "$C_{1-6}$ alkyl" is the same as the above-mentioned "$C_{1-6}$ alkyl".

With Regard to the Compound of the Formula (I) or a Salt Thereof, a Solvate Thereof As mentioned above, the present invention relates to a patch for nail and/or skin for prevention or treatment of dermatophytosis comprising the compound represented by the formula:

[Formula 2]

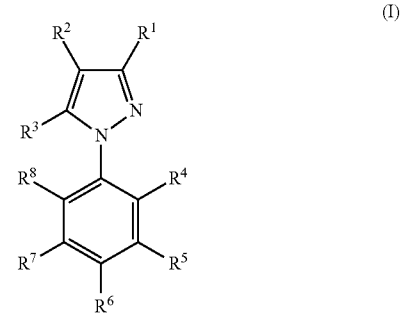

(I)

or a salt thereof, in a pressure sensitive adhesive layer.

In the formula (I), $R^1$ represents a hydrogen atom, $C_{1-6}$ alkyl, trifluoromethyl, preferably a hydrogen atom, or $C_{1-6}$ alkyl, and more preferably $C_{1-6}$ alkyl. $R^1$ specifically includes a hydrogen atom, methyl, ethyl, etc.

In the formula (I), $R^2$ represents a hydrogen atom, $C_{1-6}$ alkyl, halogen, —COO($C_{1-6}$ alkyl), or —(CH$_2$)$_{1-3}$ COOR (R represents a hydrogen atom or $C_{1-6}$ alkyl), preferably a hydrogen atom, $C_{1-6}$ alkyl, or halogen. $R^2$ specifically includes a hydrogen atom, methyl, ethyl, propyl, butyl, a chlorine atom, or 2-carboxyethyl, etc.

In the formula (I), $R^3$ represents a hydrogen atom, $C_{1-6}$ alkyl, amino, trifluoromethyl, —OR (R represents a hydrogen atom or $C_{1-6}$ alkyl), preferably a hydrogen atom, or $C_{1-6}$ alkyl, more preferably $C_{1-6}$ alkyl. $R^3$ specifically includes methyl, or ethyl.

In the formula (I), $R^4$ represents a hydroxyl group.

In the formula (I), $R^5$ represents a hydrogen atom, $C_{1-6}$ alkyl, a hydroxyl group, or halogen, preferably a hydrogen atom.

In the formula (I), $R^6$ represents a hydrogen atom, $C_{1-6}$ alkyl, trifluoromethyl, halogen, amino, —$NR^aR^b$, nitro, hydroxy-$C_{1-6}$ alkyl, —$CONR^aR^b$, —$COO(C_{1-6}$ alkyl), —COOH, —$(CH_2)_{1-3}$COOR, or $OR^a$ (R represents a hydrogen atom or $C_{1-6}$ alkyl, $R^a$ and $R^b$ may be the same or different from each other, and each represent a hydrogen atom, $C_{1-6}$ alkyl, or $C_{1-6}$ acyl), preferably a hydrogen atom, $C_{1-6}$ alkyl, trifluoromethyl, halogen, amino, —$NR^aR^b$, nitro, hydroxy-$C_{1-6}$ alkyl, —$CONR^aR^b$, —COOH, or $OR^a$ ($R^a$ and $R^b$ may be the same or different from each other, and each represent a hydrogen atom, $C_{1-6}$ alkyl, or $C_{1-6}$ acyl), more preferably a hydrogen atom, $C_{1-6}$ alkyl, halogen, or $OR^a$ ($R^a$ represents a hydrogen atom, $C_{1-6}$ alkyl, or $C_{1-6}$ acyl). $R^6$ specifically includes a hydrogen atom, methyl, ethyl, methoxy, a chlorine atom, a bromine atom, a fluorine atom, a hydroxyl group, acetoxy, amino, nitro, carboxyl, hydroxymethyl, trifluoromethyl, methylamino, carbamoyl, or N,N-dimethylcarbamoyl.

$R^7$ represents a hydrogen atom, $C_{1-6}$ alkyl, —OR (R represents a hydrogen atom or $C_{1-6}$ alkyl), or halogen, preferably a hydrogen atom.

$R^8$ represents a hydrogen atom, $C_{1-6}$ alkyl, a hydroxyl group, amino, or nitro, preferably a hydrogen atom, $C_{1-6}$ alkyl, amino, or nitro, more preferably a hydrogen atom. $R^8$ specifically includes a hydrogen atom, methyl, nitro, or amino In the patch for nail and/or skin for prevention or treatment of dermatophytosis of the present invention, a preferred compound of the formula (I) is a compound wherein
$R^1$ is a hydrogen atom or $C_{1-6}$ alkyl,
$R^2$ is a hydrogen atom, $C_{1-6}$ alkyl, halogen, or —$(CH_2)_{1-3}$COOR (R represents a hydrogen atom or $C_{1-6}$ alkyl),
$R^3$ is a hydrogen atom, or $C_{1-6}$ alkyl,
$R^4$ is a hydroxyl group,
$R^5$ is a hydrogen atom,
$R^6$ is a hydrogen atom, $C_{1-6}$ alkyl, trifluoromethyl, halogen, amino, —$NR^aR^b$, nitro, hydroxy-$C_{1-6}$ alkyl, —$CONR^aR^b$, —COOH, or $OR^a$ ($R^a$ and $R^b$ may be the same or different from each other, and each represent a hydrogen atom, $C_{1-6}$ alkyl, or $C_{1-6}$ acyl),
$R^7$ is a hydrogen atom, and
$R^8$ is a hydrogen atom, $C_{1-6}$ alkyl, amino, or nitro.

In the patch for nail and/or skin for prevention or treatment of dermatophytosis of the present invention, a more preferred compound of the formula (I) is a compound wherein
$R^1$ is $C_{1-6}$ alkyl,
$R^2$ is a hydrogen atom, $C_{1-6}$ alkyl, or halogen,
$R^3$ is $C_{1-6}$ alkyl,
$R^4$ is a hydroxyl group,
$R^5$ is a hydrogen atom,
$R^6$ is a hydrogen atom, $C_{1-6}$ alkyl, halogen, or $OR^a$ ($R^a$ represents a hydrogen atom, $C_{1-6}$ alkyl, or $C_{1-6}$ acyl),
$R^7$ is a hydrogen atom, and
$R^8$ is a hydrogen atom.

In the patch for nail and/or skin for prevention or treatment of dermatophytosis of the present invention, a further preferred compound of the formula (I) is a compound wherein $R^1$ is $C_{1-6}$ alkyl, $R^2$ is a hydrogen atom, $R^3$ is $C_{1-6}$ alkyl, $R^4$ is a hydroxyl group, $R^5$ is a hydrogen atom, $R^6$ is $C_{1-6}$ alkyl, $R^7$ is a hydrogen atom, and $R^8$ is a hydrogen atom.

As the compound of the formula (I) to be comprised in the patch for nail and/or skin for prevention or treatment of dermatophytosis of the present invention, the following compounds may be mentioned.

Preparation example 1: 2-(3,5-dimethyl-1H-pyrazol-1-yl)phenol

Preparation example 2: 2-(3,5-dimethyl-1H-pyrazol-1-yl)-4-fluorophenol

Preparation example 3: 2-(1H-pyrazol-1-yl)phenol

Preparation example 4: 2-(5-hydroxy-3-methyl-1H-pyrazol-1-yl)phenol

Preparation example 5: 2-(5-methyl-3-trifluoromethyl-1H-pyrazol-1-yl)phenol

Preparation example 6: 2-(3,5-bistrifluoromethyl-1H-pyrazol-1-yl)phenol

Preparation example 7: 2-(3-methyl-1H-pyrazol-1-yl)phenol

Preparation example 8: 2-(5-methyl-1H-pyrazol-1-yl)phenol

Preparation example 9: 2-(3,4,5-trimethyl-1H-pyrazol-1-yl)phenol

Preparation example 10: 2-(5-amino-3-tert-butyl-1H-pyrazol-1-yl)phenol

Preparation example 11: 4-chloro-2-(3,5-dimethyl-1H-pyrazol-1-yl)phenol

Preparation example 12: 2-chloro-6-(3,5-dimethyl-1H-pyrazol-1-yl)phenol

Preparation example 13: 2-(4-chloro-3,5-dimethyl-1H-pyrazol-1-yl)phenol

Preparation example 14: 2-(3,5-diethyl-1H-pyrazol-1-yl)phenol

Preparation example 15: 3-(3,5-dimethyl-1H-pyrazol-1-yl)benzene-1,2-diol

Preparation example 16: 2-(3,5-dimethyl-1H-pyrazol-1-yl)benzene-1,4-diol

Preparation example 17: 2-(4-ethyl-3,5-dimethyl-1H-pyrazol-1-yl)phenol

Preparation example 18: 5-fluoro-2-(3,4,5,-trimethyl-1H-pyrazol-1-yl)phenol

Preparation example 19: 2-(4-chloro-3,5-dimethyl-1H-pyrazol-1-yl)benzene-1,4-diol Preparation example 20: 4-fluoro-2-(3,4,5,-trimethyl-1H-pyrazol-1-yl)phenol Preparation example 21: 2-(4-chloro-3,5-dimethyl-1H-pyrazol-1-yl)-5-fluorophenol Preparation example 22: ethyl 1-(2-hydroxyphenyl)-3,5-dimethyl-1H-pyrazol-4-carboxylate Preparation example 23: methyl 3-(1-(2-hydroxyphenyl)-3,5-dimethyl-1H-pyrazol-4-yl)propanoate Preparation example 24: 2-(4-butyl-3,5-dimethyl-1H-pyrazol-1-yl)phenol Preparation example 25: 2-(3,5-dimethyl-1H-pyrazol-1-yl)-5-fluorophenol Preparation example 26: 5-chloro-2-(3,5-dimethyl-1H-pyrazol-1-yl)phenol Preparation example 27: 2-(3,5-dimethyl-1H-pyrazol-1-yl)-3-nitrophenol Preparation example 28: 2-(3,5-dimethyl-1H-pyrazol-1-yl)-5-nitrophenol Preparation example 29: 3-(1-(2-hydroxyphenyl)-3,5-dimethyl-1H-pyrazol-4-yl)propionic acid Preparation example 30: 5-chloro-2-(3,4,5-trimethyl-1H-pyrazol-1-yl)phenol Preparation example 31: 5-amino-2-(3,5-dimethyl-1H-pyrazol-1-yl)phenol
Preparation example 32: 5-nitro-2-(3,4,5-trimethyl-1H-pyrazol-1-yl)phenol
Preparation example 33: 4-(3,5-dimethyl-1H-pyrazol-1-yl)benzene-1,3-diol
Preparation example 34: 5-amino-2-(3,4,5-trimethyl-1H-pyrazol-1-yl)phenol
Preparation example 35: methyl 4-(3,5-dimethyl-1H-pyrazol-1-yl)-3-hydroxybenzenecarboxylate
Preparation example 36: 3-amino-2-(3,5-dimethyl-1H-pyrazol-1-yl)phenol
Preparation example 37: 4-(3,5-dimethyl-1H-pyrazol-1-yl)-3-hydroxybenzenecarboxylic acid
Preparation example 38: 4-(3,5-dimethyl-1H-pyrazol-1-yl)-3-hydroxy-N,N-dimethylbenzamide
Preparation example 39: 4-(3,5-dimethyl-1H-pyrazol-1-yl)-3-hydroxybenzamide
Preparation example 40: 3-hydroxy-4-(3,4,5-trimethyl-1H-pyrazol-1-yl)benzenecarboxylic acid
Preparation example 41: 3-hydroxy-4-(3,4,5-trimethyl-1H-pyrazol-1-yl)benzamide
Preparation example 42: 4-(4-chloro-3,5-dimethyl-1H-pyrazol-1-yl)-3-hydroxybenzamide
Preparation example 43: 2-(3,5-dimethyl-1H-pyrazol-1-yl)benzene-1,3-diol
Preparation example 44: 2-(3,5-dimethyl-1H-pyrazol-1-yl)-5-methylphenol
Preparation example 45: 2-(3,5-dimethyl-1H-pyrazol-1-yl)-5-methoxyphenol
Preparation example 46: 2-(3,5-dimethyl-1H-pyrazol-1-yl)-3-methylphenol
Preparation example 47: 2-(3,5-dimethyl-1H-pyrazol-1-yl)-5-hydroxymethylphenol
Preparation example 48: 2-(3,5-dimethyl-1H-pyrazol-1-yl)-5-methylaminophenol
Preparation example 49: 2-(3,5-dimethyl-1H-pyrazol-1-yl)-4-methylphenol
Preparation example 50: 2-(3,5-dimethyl-1H-pyrazol-1-yl)-5-trifluoromethylphenol
Preparation example 51: 2-(3,5-dimethyl-1H-pyrazol-1-yl)-6-methylphenol
Preparation example 52: 2-(3,5-dimethyl-1H-pyrazol-1-yl)-5-ethylphenol
Preparation example 53: 2-(4-fluoro-3,5-dimethyl-1H-pyrazol-1-yl)phenol
Preparation example 54: 5-bromo-2-(3,5-dimethyl-1H-pyrazol-1-yl)phenol
Preparation example 55: 5-bromo-2-(4-chloro-3,5-dimethyl-1H-pyrazol-1-yl)phenol
Preparation example 56: 5-bromo-2-(3,4,5-trimethyl-1H-pyrazol-1-yl)phenol
Preparation example 57: 4-(3,5-dimethyl-1H-pyrazol-1-yl)-3-hydroxyphenyl acetate
Preparation example 58: 4-(4-chloro-3,5-dimethyl-1H-pyrazol-1-yl)-3-hydroxyphenyl acetate
Preparation example 59: 3-hydroxy-4-(3,4,5-trimethyl-1H-pyrazol-1-yl)phenyl acetate
Preparation example 60: 2-(3,5-dimethyl-1H-pyrazol-1-yl)-4-methoxy-5-methylphenol
Preparation example 61: 4-chloro-2-(3,5-dimethyl-1H-pyrazol-1-yl)-5-methylphenol
Preparation example 62: 2-(3,5-dimethyl-1H-pyrazol-1-yl)-4,5-dimethylphenol
Preparation example 63: 4-(4-chloro-3,5-dimethyl-1H-pyrazol-1-yl)-benzene-1,3-diol Among these, 2-(3,5-dimethyl-1H-pyrazol-1-yl)-5-methylphenol is most preferably mentioned.

The compound of the formula (I) to be comprised in the patch for nail and/or skin for prevention or treatment of dermatophytosis of the present invention can be also used as a salt. As such a salt, there may be used a pharmaceutically acceptable optional salt, and may be specifically mentioned a pharmaceutically acceptable salt derived from an inorganic acid, an organic acid or a base. The "pharmaceutically acceptable salt" is known in this field of the art. For example, S. M. Berge et al. describe pharmaceutically acceptable salts in Journal of Pharmaceutical Sciences, 66, p. 1 et seq. (1977) in detail. Representative acid addition salts may include an inorganic acid salt such as hydrochloride, sulfate, nitrate, hydrobromide, hydroiodide, phosphate, etc.; an organic carboxylic acid salt such as acetate, trifluoroacetate, lactate, citrate, oxalate, succinate, glutarate, malate, tartrate, fumarate, mandelate, maleate, benzoate, nicotinate, phthalate, etc.; an organic sulfonate such as methanesulfonate, ethanesulfonate, 2-hydroxyethanesulfonate, benzenesulfonate, p-toluenesulfonate, 2-naphthalenesulfonate, camphor sulfonate, etc.; an acidic amino acid salt such as aspartate, glutamate, etc., but the invention is not limited to these. The acid addition salt preferably includes a salt with an inorganic acid such as hydrochloric acid, hydrobromic acid, sulfuric acid and phosphoric acid; and a salt with an organic acid such as oxalic acid, maleic acid, methanesulfonic acid, p-toluenesulfonic acid and citric acid, more preferably a salt with hydrochloric acid, hydrobromic acid, sulfuric acid and methanesulfonic acid.

The base addition salt can be prepared by reacting a carboxylic acid or a phenolic-hydroxyl group-containing portion with a suitable base during the final isolation or purification process of the present invention compound to obtain the objective material at that time. The pharmaceutically acceptable salt may include an alkali metal salt such as lithium salt, sodium salt, potassium salt, etc.; an alkaline earth metal salt such as calcium salt, magnesium salt, etc.; aluminum salt, ammonium salt, and further an organic base salt such as methylamine salt, dimethylamine salt, ethylamine salt, diethylamine salt, trimethylamine salt, triethylamine salt, tetramethylammonium salt, tetraethylammonium salt, pyridine salt, picoline salt, ethanolamine salt, diethanolamine salt, triethanolamine salt, trishydroxymethylaminomethane salt, piperidine salt, piperazine salt, dicyclohexylamine salt, N,N-dibenzylethylenediamine salt, etc.; a basic amino acid salt such as arginine salt, lysine salt, ornithine salt, etc., but the invention is not limited to these. The base addition salt preferably includes an addition salt with sodium, potassium, calcium, ethanolamine and trishydroxymethylaminomethane, more preferably an addition salt with sodium, potassium and trishydroxymethylaminomethane.

Further, the compound of the formula (I) comprised in the patch for nail and/or skin for prevention or treatment of dermatophytosis of the present invention can be also used in the form of a solvate. The term "solvate" used in the present specification means complexes with various stoichiometry formed by a solute (the compound of the formula (I) or a salt thereof in the present invention) and a solvent. The solvent for the purpose of the present invention is preferably a solvent which does not interfere the biological activities of the above-mentioned solute and is preferably a pharmaceutically acceptable material. The suitable solvent for the solvate may be exemplified by water, methanol, ethanol, ethylene glycol, propylene glycol, ethyl acetate and butyl acetate, and the present invention is not limited by these. As a solvent for the solvate, water, ethanol and ethyl acetate are preferably mentioned.

Preparation Method of Compound Represented by the Formula (I)

The 2-(1H-pyrazol-1-yl)phenol derivative represented by the formula (I) which is comprised in the patch of the present invention can be synthesized by an optional method, and, for example, it can be synthesized by the method shown in Scheme 1 or a method in accordance with the method. Incidentally, in Scheme 1, each symbol of the compound is the same as that mentioned above, P and P' each represent hydrogen or a suitable protective group, X represents a halogen or a suitable boronic acid group, and Y represents a dissociated ion of an acid used in the reaction. In the present specification, "suitable boronic acid" means boronic acid or a boronic acid ester.

isobutyl nitrite, isopropyl nitrite, tert-butyl nitrite, n-butyl nitrite, n-propyl nitrite, etc., and preferably sodium nitrite, or a nitrite ester such as isoamyl nitrite, tert-butyl nitrite, etc. are mentioned.

When a protective group is used, any group may be used so long as it is inactive in the steps other than the deprotection, and as P and P', there may be mentioned, for example, an alkyl group such as a methyl group, an isopropyl group, an allyl group, a tert-butyl group, a methoxymethyl group, a methylthiomethyl group, a benzyl group and a 9-anthrylmethyl group, an acyl group such as a pivaloyl group and a benzoyl group, or a sulfonyl group such as a p-toluenesulfonyl group and a methanesulfonyl group, and the present invention is not limited by these. Preferred protective group may be mentioned a methyl group, a p-toluenesulfonyl group and a methanesulfonyl group.

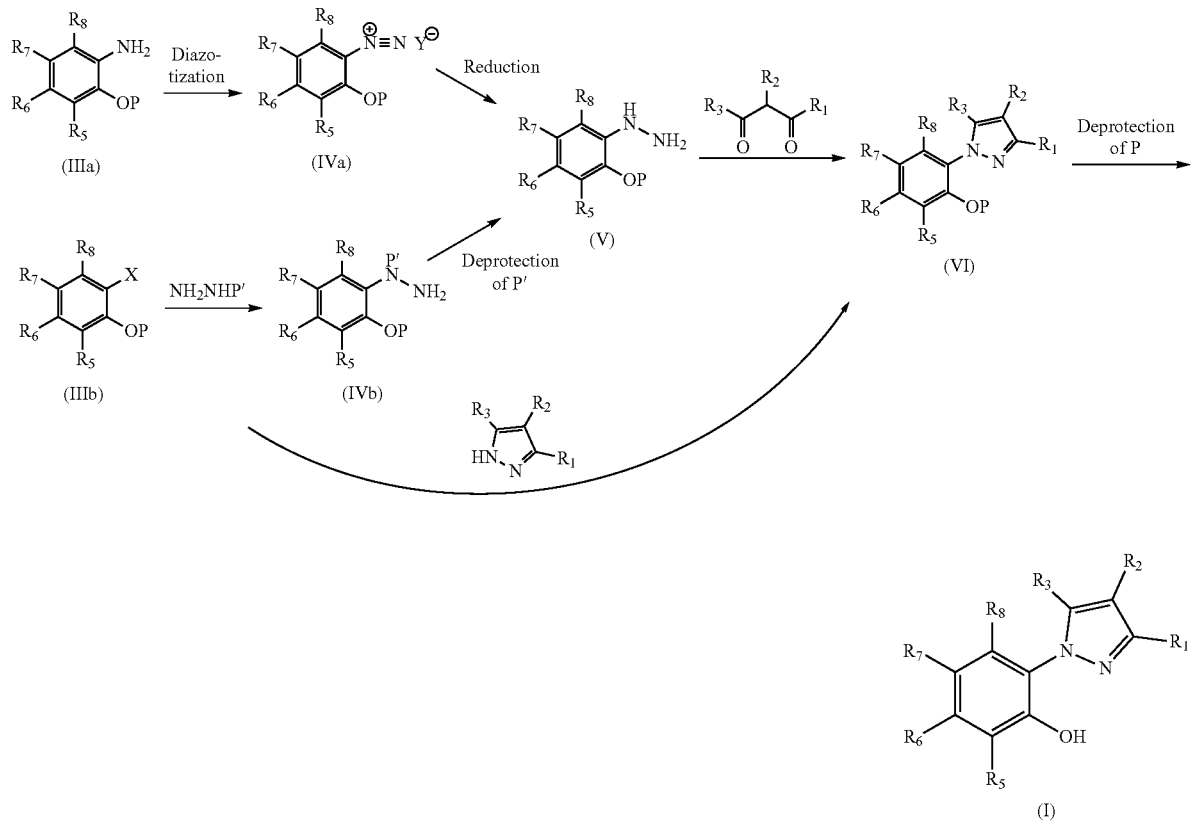

The method of obtaining a hydrazine derivative (V) or a salt thereof from a 2-hydroxyaniline derivative (IIIa) or a salt thereof via a diazonium compound (IVa) can be carried out in accordance with the method described in Organic Synthesis Collective Volume 1, pp. 442-445, J. Org. Chem., vol. 21, pp. 394-399, 1956, WO 2007/083320, or U.S. Pat. No. 6,852,890.

The diazotization reaction can be carried out by using a nitrite such as potassium nitrite, calcium nitrite, silver nitrite, sodium nitrite, barium nitrite, etc.; nitrosylsulfuric acid or a nitrite ester such as ethyl nitrite, isoamyl nitrite, The amount of the reagent to be used in the diazotization reaction is preferably 1 to 10 equivalents, more preferably 1 to 3 equivalents based on the amount of the 2-hydroxyaniline derivative (IIIa).

When a nitrite is used in the above-mentioned diazotization reaction, water, or an organic solvent mixed with water in an optional ratio, for example, methanol, ethanol, 2-propanol, acetic acid, trifluoroacetic acid, tetrahydrofuran, 1,4-dioxane, dimethylformamide and dimethylsulfoxide may be used. In addition, these solvents may be used in combination of two or more. Preferably used are water, a water-methanol mixed solution, and a water-methanol-acetic acid mixed solution. Further, the diazotization reaction is carried out under acidic conditions to ensure solubility of the aniline derivative used as a substrate and to generate nitric acid in the reaction system. The acid to be used may include hydrochloric acid, hydrobromic acid, sulfuric acid, nitric acid, acetic acid, trifluoroacetic acid and phosphoric acid. Preferably used are hydrochloric acid, acetic acid and trifluoroacetic acid. Moreover, these acids may be also used as a solvent.

When a nitrite ester is used in the above-mentioned diazotization reaction, there may be used an alcohol such as methanol, ethanol, methoxyethanol, ethoxyethanol, 1-propanol, 2-propanol, 1-butanol, 2-butanol and 2-methyl-2-propanol, an ether solvent such as diethyl ether, diisopropyl ether, tetrahydrofuran, methyl-tert-butyl ether, diphenyl ether and 1,4-dioxane, an acetic acid ester such as methyl acetate, ethyl acetate, propyl acetate and butyl acetate, an aprotic solvent such as N,N-dimethylformamide, N,N-dimethylacetamide, N-methylpyrrolidone and dimethylsulfoxide, and a halogenated solvent such as dichloromethane, chloroform and 1,2-dichloroethane. In addition, these solvents may be used in combination of two or more. Preferably used are methanol, ethanol and a mixed solution of ethanol-diethyl ether.

The temperature of the above-mentioned diazotization reaction is in either of the case where a nitrite is used or the case where a nitrite ester is used both preferably −50° C. to 50° C., more preferably between −30° C. and 10° C., further preferably between −10° C. and 5° C.

The above-mentioned diazotization reaction may vary depending on the substrate and the reaction conditions, and completes within 5 minutes to 12 hours, generally within 3 hours in many cases.

The concentration of the substrate in the solution of the above-mentioned diazotization reaction is not particularly limited and it can be carried out within the range of 0.1 mM to 10 M, preferably within the range of 1 mM to 1 M.

Reduction of the diazonium compound (IVa) to the hydrazine derivative (V) can be carried out by using stannous chloride or a hydrate thereof, a sulfite, a hydrogen sulfite, a dithionite, or triphenylphosphine (Organic Synthesis Collective Volume 1, p. 442-445, J. Org. Chem., vol. 21, pp. 394-399, 1956, WO2007/083320, U.S. Pat. No. 6,852,890, US2007/0105866, J. Am. Chem. Soc., vol. 92, pp. 853-859, 1970). Preferred is a method using stannous chloride, a dithionite, or a sulfite.

The above-mentioned reduction reaction can be carried out subsequently to the diazotization reaction. That is, without isolating diazonium compound which is generally unstable, a reducing reagent is added to the reaction solution, or the diazotization reaction solution is added to the solution of the reducing reagent whereby the hydrazine derivative (V) or a salt thereof can be synthesized.

The amount of the above-mentioned reducing agent is preferably 1 to 30 equivalents, more preferably 1 to 10 equivalents based on the amount of the corresponding diazonium compound.

The solvent to be used in the above-mentioned reduction may be the same as that used in the diazotization reaction, also, may be optionally added, and preferably the same as that used in the diazotization reaction.

The temperature of the above-mentioned reduction may vary depending on the kind of the reducing agent, and preferably −50° C. to 120° C., and the reduction may be more preferably carried out between −10° C. and 70° C., and further preferably between −10° C. and 30° C.

The hydrazine derivative (V) or a salt thereof can be synthesized from the compound (IIIb) without through the diazonium compound (IVa). That is, the compound (IIIb) is reacted with a hydrazine or a hydrazine protected by P' in the presence of a suitable catalyst, or in the absence thereof to obtain the hydrazine derivative (V) or a salt thereof.

The phenylpyrazole derivative (VI) can be similarly synthesized by reacting the compound (IIIb) with a suitable pyrazole in the presence of a suitable catalyst, or in the absence thereof.

When a hydrazine to which the protective group P' has bonded is used, the protective group may be any group so long as it is inactive in the steps other than the deprotection. As the P', there may be mentioned, for example, an alkyloxycarbonyl group such as a methoxycarbonyl group, an ethoxycarbonyl group, a tert-butoxycarbonyl group and a benzyloxycarbonyl group, etc., an acyl group such as a pivaloyl group and a benzoyl group, or a sulfonyl group such as a p-toluenesulfonyl group and a methanesulfonyl group, and the present invention is not limited by these. As the preferred protective group, there may be mentioned a t-butoxycarbonyl group.

When X of the compound (IIIb) is halogen, the reaction can be carried out in accordance with the method disclosed in Organic Letters vol. 3, pp. 3803-3805, 2001, J. Org. Chem., vol. 72, pp. 6190-6199, 2007, or J. Org. Chem., vol. 70, pp. 5164-5173, 2005. When X of the compound (IIIb) is boronic acid, the reaction can be carried out in accordance with the method disclosed in Bioorg. Med. Chem. Lett., vol. 18, pp. 4438-4441, 2008.

The amount of the hydrazine or the hydrazine protected by P' to be used in the above-mentioned reaction, or an amount of the pyrazole is preferably 1 to 30 equivalents, more preferably 1 to 5 equivalents based on the amount of the compound (IIIb).

The solvent suitable for the above-mentioned reaction may vary depending on the substrate or the reaction conditions, and there may be mentioned an aprotic solvent such as N,N-dimethylformamide, N,N-dimethylacetamide, N-methylpyrrolidone, dimethyl sulfoxide, sulfolane, acetonitrile and propionitrile, an ether solvent such as 1,4-dioxane, 1,2-dimethoxyethane and 1,2-diethoxyethane, and a halogenated solvent such as chloroform, 1,2-dichloroethane, 1,1,2,2-tetrachloroethane and 1,1,1-trichloroethane, and the present invention is not limited by these. In addition, these solvents may be used in combination of two or more. When the substrate is a liquid, it is possible to react the materials without using any solvent. The reaction is preferably carried out by using N,N-dimethylformamide, N-methylpyrrolidone, propionitrile or dimethylsulfoxide, or without any solvent.

In the above-mentioned reaction, in addition to the salt of copper or palladium, a material in which a suitable ligand is coordinated to copper or palladium may be used with a catalytic amount or with a stoichiometric amount or more. At that time, it is preferred to also use an organic base such as 1,4-diazabicyclo[2,2,2]octane, 1,8-diazabicyclo[5,4,0]undecene, pyridine and N,N-dimethylaminopyridine, or an inorganic base such as potassium tert-butoxide, sodium tert-butoxide, or potassium carbonate, cesium carbonate and potassium phosphate. Pyridine, potassium carbonate, cesium carbonate, potassium phosphate, etc. are more preferred.

As a suitable ligand, there may be mentioned tributylphosphine, triphenylphosphine, N-methylglycine, N,N-dimethylglycine, 1,2-diaminocyclohexane, 1,10-phenanthroline derivative, 8-hydroxyquinoline, picolinic acid and 2,2'-bipyridine, and the present invention is not limited by these. N,N-dimethylglycine, 1,2-diaminocyclohexane or 8-hydroxyquinoline are more preferred.

When a small amount of water, polyethylene glycol, etc., is added good results can be sometimes obtained in the above-mentioned reaction.

When X of the compound (IIIb) is boronic acid, good results can be sometimes obtained if air or oxygen is optionally blown into the reaction system.

The temperature of the above-mentioned reaction may vary depending on the kind of the substrate, presence or absence of the catalyst or the kind of the same, and is preferably 10° C. to 200° C., more preferably 20° C. to 150° C. At this time, when a microwave is irradiated, the reaction is sometimes accelerated.

The above-mentioned reaction may vary depending on the kind of the substrate, presence or absence of the catalyst or the kind of the same, and completes within 15 minutes to 96 hours, generally within 48 hours in many cases.

The concentration of the substrate in the above-mentioned reaction is not particularly limited, and the reaction is generally carried out with a concentration of 1 mM to neat (without solvent). It is preferably 10 mM to 10 M.

The deprotection of the compound (IVb) to the compound (V) or a salt thereof may be carried out by using a suitable method depending on the P' used in view of Green, Protective Groups in Organic Synthesis (5th), 1999, John Wieley & Sons. Specifically, when the P' is a tert-butoxycarbonyl group, an acid such as hydrochloric acid and trifluoroacetic acid is preferably used. At that time, when anisole or thioanisole co-exists, good results can be sometimes obtained.

The obtained hydrazine derivative (V) or a salt thereof is reacted with 1,3-diketone or its chemical equivalent to synthesize a phenylpyrazole derivative (VI) in which a pyrazole ring is formed. Here, the chemical equivalent means a compound in which the carbonyl group is protected by an acetal group, which can be easily converted into a ketone group by an acid existing in the system during the pyrazole ring-forming reaction.

The amount of the 1,3-diketone or its chemical equivalent to be used in the above-mentioned reaction is preferably 1 to 20 equivalents, more preferably 1 to 5 equivalents based on the amount of the compound (V).

The solvent suitable for the above-mentioned reaction may vary depending on the substrate or the reaction conditions, and may include an alcohol such as methanol, ethanol, methoxyethanol, ethoxyethanol, 1-propanol, 2-propanol, 1-butanol, 2-butanol, 2-methyl-2-propanol, glycerol and 1,3-propanediol, an ether solvent such as diethyl ether, diisopropyl ether, tetrahydrofuran, methyl-tert-butyl ether, diphenyl ether, 1,4-dioxane, diethylene glycol dimethyl ether, 1,2-dimethoxyethane and 1,2-diethoxyethane, an acetic acid ester such as methyl acetate, ethyl acetate, propyl acetate and butyl acetate, an aprotic solvent such as N,N-dimethylformamide, N,N-dimethylacetamide, N-methylpyrrolidone, dimethyl sulfoxide, acetonitrile and propionitrile, and a halogenated solvent such as dichloromethane, chloroform, 1,2-dichloroethane, 1,1,2,2-tetrachloroethane and 1,1,1-trichloroethane, and the present invention is not limited by these. In addition, these solvents may be used in combination of two or more. It is preferred to use methanol, ethanol, 2-propanol, 1,2-dimethoxyethane and N,N-dimethylformamide.

When the hydrazine derivative (V) is used as a free material in the above-mentioned reaction, a suitable acid may be added in an amount of a catalytic amount or 1 equivalent or more.

As a suitable acid, there may be mentioned hydrochloric acid, hydrobromic acid, sulfuric acid, nitric acid, acetic acid, trifluoroacetic acid and phosphoric acid, preferably hydrochloric acid and trifluoroacetic acid.

The temperature of the above reaction may vary depending on the kind of the substrates, and is preferably at 10° C. to 200° C., more preferably 40° C. to 120° C.

The above-mentioned reaction may vary depending on the kind of the substrate, and completes within 15 minutes to 24 hours, generally within 12 hours in many cases.

The concentration of the substrate in the above-mentioned reaction is not particularly limited, and the reaction is generally carried out with a concentration of 0.1 mM to 1 M, preferably 10 mM to 1 M.

The obtained phenylpyrazole derivative (VI) can be led to the compound (I) of the present invention, by deprotection of the protective group if necessary. The deprotection reaction may be carried out by using a suitable method depending on the P used in view of Green, Protective Groups in Organic Synthesis (5th), 1999, John Wieley & Sons. When P is a methyl group, boron tribromide, aluminum chloride, etc., is preferably used, when P is a benzyl group, catalytic hydrogenation and reduction, etc., is preferably used, and when P is a p-toluenesulfonyl group, sodium hydroxide or potassium hydroxide, etc., is preferably used.

The compound (I) of the present invention may be further chemically modified to one or both of the benzene ring side chain and the pyrazole ring side chain by an organic chemical reaction generally used. For example, the compound having a carboxyl group may be subjected to esterification, amidation, or reduction to alcohol, the compound having an amino group may be subjected to alkylation, acylation, or carbamation reaction, which are the reactions easily conceived of by those skilled in the art having knowledge in organic chemistry.

Also, the compound (I) of the present invention can be synthesized by using a 2-nitroaniline derivative (IIIc), or a nitrobenzene derivative (IIId) having a halogen or a boronic acid group at the 2-position as shown in Scheme 2. Incidentally, in Scheme 2, P' represents hydrogen or a suitable protective group, X represents halogen or a suitable boronic acid group, and Y represents a dissociated ion of an acid used in the reaction.

Scheme 2

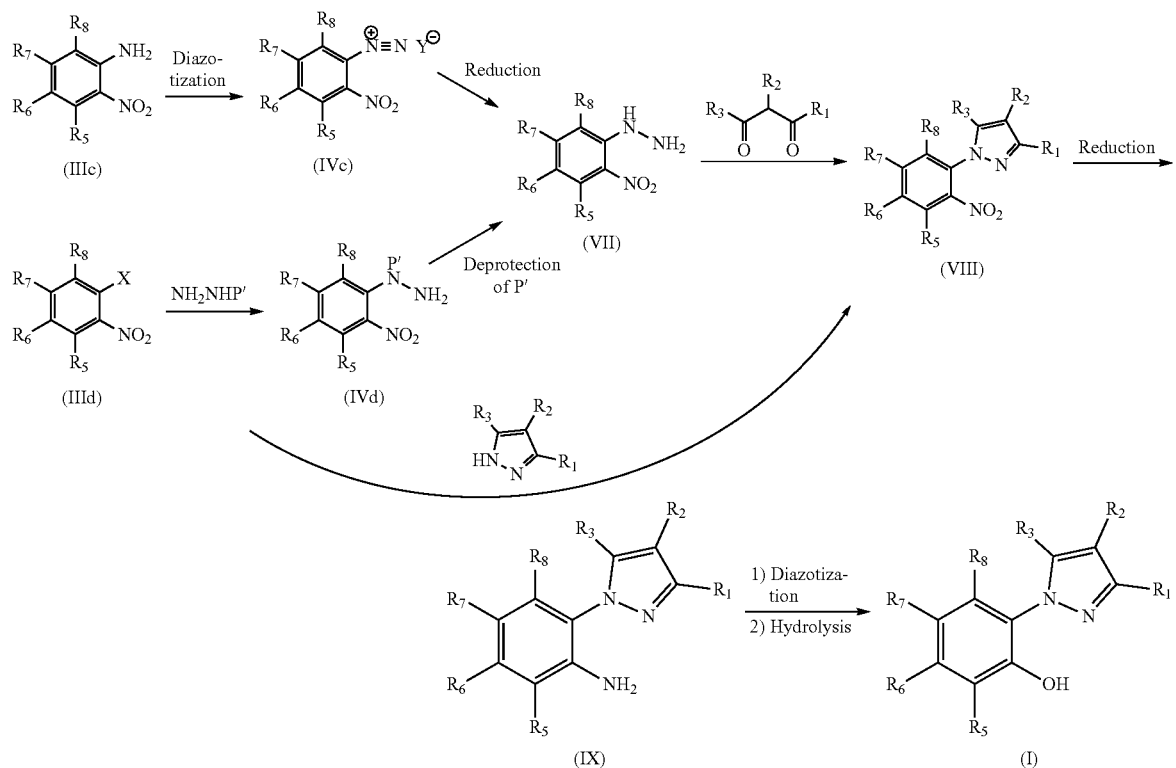

Diazotization of the 2-nitroaniline derivative (IIIc), reduction of the obtained diazonium compound, and cyclization of the pyrazole ring can be carried out in accordance with the preparation method of the above-mentioned reaction from (IIIa) to (V), and, from (V) to (VI).

The reaction from the nitrobenzene derivative (IIId) to the 2-nitrophenylpyrazole derivative (VIII) can be carried out in accordance with the preparation method of the above-mentioned reaction from (Mb) to (VI). Or else, it can be synthesized in accordance with the method described in J. Org. Chem., vol. 76, pp. 654-660, 2011.

Reduction from the 2-nitrophenylpyrazole derivative (VIII) to the 2-aminophenylpyrazole derivative (IX) can be carried out in view of Experimental Chemistry, fourth edition, pp. 159 to 266, and utilizing the catalytic hydrogenation and reduction, in the presence of an acid, reduction by a metal, reduction by a metal hydride, and the like.

In the case of the catalytic hydrogenation and reduction, the reaction is carried out with a hydrogen pressure of 1 to 80 atm, preferably 1 to 5 atm.

The solvent suitable for the above-mentioned reaction may vary depending on the substrate or the reaction conditions, and there may be mentioned an alcohol such as methanol, ethanol, methoxyethanol, ethoxyethanol, 1-propanol, 2-propanol, 1-butanol, 2-butanol and 2-methyl-2-propanol, an ether solvent such as diethyl ether, diisopropyl ether, tetrahydrofuran, methyl-t-butyl ether, diphenyl ether, diethylene glycol dimethyl ether and 1,4-dioxane, an acetic acid ester such as methyl acetate, ethyl acetate, propyl acetate and butyl acetate, and N,N-dimethylformamide, N,N-dimethylacetamide, N-methylpyrrolidone, dimethyl- sulfoxide, glycerol, 1,3-propanediol, 1,2-dimethoxyethane, 1,2-diethoxyethane, water and acetic acid, and the present invention is not limited by these. In addition, these solvents may be used in combination of two or more. It is preferred to use methanol, ethanol, 2-propanol and 1,2-dimethoxyethane.

As the catalyst to be used in the catalytic hydrogenation and reduction, there may be mentioned a metal such as palladium, platinum, rhodium and nickel, and a complex thereof, these compounds or a salt thereof which are adsorbed to activated carbon, etc., and preferably palladium carbon and Raney nickel.

The temperature of the above-mentioned catalytic hydrogenation reduction may vary depending on the kind of the substrates and catalysts, and is preferably 0° C. to 100° C., more preferably 10° C. to 50° C.

The above-mentioned catalytic hydrogenation and reduction may vary depending on the kind of the substrate, and completes within 15 minutes to 24 hours, generally within 12 hours in many cases.

The concentration of the substrate in the above-mentioned catalytic hydrogenation and reduction is not particularly limited, and the reaction is generally carried out with a concentration of 0.1 mM to 1 M, preferably 1 mM to 100 mM.

When a metal is used as a reducing agent, the metal to be used is iron, tin, zinc, etc., and it is necessary to add an acid in either of the cases. As the acid to be used there may be mentioned hydrochloric acid, sulfuric acid, acetic acid, trifluoroacetic acid and phosphoric acid, preferably hydrochloric acid. Moreover, these acids may be used also as a solvent.

The amount of the metal to be used in the above-mentioned reaction is preferably 1 to 100 equivalents, more preferably 3 to 15 equivalents based on the amount of the compound (VIII).

The solvent suitable for the above-mentioned reaction may vary depending on the substrate or the reaction conditions, and there may be mentioned water, acetic acid, an alcohol such as methanol, ethanol, methoxyethanol, ethoxyethanol, 1-propanol, 2-propanol, 1-butanol, 2-butanol and 2-methyl-2-propanol, an ether solvent such as diethyl ether, diisopropyl ether, tetrahydrofuran, diphenyl ether, diethylene glycol dimethyl ether and 1,4-dioxane, an acetic acid ester such as methyl acetate, ethyl acetate, propyl acetate and butyl acetate, and N,N-dimethylformamide, N,N-dimethylacetamide, N-methylpyrrolidone, dimethyl sulfoxide, glycerol, 1,3-propanediol, 1,2-dimethoxyethane and 1,2-diethoxyethane, and the present invention is not limited by these. In addition, these solvents may be used in combination of two or more. It is preferred to use hydrochloric acid, acetic acid, ethanol, 2-propanol and a mixture thereof.

The temperature of the above-mentioned reaction may vary depending on the kind of the substrates or conditions, and is preferably 0° C. to 100° C., more preferably 20° C. to 50° C.

The above-mentioned reaction may vary depending on the kind of the substrate and the conditions, and completes within 1 hour to 24 hours, generally within 12 hours in many cases.

The concentration of the substrate in the above-mentioned reaction is not particularly limited, and the reaction is generally carried out with a concentration of 0.1 mM to 1 M, preferably 1 mM to 100 mM.

In the case of the reduction reaction using a metal hydride, there may be used, as a reagent, lithium borohydride, sodium borohydride, potassium borohydride, zinc borohydride, lithium triethoxyborane and diisobutylaluminum hydride, preferably lithium borohydride or sodium borohydride. At that time, good results can be sometimes be obtained when stannous chloride, nickel(II) chloride, etc., co-exists.

The amount of the reducing agent to be used in the above-mentioned reaction is preferably 1 to 50 equivalents, more preferably 1 to 5 equivalents based on the amount of the compound (VIII).

The solvent suitable for the above-mentioned reaction may vary depending on the kinds of the substrate or the reducing agent, and there may be mentioned an ether solvent such as diethyl ether, diisopropyl ether, tetrahydrofuran, diphenyl ether, 1,4-dioxane, diethylene glycol dimethyl ether, 1,2-dimethoxyethane and 1,2-diethoxyethane, and an alcohol such as methanol, ethanol, methoxyethanol, ethoxyethanol, 1-propanol, 2-propanol, 1-butanol, 2-butanol and 2-methyl-2-propanol, and the present invention is not limited by these. In addition, these solvents may be used in combination of two or more. It is preferred to use methanol and a mixture of methanol and diethylene glycol dimethyl ether.

The temperature of the above-mentioned reaction may vary depending on the kind of the substrates or conditions, and is preferably −80° C. to 100° C., more preferably −20° C. to 80° C.

The above-mentioned reaction may vary depending on the kind of the substrate and the conditions, and completes within 15 minutes to 24 hours, generally within 12 hours in many cases.

The concentration of the substrate in the above-mentioned reaction is not particularly limited, and the reaction is generally carried out with a concentration of 0.1 mM to 1 M, preferably 1 mM to 100 mM.

The obtained 2-aminophenylpyrazole derivative (IX) can be diazotized in accordance with the above-mentioned preparation method of from (IIIa) to (IVa) and Japanese Unexamined Patent Publication Hei 8-53401.

The reaction from the diazonium compound to (I) can be carried out in accordance with the method described in Japanese Unexamined Patent Publication Hei 8-188545 and Japanese Unexamined Patent Publication Hei 11-60528.

Hydrolysis of the above-mentioned diazonium salt can be carried out under acidic conditions and heating in water or in a solvent containing water.

The solvent suitable for the above-mentioned reaction may vary depending on the substrate or the reaction conditions, and there may be mentioned water, acetic acid, trifluoroacetic acid, an alcohol such as methanol, ethanol, methoxyethanol, ethoxyethanol, glycerol, 1,3-propanediol, 1-propanol, 2-propanol, 1-butanol, 2-butanol and 2-methyl-2-propanol, an ether solvent such as tetrahydrofuran, diethylene glycol dimethyl ether, 1,2-dimethoxyethane, 1,2-diethoxyethane and 1,4-dioxane, and an aprotic solvent such as N,N-dimethylformamide, N,N-dimethylacetamide, N-methylpyrrolidone and dimethylsulfoxide, and the present invention is not limited by these. In addition, these solvents may be used in combination of two or more. It is preferred to use water, sulfuric acid, hydrochloric acid, trifluoroacetic acid, acetic acid, methanol, ethanol and a mixture of optional combination thereof.

The temperature of the above-mentioned reaction may vary depending on the kind of the substrates or conditions, and is preferably 20° C. to 200° C., more preferably 50° C. to 150° C.

The above-mentioned reaction may vary depending on the kind of the substrate and the conditions, and completes within 10 minutes to 24 hours, generally within 12 hours in many cases.

The concentration of the substrate in the above-mentioned reaction is not particularly limited, and the reaction is generally carried out with a concentration of 0.1 mM to 1 M, preferably 1 mM to 100 mM.

With Regard to Pressure Sensitive Adhesive

The patch for nail and/or skin for prevention or treatment of dermatophytosis of the present invention comprises the above-mentioned compound represented by the formula (I) or a salt thereof in a pressure sensitive adhesive layer. As such a pressure sensitive adhesive layer, there may be mentioned an optional pressure sensitive adhesive to be generally used for a patch for nail or skin. As the pressure sensitive adhesive, there may be mentioned, for example, an acrylic-based pressure sensitive adhesive, a silicone-based pressure sensitive adhesive, a rubber-based pressure sensitive adhesive, a urethane-based pressure sensitive adhesive, etc.

(1) Acrylic-Based Pressure Sensitive Adhesive

As the acrylic-based pressure sensitive adhesive, there may be mentioned an optional acrylic-based pressure sensitive adhesive to be generally used for a patch for nail or skin. Among these, those comprising, as a base material, a (meth)acrylic acid ester copolymer containing a (meth)acrylic acid alkyl ester having an alkyl group with 4 to 12 carbon atoms as a monomer component. As the monomer component of the (meth)acrylic acid alkyl ester, there may be mentioned an acrylic acid alkyl ester such as n-butyl acrylate, n-hexyl acrylate, n-octyl acrylate, 2-ethylhexyl acrylate, isooctyl acrylate, isononyl acrylate, n-decyl acrylate, isodecyl acrylate, 1,6-hexanediol diacrylate, etc.; and a methacrylic acid alkyl ester such as 2-ethylhexyl methacrylate, n-decyl methacrylate, isodecyl methacrylate, dodecyl methacrylate, lauryl methacrylate, etc.

In such an acrylic-based pressure sensitive adhesive, for example, a vinyl monomer having a functional group may be also formulated as the monomer component in addition to the above-mentioned (meth)acrylic acid alkyl ester. Specific examples thereof may include a monomer having a hydroxyl group such as 2-hydroxyethyl acrylate, 3-hydroxypropyl acrylate, and 4-hydroxybutyl acrylate, etc.; a monomer having a carboxyl group such as acrylic acid, methacrylic acid, etc.; a monomer having an amino group such as acrylamide, dimethyl acrylamide, diethyl acrylamide, methacrylamide and N-methylol acrylamide, etc.; a monomer having an epoxy group such as glycidyl acrylate and glycidyl methacrylate, etc.; and a non-functional group type monomer, etc.

The monomer component of the acrylic-based pressure sensitive adhesive is particularly preferably 2-ethylhexyl acrylate, acrylic acid, 1,6-hexaneglycol dimethacrylate, 2-ethylhexyl methacrylate, dodecyl methacrylate, etc.

These monomer components may be used each singly, or in admixture of two or more kinds in combination.

Other Monomer Component which can be Contained in the Monomer Component

To the acrylic-based pressure sensitive adhesive may be formulated other monomer component(s) which can be contained in addition to the above-mentioned monomer components. As such a component, there may be mentioned a vinyl monomer having a lactam ring such as N-vinyl pyrrolidine, etc.; a vinyl ester such as vinyl acetate, an unsaturated nitrile such as acrylonitrile and methacrylonitrile, etc.; and, a vinyl aromatic compound such as styrene, etc. The other monomer components which can be contained may be used each singly, or in admixture of two or more kinds in combination.

Preferred Formulation Example of Acrylic-Based Pressure Sensitive Adhesive

As the specific acrylic-based pressure sensitive adhesive, preferred is a copolymer of 2-ethylhexyl acrylate and acrylic acid, and their formulation ratio is preferably 99:1 to 90:10 (mass ratio). Also preferred is a copolymer of 2-ethylhexyl acrylate and N-vinylpyrrolidone, and their formulation ratio is preferably 70:30 to 90:10 (mass ratio).

Also preferred is a copolymer comprising 2-ethylhexyl acrylate, 2-ethylhexyl methacrylate and dodecyl methacrylate, and their formulation ratio is preferably 5:90:5 to 20:60:20 (molar ratio).

Synthesis of Acrylic-Based Pressure Sensitive Adhesive

The acrylic-based pressure sensitive adhesive can be generally synthesized by a radical polymerization. The polymerization method may include a solution polymerization method, an emulsion polymerization method or a bulk polymerization method, etc., and a solution polymerization method is preferred since good adhesive characteristics can be obtained.

The polymerization reaction can be carried out by adding a radical polymerization initiator with a ratio of 0.1 to 1% by mass or so based on the whole mass of the monomer components and polymerizing these under nitrogen atmosphere, at a temperature of 40 to 90° C. or so under stirring for several hours to several ten hours. The polymerization initiator herein used may include an organic peroxide such as benzoyl peroxide and lauroyl peroxide, etc., and an azo series initiator such as azobisisobutyronitrile, etc.

(2) Silicone-Based Pressure Sensitive Adhesive

As the silicone-based pressure sensitive adhesive, there may be used, for example, a silicone-based pressure sensitive adhesive disclosed in Japanese Unexamined Patent Publication 2006-213650. Such a silicone-based pressure sensitive adhesive may include a mixture of a silicone rubber and a silicone resin or a partial condensate thereof. As the silicone rubber, there may be mentioned a linear polydiorganosiloxane with a high molecular weight having a silicon functional group such as a silanol group at the both terminals, and the silicone resin may include a branched polyorganosiloxane or those having a network structure, which contains a 1-functional siloxane unit and a 4-functional siloxane unit, and has a silicon functional group such as a silanol group or a methoxy group in the molecule. More specifically, there may be mentioned, as the silicone rubber, a copolymer of a long chain polydimethylsiloxane, and as the silicone resin, an MQ resin (a three-dimensional structure silicone resin comprising an M unit ($(CH_3)_3SiO_{1/2}$) and a Q unit ($SiO_2$)).

A mixture ratio of the silicone rubber/silicone resin constituting the silicone-based pressure sensitive adhesive is not particularly limited, and it is preferably 30:70 to 60:40, more preferably 35:65 to 45:55 (mass ratio). Particularly preferred mixture ratio of the silicone rubber/silicone resin in the present invention may be mentioned 40/60 (w/w) (BIO-PSA7-4501, available from Dow Corning Corp.), 45/55 (w/w) (BIO-PSA7-4601, available from Dow Corning Corp.), etc.

The silicone-based pressure sensitive adhesive is an adhesive having a pressure-sensitive adhesiveness due to the silicon functional group existing in the molecule. The organic group bonded to the silicon atom may include various kinds of monovalent hydrocarbon group such as methyl, ethyl, vinyl, phenyl, etc., and the viscosity thereof can be controlled by selecting the kind of the substituents. The silicone-based pressure sensitive adhesive comprises a polyorganosiloxane as a main component which has a long intermolecular distance, so that it is enriched in air permeability and moisture permeability.

(3) Rubber-Based Pressure Sensitive Adhesive

As the rubber-based pressure sensitive adhesive, there may be used, for example, a base material in which a tackifier, for example, a hydrogenated rosin ester resin, a terpene resin, a coumarone-indene resin, a petroleum-based resin, etc., is added to a rubbery elastomer such as natural rubber, a styrene-isoprene-styrene block copolymer, polyisobutylene, polybutene, polyisoprene, etc. Preferred is a rubber-based pressure sensitive adhesive in which a styrene-isoprene-styrene block copolymer is formulated as the rubbery elastomer, and a hydrogenated rosin ester resin or a terpene resin is formulated as the tackifier. More specifically, there may preferably include a rubber-based pressure sensitive adhesive in which a hydrogenated rosin ester resin or terpene resin is formulated into a styrene-isoprene-styrene block copolymer with the ratio of 1:1.

(4) Urethane-Based Pressure Sensitive Adhesive

As the urethane-based pressure sensitive adhesive, there may be used, for example, either of the urethane-based pressure sensitive adhesives which have been used as a pressure sensitive adhesive for a percutaneous absorption patch, which are not particularly limited. More specifically, there may preferably include a urethane-based pressure sensitive adhesive obtained by reacting polyether polyol and polyether monool in the presence of an urethanization catalyst.

Formulation Ratio of the Compound of the Formula (I) or a Salt Thereof to the Pressure Sensitive Adhesive Layer The formulation ratio of the compound of the formula (I) or a salt thereof in the pressure sensitive adhesive layer can be optionally determined based on the kinds of the compounds. When the compound of the formula (I) or a salt thereof is to be formulated into the acrylic-based pressure sensitive adhesive layer, the compound of the formula (I) or a salt thereof is formulated in an amount of preferably 5 to 50% by mass, more preferably 5 to 30% by mass, further more preferably 5 to 20% by mass, particularly preferably 5 to 15% by mass into the whole acrylic-based pressure sensitive adhesive layer with a total mass standard.

When the compound of the formula (I) or a salt thereof is to be formulated into the silicone-based pressure sensitive adhesive layer, the compound of the formula (I) or a salt thereof is formulated in an amount of preferably 5 to 50% by mass, more preferably 5 to 30% by mass, further more preferably 5 to 20% by mass, particularly preferably 5 to 15% by mass into the whole silicone-based pressure sensitive adhesive layer with a total mass standard.

When the compound of the formula (I) or a salt thereof is formulated into the rubber-based pressure sensitive adhesive layer, the compound of the formula (I) or a salt thereof is formulated in an amount of preferably 5 to 50% by mass, more preferably 5 to 30% by mass, further more preferably 5 to 20% by mass, particularly preferably 5 to 15% by mass into the whole rubber-based pressure sensitive adhesive layer with a total mass standard.

When the compound of the formula (I) or a salt thereof is formulated into the urethane-based pressure sensitive adhesive layer, the compound of the formula (I) or a salt thereof is formulated in an amount of preferably 5 to 50% by mass, more preferably 5 to 30% by mass, further more preferably 5 to 20% by mass, particularly preferably 5 to 15% by mass into the whole urethane-based pressure sensitive adhesive layer with a total mass standard.

Other Additives

In the pressure sensitive adhesive layer of the patch for nail and/or skin of the present invention, a preservative, a solubilizing agent, a permeation enhancer, a filler, an antioxidant, a curing agent, etc., which are generally used for a patch may be contained in addition to the components for the above-mentioned pressure sensitive adhesive.

As the antiseptic, there may be formulated, for example, organic preservatives (cationic activator, phenols, sorbate, salicylate, dehydroacetate and benzoate, etc.), and inorganic preservatives (antibacterial zeolite in which an antibacterial metal ion such as silver, copper, zinc, etc., is ion-exchanged with zeolite, etc.). As the solubilizing agent, there may be mentioned a solubilizing agent including, for example, polyvalent alcohols (glycerine, sorbitol, ethylene glycol, propylene glycol, dipropylene glycol, 1,3-butylene glycol, 1,3-tetramethylene glycol, polyethylene glycol, etc.), phenols (thymol, safrole, isosafrole, eugenol, isoeugenol, etc.), higher alcohols (benzyl alcohol, oleyl alcohol, cetyl alcohol, stearyl alcohol, cetostearyl alcohol, octyldodecanol, etc.), ester type surfactants (sesquioleic acid sorbitane, polyoxyethylene hydrogenated castor oil, polyoxyl stearate, etc.), fatty acid esters (isopropyl myristate, octyldodecyl myristate, oleyl oleate, diethyl phthalate, dibutyl phthalate, etc.), (meth)acrylates (aminoalkyl methacrylate copolymer, etc.), and organic acids (lactic acid, citric acid, tartaric acid, maleic acid, malic acid, etc.).

As the permeation enhancer, there may be mentioned a permeation enhancer including, for example, an aliphatic acid, an aliphatic acid ester (isopropyl myristate, isopropyl palmitate, diisopropyl sebacate, diethyl sebacate, diisopropyl adipate, diethyl adipate, etc.), an aliphatic acid amide, an aliphatic alcohol, 2-(2-ethoxyethoxy)-ethanol, an ester of glycerol, glycerol monolaurate, propylene glycol, polyethylene glycol, an unsaturated polyglycolated glyceride, saturated polyglyceride, α-hydroxy acid, dimethyl sulfoxide, decylmethyl sulfoxide, pyrrolidones, salicylic acid, lactic acid, dimethylformamide, dimethylacetamide, sodium dodecyl sulfate, phospholipid, oleic acid, oleic acid/2-(2-ethoxyethoxy)ethanol, protease and N-acetylcysteine.

Also, as the filler, there may be specifically formulated calcium carbonate, magnesium carbonate, silicate, zinc oxide, titanium oxide, magnesium sulfate, calcium sulfate, etc., and as the antioxidant, there may be specifically formulated dibutyl hydroxy toluene, etc.

As the curing agent, there may be formulated a polyisocyanate (for example, COLONATE L (trimethylolpropane adduct of tolylene diisocyanate, available from NIPPON POLYURETHANE INDUSTRY CO., LTD.)), etc.

Also, for the purpose of enhancing the cohesive force of the acrylic-based pressure sensitive adhesive to be used in the pressure sensitive adhesive layer of the patch for nail and/or skin of the present invention, various kinds of cross-linking agents may be further added to the pressure sensitive adhesive layer. As the cross-linking agent, there may be mentioned a polyfunctional isocyanate compound, a polyfunctional epoxy compound and a polyvalent metal salt. More specifically, there may be preferably used a polyisocyanate (for example, COLONATE HL (trimethylolpropane adduct of hexamethylene diisocyanate, available from NIPPON POLYURETHANE INDUSTRY CO., LTD.)).

Furthermore, for the purpose of improving the adhesiveness of the silicone-based pressure sensitive adhesive to be used in the pressure sensitive adhesive layer of the patch for nail and/or skin of the present invention, various kinds of silicone fluids may be added. As the silicone fluid, there may be formulated polydimethylsiloxane fluid, dimethylsiloxane.methylphenylsiloxane copolymer fluid, dimethylsiloxane.methylvinylsiloxane copolymer fluid, dimethylsiloxane-.diphenylsiloxane copolymer fluid, dimethylsiloxane.methyl (2-phenylpropyl)siloxane copolymer fluid, dimethylsiloxane.methyl(2-phenylpropyl)siloxane.methyloctylsiloxane copolymer fluid, and polyoxyalkylene-modified polydimethylsiloxane fluid, each of both molecular ends of which are sealed by trimethylsiloxy groups.

Preparation Method of the Patch of the Present Invention

For preparing the patch of the present invention, a mixture of the compound of the formula (I) or a salt thereof which is an effective ingredient, and the pressure sensitive adhesive and other additive(s) if desired is applied on a suitable release liner, a suitable support is adhered thereon, and cut to a suitable size, if necessary, to prepare a final product.

The support usable for the patch of the present invention can be optionally selected depending on the purposes in consideration with flexibility, elasticity and a thickness, etc., in view of followability to the affected part and the easiness of affixing it at the time of pasting, etc. Such a support may include paper such as impregnated paper, coated paper, fine paper, kraft paper, Japanese paper and glassine paper, etc.; a plastic film such as a polyethylene terephthalate, polyester film, polyethylene film, polypropylene film, polyvinyl chloride film, polycarbonate film, polyurethane film and cellophane film, etc.; foam body; a cloth base material such as non-woven fabric, woven fabric and knitted fabric comprising polyester fiber, polyethylene fiber and polypropylene fiber, etc.; and a laminated material thereof.

The thickness of the support to be used is preferably from 1 μm to 200 μm, more preferably from 10 μm to 100 μm, further preferably from 20 to 50 μm.

The release liner which can be used for the patch of the present invention can be optionally selected depending on the purposes in consideration with detacheability from the pressure sensitive adhesive layer, air permeability, water permeability and flexibility, etc. It is preferred to use a film having a thickness of 10 to 200 μm or so, comprising a polymer material such as polyethylene, polypropylene and polyester, etc., and it may be used after subjecting the film surface to a silicone treatment or a fluorocarbon treatment to enhance detachability. Among these, a polyethylene terephthalate film having a thickness of 75 μm and one surface of which is subjected to a silicone treatment is preferably used.

For preparing the patch of the present invention, a general method for preparing a patch can be optionally used. More specifically, the preparation method described hereinbelow may be mentioned.

When an acrylic-based pressure sensitive adhesive is used, the acrylic-based pressure sensitive adhesive is firstly synthesized by, for example, the above-mentioned solution polymerization method, and by using a solution of the obtained acrylic-based pressure sensitive adhesive, a patch is prepared by the solution coating method.

In the solution coating method, firstly, a solution to which the prepared acrylic-based pressure sensitive adhesive solution and the compound of the formula (I) or a salt thereof, and if desired, a permeation enhancer, a solubilizing agent, a preservatives, a cross-linking agent, and other additive(s) were added is prepared. To the solution, it is possible to add an organic solvent as a diluent to optionally adjust the concentration thereof.

The organic solvent herein used may be mentioned n-hexane, toluene, ethyl acetate, acetone, methyl ethyl ketone, etc. When these organic solvents are added as a diluent, by using these organic solvents, a solution containing the acrylic-based pressure sensitive adhesive and the compound of the formula (I) or a salt thereof in an amount of preferably 10 to 50% by mass, more preferably 20 to 40% by mass based on the total mass of the whole solution is prepared.

The amount of the compound of the formula (I) or a salt thereof to be formulated in said solution can be optionally determined depending on the kind of the compound of the formula (I), the desired formulation amount of the compound of the formula (I) in the finally obtained patch, and the amount of the acrylic-based pressure sensitive adhesive.

The amount of the permeation enhancer, the solubilizing agent, the preservative, the cross-linking agent and the other additives can be optionally determined depending on the amounts of the respective components.

Next, the above-mentioned solution (diluent) containing the respective components is stirred to uniformly dissolve and disperse the respective components. The solution thus obtained is uniformly applied by using a coating machine such as a knife coater, a comma coater or a reverse coater, etc., on, for example, a release liner (a silicone-treated polyethylene terephthalate film, etc.). The applied amount of above-mentioned solution can be optionally determined depending on the thickness of the objective pressure sensitive adhesive layer, the kind of the pressure sensitive adhesive to be used, the kind of the compound of the formula (I), and an amount thereof. For example, in the case of the solution containing 30% by mass of the acrylic-based pressure sensitive adhesive based on the total mass of the solution, and 3.5% by mass of the compound of the formula (I) based on the total mass of the solution, it is preferably applied with a thickness of 10 to 300 μm, more preferably 20 to 200 μm.

After applying, the liner is maintained at a temperature of about 40° C. to 130° C. under dry-heat atmosphere for about 30 seconds to 10 minutes to volatilize the organic solvent. The drying conditions are optionally selected depending on the kind of the organic solvent to be used and the thickness of the pressure sensitive adhesive to be applied.

A patch can be obtained by laminating a support on the surface of the obtained pressure sensitive adhesive layer. Depending on the kind of the support, after forming the pressure sensitive adhesive layer on the support, a release liner may be laminated on the surface of the pressure sensitive adhesive layer.

EXAMPLES

Although the following provides a more detailed explanation of the present invention through Examples, the present invention is not limited by these Examples. In addition, "%" and "parts" in Examples mean "% by mass" and "part by mass", respectively. Furthermore, "room temperature" in Examples indicates usually from about 1° C. to about 40° C.

1. Preparation of Compounds of General formula (I)

Preparation Example 1

2-(3,5-Dimethyl-1H-pyrazol-1-yl)phenol a) 1-(2-Methoxyphenyl)-3,5-dimethyl-1H-pyrazole 3.50 g of 2-methoxyphenylhydrazine hydrochloride was dissolved in 60 ml of ethanol and 2.06 ml of acetylacetone was added, followed by heating to reflux for 1 hour. To the reaction mixture was added 150 ml of water, followed by neutralizing with a saturated aqueous sodium carbonate solution and extracting with 150 ml of ethyl acetate. The organic layer was dried over anhydrous magnesium sulfate, subsequently the solvent was distilled off under reduced pressure, and purification by silica gel column chromatography (hexane:ethyl acetate=2:1) afforded 3.88 g of the title compound.

$^1$H-NMR (CDCl$_3$); δ (ppm) 2.08 (3H, s), 2.29 (3H, s), 3.78 (3H, s), 5.95 (1H, s), 6.98-7.03 (2H, m), 7.29-7.32 (1H, m), 7.34-7.39 (1H, m).

MS (ESI); m/z 203 (M+H)$^+$ b) 2-(3,5-Dimethyl-1H-pyrazol-1-yl)phenol 3.88 g of 1-(2-methoxyphenyl)-3,5-dimethyl-1H-pyrazole was dissolved in 40 ml of methylene chloride and 32 ml of a 1M solution of boron tribromide in methylene chloride was added, followed by stirring at room temperature for 1.5 hours. The reaction mixture was added to 150 ml of water, followed by neutralizing with 1N-sodium hydroxide and extracting with 150 ml of ethyl acetate. The organic layer was dried over anhydrous magnesium sulfate, subsequently the solvent was distilled off under reduced pressure, and purification by silica gel column chromatography (hexane: ethyl acetate=3:1) afforded 2.83 g of the title compound.

$^1$H-NMR (CDCl$_3$); δ (ppm) 2.29 (3H,s), 2.38 (3H, s), 6.02 (1H, s), 6.87-6.6.91 (1H, m), 7.06-7.09 (1H, m), 7.16-7.20 (1H, m).

MS (ESI); m/z 189 (M+H)$^+$

Preparation Example 2

2-(3,5-Dimethyl-1H-pyrazol-1-yl)-4-fluorophenol a) 2-Amino-4-fluorophenol 300 mg of 4-fluoro-2-nitrophenol was dissolved in 3 ml of ethanol and 120 mg of 10% palladium/carbon was added, followed by stirring under a hydrogen atmosphere at room temperature for 1 hour. The insoluble material was filtered and subsequently the filtrate was distilled off under reduced pressure to afford 211 mg of the title compound.

$^1$H-NMR (DMSO-d6); δ (ppm) 4.80 (2H, s), 6.09-6.14 (1H, m), 6.34-6.37 (1H, m), 6.53-6.57 (1H, m), 8.93 (1H, s).

MS (FAB); m/z 128 (M+H)$^+$ b) 2-(3,5-Dimethyl-1H-pyrazol-1-yl)-4-fluorophenol

To 100 mg of 2-amino-4-fluorophenol was added 0.8 ml of 5N-hydrochloric acid and a solution of 65 mg of sodium nitrite dissolved in 0.2 ml of water was added dropwise at 0° C., followed by stirring for 30 minutes. Then, a solution of 249 mg of stannous chloride dissolved in 0.46 ml of 5N-hydrochloric acid was added dropwise at 0° C., followed by stirring at 0° C. for 30 minutes and then at room temperature for 2 hours. The solvent was distilled off under reduced pressure and 2.5 ml of ethanol and 81 μl of acetylacetone were added, followed by heating to reflux for 4 hours. To the reaction mixture was added 50 ml of water, followed by neutralizing with saturated sodium hydrogen carbonate solution and extracting with 50 ml of ethyl acetate. The organic layer was dried over anhydrous magnesium sulfate, subsequently the solvent was distilled off under reduced pressure, and purification by silica gel column chromatography (hexane:ethyl acetate=2:1) afforded 20.6 mg of the title compound.

$^1$H-NMR (CDCl$_3$); δ (ppm) 2.24 (3H, s), 2.33 (3H, s), 5.99 (1H, s), 6.82-6.90 (2H, m), 6.95-6.98 (1H, m).

MS (FAB); m/z 207 (M+H)$^+$

Preparation Example 3

2-(1H-Pyrazol-1-yl)phenol a) 1-(2-Methoxyphenyl)-1H-pyrazole 200 mg of 2-methoxyphenylhydrazine hydrochloride was dissolved in 5 ml of ethanol and 189 μl of malonaldehyde bisdimethylacetal was added, followed by heating to reflux for 2 hours. To the reaction mixture was added 50 ml of water, followed by neutralizing with a saturated aqueous sodium carbonate solution and extracting with 60 ml of ethyl acetate. The organic layer was dried over anhydrous magnesium sulfate and subsequently the solvent was distilled off under reduced pressure to afford 179.4 mg of the title compound.

$^1$H-NMR (CDCl$_3$); δ (ppm) 3.87 (3H,s), 6.42 (1H, d, J=2.4 Hz), 7.02-7.07 (2H, m), 7.27-7.32 (1H, m), 7.68-7.72 (2H, m), 8.01 (1H, d, J=2.4 Hz).

MS (FAB); m/z 175 (M+H)$^+$ b) 2-(1H-Pyrazol-1-yl)phenol 121 mg of the title compound was afforded from 178 mg of 1-(2-methoxyphenyl)-1H-pyrazole in a manner similar to Preparation example 1b).

$^1$H-NMR (CDCl$_3$); δ (ppm) 6.49 (1H, d, J=2.4 Hz), 6.88-6.92 (1H, m), 7.08-7.10 (1H, m), 7.14-7.18 (1H, m), 7.35-7.37 (1H, m), 7.72 (1H, s), 7.99 (1H, d, J=2.4 Hz).

MS (ESI); m/z 161 (M+H)$^+$

Preparation Example 4

2-(5-Hydroxy-3-methyl-1H-pyrazol-1-yl)phenol a) 5-Hydroxy-1-(2-methoxyphenyl)-3-methyl-1H-pyrazole 55.1 mg of the title compound was afforded from 150 mg of 2-methoxyphenylhydrazine hydrochloride and 93 μl of methyl acetoacetate in a manner similar to Preparation example 1a).

$^1$H-NMR (CDCl$_3$); δ (ppm) 2.11 (3H, s), 3.76 (3H, s), 6.88-6.94 (3H, m), 7.19-7.34 (2H, m).

MS (ESI); m/z 204 (M+H)$^+$ b) 2-(5-Hydroxy-3-methyl-1H-pyrazol-1-yl)phenol 32.4 mg of the title compound was afforded from 52 mg of 5-hydroxy-1-(2-methoxyphenyl)-3-methyl-1H-pyrazole in a manner similar to Preparation example 1b).

$^1$H-NMR (CDCl$_3$); δ (ppm) 2.17 (3H, s), 5.30 (1H, s), 6.88-6.95 (2H, m), 7.15 (1H, t, J=7.6 Hz), 7.37 (1H, d, J=7.6 Hz).

MS (FAB); m/z 191 (M+H)$^+$

Preparation Example 5

2-(5-Methyl-3-trifluoromethyl-1H-pyrazol-1-yl)phenol a) 1-(2-Methoxyphenyl)-5-methyl-3-trifluoromethyl-1H-pyrazole 300 mg of 2-methoxyphenylhydrazine hydrochloride was dissolved in 1.3 ml of 2-methoxyethanol, and 2.5 ml of acetic acid and 208 μl of 1,1,1-trifluoro-2,4-pentanedione were added, followed by heating to reflux for 1 hour and 40 minutes. The solvent was distilled off under reduced pressure, 50 ml of ethyl acetate was added, the organic layer washed with 50 ml of saturated sodium hydrogen carbonate solution and 50 ml of saturated brine was dried over anhydrous magnesium sulfate, and the solvent was distilled off under reduced pressure to afford 485.6 mg of the title compound.

$^1$H-NMR (CDCl$_3$); δ (ppm) 2.14 (3H, s), 3.78 (3H, s), 6.40 (1H, s), 7.00-7.07 (2H, m), 7.31-7.33 (1H, m), 7.41-7.45 (1H, m).

MS (ESI); m/z 257 (M+H)$^+$ b) 2-(5-Methyl-3-(trifluoromethyl)-1H-pyrazol-1-yl)phenol 320.1 mg of the title compound was afforded from 1-(2-methoxyphenyl)-5-methyl-3-(trifluoromethyl)-1H-pyrazole in a manner similar to Preparation example 1b).

$^1$H-NMR (CDCl$_3$); δ (ppm) 2.41 (3H, s), 6.52 (1H, s), 6.95-6.99 (1H, m), 7.11-7.13 (1H, m), 7.20-7.24 (1H, m), 7.28-7.32 (1H, m).

MS (FAB); m/z 243 (M+H)$^+$

Preparation Example 6

2-(3,5-Bistrifluoromethyl-1H-pyrazol-1-yl)phenol a) 1-(2-Methoxyphenyl)-3,5-bistrifluoromethyl-1H-pyrazole The title compound was afforded from 300 mg of 2-methoxyphenylhydrazine hydrochloride and 243 μl of hexafluoroacetylacetone in a manner similar to Preparation example 5a).

$^1$H-NMR (CDCl$_3$); δ (ppm) 3.77 (3H, s), 7.01-7.06 (3H, m), 7.33 (1H, d, J=7.6 Hz), 7.49 (1H, d, J=7.6 Hz).

MS (ESI); m/z 311 (M+H)$^+$ b) 2-(3,5-Bistrifluoromethyl-1H-pyrazol-1-yl)phenol 455.6 mg of the title compound was afforded from 1-(2-methoxyphenyl)-3,5-bistrifluoromethyl-1H-pyrazole obtained in the above a) in a manner similar to Preparation example 1b).

$^1$H-NMR (CDCl$_3$); δ (ppm) 6.99-7.04 (1H, m), 7.07-7.08 (1H, m), 7.10 (1H, s), 7.32-7.41 (2H, m).

MS (FAB); m/z 297 (M+H)$^+$

Preparation Example 7

2-(3-Methyl-1H-pyrazol-1-yl)phenol a) 1-(2-Methoxyphenyl)-3-methyl-1H-pyrazole 115.1 mg of the title compound was afforded from 200 mg of 2-methoxyphenylhydrazine hydrochloride and 151 μl of 4,4-dimethoxybutan-2-one in a manner similar to Preparation example 1a).

$^1$H-NMR (CDCl$_3$); δ (ppm) 2.31 (3H, s), 3.80 (3H, s), 6.14 (1H, d, J=2.4 Hz), 6.95-6.99 (2H, m), 7.18-7.22 (1H, m), 7.61-7.63 (1H, m), 7.84 (1H, d, J=2.4 Hz).

MS (FAB); m/z 189 (M+H)$^+$ b) 2-(3-Methyl-1H-pyrazol-1-yl)phenol 76 mg of the title compound was afforded from 115 mg of 1-(2-methoxyphenyl)-3-methyl-1H-pyrazole in a manner similar to Preparation example 1b).

$^1$H-NMR (CDCl$_3$); δ (ppm) 2.36 (3H, s), 6.24 (1H, d, J=2.4 Hz), 6.85-6.89 (1H, m), 7.05-7.14 (2H, m), 7.29-7.31 (1H, m), 7.86 (1H, d, J=2.4 Hz).

MS (FAB); m/z 175 (M+H)$^+$

Preparation Example 8

2-(5-Methyl-1H-pyrazol-1-yl)phenol a) 1-(2-Methoxyphenyl)-5-methyl-1H-pyrazole 70 mg of the title compound was afforded from 200 mg of 2-methoxyphenylhydrazine hydrochloride and 151 μl of 4,4-dimethoxybutan-2-one in a manner similar to Preparation example 1a).

$^1$H-NMR (CDCl$_3$); δ (ppm) 2.07 (3H, s), 3.71 (3H, s), 6.09 (1H, s), 6.94-6.99 (2H, m), 7.24-7.26 (1H, m), 7.31-7.35 (1H, m), 7.52 (1H, s).

MS (FAB); m/z 189 (M+H)$^+$ b) 2-(5-Methyl-1H-pyrazol-1-yl)phenol 45.5 mg of the title compound was afforded from 69 mg of 1-(2-methoxyphenyl)-5-methyl-1H-pyrazole in a manner similar to Preparation example 1b).

$^1$H-NMR (CDCl$_3$); δ (ppm) 2.41 (3H, s), 6.27 (1H, d, J=1.6 Hz), 6.90-6.94 (1H, m), 7.10-7.12 (1H, m), 7.19-7.24 (2H, m), 7.66 (1H, d, J=1.6 Hz).

MS (FAB); m/z 175 (M+H)$^+$

Preparation Example 9

2-(3,4,5-Trimethyl-1H-pyrazol-1-yl)phenol a) 1-(2-Methoxyphenyl)-3,4,5-trimethyl-1H-pyrazole 200 mg of 2-methoxyphenylhydrazine hydrochloride was dissolved in 4 ml of ethanol and 134 μl of 3-methyl-2,4-pentanedione was added, followed by heating to reflux for 3 hours. To the reaction mixture was added 50 ml of water, followed by neutralizing with a saturated aqueous sodium carbonate solution and extracting with 60 ml of ethyl acetate. The organic layer was dried over anhydrous magnesium sulfate and subsequently the solvent was distilled off under reduced pressure to afford 209.8 mg of the title compound.

$^1$H-NMR (CDCl$_3$); δ (ppm) 1.98 (3H, s), 2.02 (3H, s), 2.24 (3H, s), 3.80 (3H, s), 6.99-7.04 (2H, m), 7.29-7.31 (1H, m), 7.34-7.39 (1H, m).

MS (FAB); m/z 217 (M+H)$^+$ b) 2-(3,4,5-Trimethyl-1H-pyrazol-1-yl)phenol 104 mg of the title compound was afforded from 209 mg of 1-(2-methoxyphenyl)-3,4,5-trimethyl-1H-pyrazole in a manner similar to Preparation example 1b).

$^1$H-NMR (CDCl$_3$); δ (ppm) 1.99 (3H, s), 2.25 (3H, s), 2.31 (3H, s), 6.90 (1H, t, J=8.0 Hz), 7.08 (1H, d, J=8.0 Hz), 7.06-7.20 (2H, m), 9.89 (1H, s).

MS (ESI); m/z 203 (M+H)$^+$

Preparation Example 10

2-(5-Amino-3-tert-butyl-1H-pyrazol-1-yl)phenol a) 3-tert-Butyl-1-(2-methoxyphenyl)-1H-pyrazol-5-amine 310.3 mg of the title compound was afforded from 300 mg of 2-methoxyphenylhydrazine hydrochloride and 215 mg of 4,4-dimethyl-3-oxopentanenitrile and 40 μl of acetic acid in a manner similar to Preparation example 1a).

$^1$H-NMR (CDCl$_3$); δ (ppm) 1.32 (9H, s), 3.80 (2H, s), 3.86 (3H, s), 5.51 (1H, s), 7.01-7.08 (2H, m), 7.30-7.35 (1H, m), 7.45-7.47 (1H, m).

MS (FAB); m/z 246 (M+H)$^+$ b) 2-(5-Amino-3-tert-butyl-1H-pyrazol-1-yl)phenol 66.2 mg of the title compound was afforded from 100 mg of 3-tert-butyl-1-(2-methoxyphenyl)-1H-pyrazol-5-amine in a manner similar to Preparation example 1b).

$^1$H-NMR (CDCl$_3$); δ (ppm) 1.30 (9H, s), 3.93 (2H, s), 5.55 (1H, s), 6.90 (1H, dt, J=1.6, 8.0 Hz), 7.08 (1H, dd, J=1.6, 8.0 Hz), 7.17 (1H, dt, J=1.6, 8.0 Hz), 7.47 (1H, dd, J=1.6, 8.0 Hz), 10.39 (1H, brs).

MS (FAB); m/z 232 (M+H)$^+$

Preparation Example 11

4-Chloro-2-(3,5-dimethyl-1H-pyrazol-1-yl)phenol a) 1-(5-Chloro-2-methoxyphenyl)-3,5-dimethyl-1H-pyrazole 104.8 mg of the title compound was afforded from 388 mg of 5-chloro-2-methoxyaniline hydrochloride in a manner similar to Preparation example 2b).

$^1$H-NMR (CDCl$_3$); δ (ppm) 2.11 (3H, s), 2.29 (3H, s), 3.79 (3H, s), 5.96 (1H, s), 6.93 (1H, dd, J=2.4, 7.2 Hz), 7.33-7.35 (2H, m).

MS (FAB); m/z 237 (M+H)$^+$ b) 4-Chloro-2-(3,5-dimethyl-1H-pyrazol-1-yl)phenol 67.3 mg of the title compound was afforded from 104.8 mg of 1-(5-chloro-2-methoxyphenyl)-3,5-dimethyl-1H-pyrazole in a manner similar to Preparation example 1b).

$^1$H-NMR (CDCl$_3$); δ (ppm) 2.30 (3H, s), 2.43 (3H, s), 6.05 (1H, s), 7.02 (1H, d, J=8.8 Hz), 7.14-7.20 (2H, m), 10.08 (1H, s).

MS (FAB); m/z 223 (M+H)$^+$

Preparation Example 12

2-Chloro-6-(3,5-dimethyl-1H-pyrazol-1-yl)phenol a) 1-(3-Chloro-2-methoxyphenyl)-3,5-dimethyl-1H-pyrazole 30.6 mg of the title compound was afforded from 158 mg of 3-chloro-o-anisidine in a manner similar to Preparation example 2b).

$^1$H-NMR (CDCl$_3$); δ (ppm) 2.14 (3H, s), 2.29 (3H, s), 3.49 (3H, s), 5.99 (1H,s), 7.12 (1H, t, J=8.0 Hz), 7.27-7.31 (1H, m), 7.43-7.46 (1H, m).

MS (ESI); m/z 236 (M+H)$^+$ b) 2-Chloro-6-(3,5-dimethyl-1H-pyrazol-1-yl)phenol 27.4 mg of the title compound was afforded from 63.4 mg of 1-(3-chloro-2-methoxyphenyl)-3,5-dimethyl-1H-pyrazole in a manner similar to Preparation example 1b).

$^1$H-NMR (CDCl$_3$); δ (ppm) 2.30 (3H, s), 2.40 (3H, s), 6.05 (1H, s), 6.86 (1H, t, J=8.0 Hz), 7.13-7.15 (1H, m), 7.26-7.31 (1H, m), 10.66 (1H, s).

MS (FAB); m/z 223 (M+H)$^+$

Preparation Example 13

2-(4-Chloro-3,5-dimethyl-1H-pyrazol-1-yl)phenol a) 4-Chloro-1-(2-methoxyphenyl)-3,5-dimethyl-1H-pyrazole 193.9 mg of the title compound was afforded from 174.6 mg of 2-methoxyphenylhydrazine hydrochloride and 114 μl of 3-chloropentane-2, 4-dione in a manner similar to Preparation example 1a).

$^1$H-NMR (CDCl$_3$); δ (ppm) 2.09 (3H,s), 2.29 (3H, s), 3.81 (3H, s), 7.00-7.06 (2H, m), 7.30 (1H, dd, J=1.6, 7.6 Hz), 7.38-7.43 (1H, m).

MS (FAB); m/z 237 (M+H)$^+$ b) 2-(4-Chloro-3,5-dimethyl-1H-pyrazol-1-yl)phenol 151.9 mg of the title compound was afforded from 193 mg of 4-chloro-1-(2-methoxyphenyl)-3,5-dimethyl-1H-pyrazole in a manner similar to Preparation example 1b).

$^1$H-NMR (CDCl$_3$); δ (ppm) 2.30 (3H, s), 2.37 (3H, s), 6.91-6.95 (1H, m), 7.09 (1H, dd, J=1.6, 8.0 Hz), 7.17 (1H, dd, J=1.6, 8.0 Hz), 7.21-7.25 (1H, m), 9.23 (1H, s).

MS (FAB); m/z 223 (M+H)$^+$

Preparation Example 14

2-(3,5-Diethyl-1H-pyrazol-1-yl)phenol a) 3,5-Diethyl-1-(2-methoxyphenyl)-1H-pyrazole 209.8 mg of the title compound was afforded from 174.6 mg of 2-methoxyphenylhydrazine hydrochloride and 135.5 μl of 3,5-heptanedione in a manner similar to Preparation example 1a).

$^1$H-NMR (CDCl$_3$); δ (ppm) 1.14-1.18 (3H, m), 1.25-1.31 (3H, m), 2.42 (2H, q, J=7.2 Hz), 2.67-2.73 (2H, m), 3.78 (3H, s), 6.03 (1H, s), 6.99-7.04 (2H, m), 7.31-7.40 (2H, m).

MS (FAB); m/z 231 (M+H)$^+$ b) 2-(3,5-Diethyl-1H-pyrazol-1-yl)phenol 159.2 mg of the title compound was afforded from 207 mg of 3,5-diethyl-1-(2-methoxyphenyl)-1H-pyrazole in a manner similar to Preparation example 1b).

$^1$H-NMR (CDCl$_3$); δ (ppm) 1.24-1.31 (6H, m), 2.69 (2H, q, J=7.6 Hz), 2.76 (2H, q, J=7.6 Hz), 6.11 (1H, s), 6.90 (1H, q, J=7.6 Hz), 7.09 (1H, d, J=7.6 Hz), 7.19-7.22 (2H, m), 9.69 (1H, s).

MS (FAB); m/z 217 (M+H)$^+$

Preparation Example 15

3-(3,5-Dimethyl-1H-pyrazol-1-yl)benzene-1,2-diol a) 1-(2,3-Dimethoxyphenyl)-3,5-dimethyl-1H-pyrazole 189 mg of the title compound was afforded from 306 mg of 2,3-dimethoxyaniline in a manner similar to Preparation example 2b).

$^1$H-NMR (CDCl$_3$); δ (ppm) 2.14 (3H, s), 2.29 (3H, s), 3.53 (3H, s), 3.91 (3H, s), 5.96 (1H, s), 6.96-6.70 (2H, m), 7.12 (1H, t, J=8.0 Hz).

MS (FAB); m/z 233 (M+H)$^+$ b) 3-(3,5-Dimethyl-1H-pyrazol-1-yl)benzene-1,2-diol 28.9 mg of the title compound was afforded from 186 mg of 1-(2,3-dimethoxyphenyl)-3,5-dimethyl-1H-pyrazole in a manner similar to Preparation example 1b).

$^1$H-NMR (CDCl$_3$); δ (ppm) 2.26 (3H, s), 2.38 (3H, s), 5.99 (1H, s), 6.75-6.85 (3H, m).

MS (FAB); m/z 205 (M+H)$^+$

Preparation Example 16

2-(3,5-Dimethyl-1H-pyrazol-1-yl)benzene-1,4-diol a) 1-(2,5-Dimethoxyphenyl)-3,5-dimethyl-1H-pyrazole 260.3 mg of the title compound was afforded from 306 mg of 2,5-dimethoxyaniline in a manner similar to Preparation example 2b).

$^1$H-NMR (CDCl$_3$); δ (ppm) 2.11 (3H, s), 2.30 (3H, s), 3.73 (3H, s), 3.78 (3H, s), 5.96 (1H, s), 6.91-6.93 (3H, m).

b) 2-(3,5-Dimethyl-1H-pyrazol-1-yl)benzene-1,4-diol 162.6 mg of the title compound was afforded from 260.3 mg of 1-(2,5-dimethoxyphenyl)-3,5-dimethyl-1H-pyrazole in a manner similar to Preparation example 1b).

$^1$H-NMR (DMSO-d6); δ (ppm) 2.07 (3H, s), 2.14 (3H, s), 5.93 (1H, s), 6.56 (1H, d, J=2.8 Hz), 6.66-6.69 (1H, m), 6.80 (1H, d, J=8.8 Hz), 9.02 (1H, s), 9.17 (1H, s).

MS (FAB); m/z 205 (M+H)$^+$

Preparation Example 17

2-(4-Ethyl-3,5-dimethyl-1H-pyrazol-1-yl)phenol a) 4-Ethyl-1-(2-methoxyphenyl)-3,5-dimethyl-1H-pyrazole 236.6 mg of the title compound was afforded from 200 mg of 2-methoxyphenylhydrazine hydrochloride and 155 μl of 3-ethyl-2,4-pentanedione in a manner similar to Preparation example 1a).

$^1$H-NMR (CDCl$_3$); δ (ppm) 1.13 (3H, t, J=7.6 Hz), 2.03 (3H, s), 2.27 (3H, s), 2.42 (2H, q, J=7.6 Hz), 3.79 (3H, s), 6.99-7.04 (2H, m), 7.30-7.39 (2H, m).

MS (FAB); m/z 231 (M+H)$^+$ b) 2-(4-Ethyl-3,5-dimethyl-1H-pyrazol-1-yl)phenol 196.2 mg of the title compound was afforded from 232 mg of 4-ethyl-1-(2-methoxyphenyl)-3,5-dimethyl-1H-pyrazole in a manner similar to Preparation example 1b).

¹H-NMR (CDCl₃); δ (ppm) 1.12 (3H, t, J=7.6 Hz), 2.27 (3H, s), 2.33 (3H, s), 2.43 (2H, q, J=7.6 Hz), 6.88-6.92 (1H, m), 7.08-7.10 (1H, m), 7.06-7.19 (2H, m), 9.90 (1H, s).
MS (FAB); m/z 217 (M+H)⁺

Preparation Example 18

5-Fluoro-2-(3,4,5-trimethyl-1H-pyrazol-1-yl)phenol 114.7 mg of the title compound was afforded from 201.2 mg of 2-amino-5-fluorophenol and 184 μl of 3-methyl-2,4-pentanedione in a manner similar to Preparation example 1b).
¹H-NMR (CDCl₃); δ (ppm) 1.99 (3H, s), 2.23 (3H, s), 2.28 (3H, s), 6.59-6.64 (1H, m), 6.78-6.81 (1H, m), 7.10-7.14 (1H, m).
MS (ESI); m/z 221 (M+H)⁺

Preparation Example 19

2-(4-Chloro-3,5-dimethyl-1H-pyrazol-1-yl)benzene-1,4-diol a) 4-Chloro-1-(2,5-dimethoxyphenyl)-3,5-dimethyl-1H-pyrazole
333.7 mg of the title compound was afforded from 306 mg of 2,5-dimethoxyaniline and 228 μl of 3-chloropentane-2,4-dione in a manner similar to Preparation example 2b).
¹H-NMR (CDCl₃); δ (ppm) 2.10 (3H, s), 2.29 (3H, s), 3.74 (3H, s), 3.78 (3H, s), 6.94-6.97 (2H, m), 7.26 (1H, s).
MS (FAB); m/z 267 (M+H)⁺
b) 2-(4-Chloro-3,5-dimethyl-1H-pyrazol-1-yl)benzene-1,4-diol
184.8 mg of the title compound was afforded from 329 mg of 4-chloro-1-(2,5-dimethoxyphenyl)-3,5-dimethyl-1H-pyrazole in a manner similar to Preparation example 1b).
¹H-NMR (DMSO-d6); δ (ppm) 2.05 (3H, s), 2.15 (3H, s), 6.58 (1H, d, J=2.8 Hz), 6.72 (1H, dd, J=2.8, 8.8 Hz), 6.82 (1H, d, J=8.8 Hz), 9.11 (1H, s), 9.33 (1H, s).
MS (FAB); m/z 239 (M+H)⁺

Preparation Example 20

4-Fluoro-2-(3,4,5-trimethyl-1H-pyrazol-1-yl)phenol 84.8 mg of the title compound was afforded from 111 mg of 2-amino-4-fluorophenol and 102 μl of 3-methyl-2,4-pentanedione in a manner similar to Preparation example 2b).
¹H-NMR (CDCl₃); δ (ppm) 1.99 (3H, s), 2.23 (3H, s), 2.24 (3H, s), 2.34 (3H, s), 6.87-6.95 (2H, m), 7.00-7.03 (1H, m), 9.90 (1H, s).
MS (FAB); m/z 221 (M+H)⁺

Preparation Example 21

2-(4-Chloro-3,5-dimethyl-1H-pyrazol-1-yl)-5-fluorophenol 62 mg of the title compound was afforded from 100 mg of 2-amino-5-fluorophenol and 90 μl of 3-chloropentane-2,4-dione in a manner similar to Preparation example 2b).

¹H-NMR (CDCl₃); δ (ppm) 2.29 (3H, s), 2.35 (3H, s), 6.62-6.67 (1H, m), 6.78-6.81 (1H, m), 7.10-7.14 (1H, m), 9.44 (1H, s).
MS (FAB); m/z 241 (M+H)⁺

Preparation Example 22

Ethyl 1-(2-hydroxyphenyl)-3,5-dimethyl-1H-pyrazol-4-carboxylate a) Ethyl 1-(2-methoxyphenyl)-3,5-dimethyl-1H-pyrazol-4-carboxylate
82.6 mg of the title compound was afforded from 175 mg of 2-methoxyphenylhydrazine hydrochloride and 156 μl of ethyl 2-acetyl-3-oxobutanoate in a manner similar to Preparation example 1a).
¹H-NMR (CDCl₃); δ (ppm) 1.38 (3H, t, J=7.6 Hz), 2.33 (3H, s), 2.50 (3H, s), 0.80 (3H, s), 4.32 (2H, q, J=7.6 Hz), 7.02-7.08 (2H, m), 7.30-7.32 (1H, m), 7.41-7.45 (1H, m).
MS (ESI); m/z 275 (M+H)⁺
b) Ethyl 1-(2-hydroxyphenyl)-3,5-dimethyl-1H-pyrazol-4-carboxylate
21 mg of the title compound was afforded from 82 mg of ethyl 1-(2-methoxyphenyl)-3,5-dimethyl-1H-pyrazol-4-carboxylate in a manner similar to Preparation example 1b).
¹H-NMR (CDCl₃); δ (ppm) 1.39 (3H, t, J=7.2 Hz), 2.50 (3H, s), 2.61 (3H, s), 4.34 (2H, q, J=7.2 Hz), 6.96 (1H, t, J=8.4 Hz), 7.10 (1H, d, J=8.4 Hz), 7.17 (1H, d, J=8.4 Hz), 7.26-7.30 (1H, m), 8.76 (1H, s).
MS (FAB); m/z 261 (M+H)⁺

Preparation Example 23

Methyl 3-(1-(2-hydroxyphenyl)-3,5-dimethyl-1H-pyrazol-4-yl)propanoate a) Methyl 3-(1-(2-methoxyphenyl)-3,5-dimethyl-1H-pyrazol-4-yl)propanoate
96 mg of the title compound was afforded from 174.6 mg of 2-methoxyphenylhydrazine hydrochloride and 175 μl of methyl 4-acetyl-5-oxohexanoate in a manner similar to Preparation example 1a).
¹H-NMR (CDCl₃); δ (ppm) 2.04 (3H, s), 2.27 (3H, s), 2.49-2.54 (2H, m), 2.74-2.78 (2H, m), 3.68 (3H, s), 3.79 (3H, s), 6.99-7.02 (2H, m), 7.28-7.31 (1H, m), 7.35-7.39 (1H, m).
MS (FAB); m/z 289 (M+H)⁺
b) Methyl 3-(1-(2-hydroxyphenyl)-3,5-dimethyl-1H-pyrazol-4-yl)propanoate
36.8 mg of the title compound was afforded from 96 mg of methyl 3-(1-(2-methoxyphenyl)-3,5-dimethyl-1H-pyrazol-4-yl)propanoate in a manner similar to Preparation example 1b).
¹H-NMR (CDCl₃); δ (ppm) 2.28 (3H, s), 2.34 (3H, s), 2.51 (2H, t, J=8.0 Hz), 2.77 (2H, t, J=8.0 Hz), 3.69 (3H, s), 6.91 (1H, t, J=6.8 Hz), 7.08-7.10 (1H, m), 7.17-7.26 (2H, m), 9.73 (1H, s).
MS (ESI); m/z 275 (M+H)⁺

Preparation Example 24

2-(4-Butyl-3,5-dimethyl-1H-pyrazol-1-yl)phenol a) 4-Butyl-1-(2-methoxyphenyl)-3,5-dimethyl-1H-pyrazole
273 mg of the title compound was afforded from 175 mg of 2-methoxyphenylhydrazine hydrochloride and 168 μl of 3-n-butyl 2,4-pentanedione in a manner similar to Preparation example 1a).

¹H-NMR (CDCl₃); δ (ppm) 0.94 (3H, t, J=7.2 Hz), 1.32-1.39 (2H, m), 1.45-1.50 (2H, m), 2.01 (3H, m), 2.26 (3H, s), 2.39 (2H, q, J=7.2 Hz), 3.79 (3H, s), 6.99-7.04 (2H, m), 7.30-7.38 (2H, m).
MS (FAB); m/z 259 (M+H)⁺ b) 2-(4-Butyl-3,5-dimethyl-1H-pyrazol-1-yl)phenol 208.8 mg of the title compound was afforded from 273 mg of 4-butyl-1-(2-methoxyphenyl)-3,5-dimethyl-1H-pyrazole in a manner similar to Preparation example 1b).
¹H-NMR (CDCl₃); δ (ppm) 0.95 (3H, t, J=7.6 Hz), 1.33-1.39 (2H, m), 1.43-1.48 (2H, m), 2.26 (3H, s), 2.32 (3H, s), 2.40 (2H, t, J=7.6 Hz), 6.88-6.92 (1H, m), 7.08 (1H, d, J=8.4 Hz), 7.16-7.20 (2H, m), 9.93 (1H, s).
MS (FAB); m/z 245 (M+H)⁺

Preparation Example 25

2-(3,5-Dimethyl-1H-pyrazol-1-yl)-5-fluorophenol a) 2-Amino-5-fluorophenol
252.5 mg of the title compound was afforded from 314 mg of 5-fluoro-2-nitrophenol in a manner similar to Preparation example 2a).
¹H-NMR (DMSO-d6); δ (ppm) 6.33-6.38 (1H, m), 6.45-6.48 (1H, m), 6.51-6.55 (1H, m).
MS (FAB); m/z 128 (M+H)⁺ b) 2-(3,5-Dimethyl-1H-pyrazol-1-yl)-5-fluorophenol
89.6 mg of the title compound was afforded from 150 mg of 2-amino-5-fluorophenol in a manner similar to Preparation example 2b).
¹H-NMR (CDCl₃); δ (ppm) 2.29 (3H, s), 2.37 (3H, s), 6.03 (1H, s), 6.60-6.65 (1H, m), 6.78-6.81 (1H, m), 7.13-7.16 (1H, m).
MS (ESI); m/z 207 (M+H)⁺

Preparation Example 26

5-Chloro-2-(3,5-dimethyl-1H-pyrazol-1-yl)phenol 168.8 mg of the title compound was afforded from 287 mg of 2-amino-5-chlorophenol in a manner similar to Preparation example 2b).
¹H-NMR (CDCl₃); δ (ppm) 2.30 (3H, s), 2.40 (3H, s), 6.05 (1H, s), 6.87-6.90 (1H, m), 7.10-7.14 (2H, m), 10.23 (1H, s).
MS (FAB); m/z 223 (M+H)⁺

Preparation Example 27

2-(3,5-Dimethyl-1H-pyrazol-1-yl)-3-nitrophenol 75.4 mg of the title compound was afforded from 308 mg of 2-amino-3-nitrophenol in a manner similar to Preparation example 2b).
¹H-NMR (CD₃OD); δ (ppm) 2.14 (3H, s), 2.19 (3H, s), 6.04 (1H, s), 7.27 (1H, dd, J=1.6, 7.6 Hz), 7.44 (1H, dd, J=1.6, 7.6 Hz), 7.50 (1H, t, J=7.6 Hz).
MS (FAB); m/z 234 (M+H)⁺

Preparation Example 28

2-(3,5-Dimethyl-1H-pyrazol-1-yl)-5-nitrophenol 101 mg of the title compound was afforded from 308 mg of 2-amino-5-nitrophenol in a manner similar to Preparation example 2b).
¹H-NMR (CDCl₃); δ (ppm) 2.33 (3H, s), 2.50 (3H, s), 6.13 (1H, s), 7.38 (1H, d, J=7.6 Hz), 7.79-7.81 (1H, m), 7.95 (1H, s).
MS (ESI); m/z 234 (M+H)⁺

Preparation Example 29

3-(1-(2-Hydroxyphenyl)-3,5-dimethyl-1H-pyrazol-4-yl)propionic acid 29.9 mg of methyl 3-(1-(2-hydroxyphenyl)-3,5-dimethyl-1Hpyrazol-4-yl)propanoate was dissolved in 0.6 ml of methanol and 0.29 ml of 1N-sodium hydroxide was added, followed by stirring at room temperature for 3.5 hours. To the reaction mixture was added 20 ml of water, followed by neutralizing with 1N-hydrochloric acid and extracting with 20 ml of ethyl acetate. The organic layer was dried over anhydrous magnesium sulfate and subsequently the solvent was distilled off under reduced pressure to afford 7.5 mg of the title compound.
¹H-NMR (CDCl₃); δ (ppm) 2.29 (3H, s), 2.34 (3H, s), 2.56 (2H, t, J=7.6 Hz), 2.78 (2H, t, J=7.6 Hz), 6.89-6.93 (1H, m), 7.08-7.10 (1H, m), 7.16-7.22 (2H, m).
MS (FAB); m/z 261 (M+H)⁺

Preparation Example 30

5-Chloro-2-(3,4,5-trimethyl-1H-pyrazol-1-yl)phenol 152 mg of the title compound was afforded from 287 mg of 2-amino-5-chlorophenol and 233 μl of 3-methyl-2,4-pentanedione in a manner similar to Preparation example 2b).
¹H-NMR (CDCl₃); δ (ppm) 1.99 (3H, s), 2.24 (3H, s), 2.31 (3H, s), 6.86-6.89 (1H, m), 7.09-7.11 (2H, m).
MS (FAB); m/z 227 (M+H)⁺

Preparation Example 31

5-Amino-2-(3,5-dimethyl-1H-pyrazol-1-yl)phenol 86 mg of 2-(3,5-dimethyl-1H-pyrazol-1-yl)-5-nitrophenol was dissolved in 1.7 ml of ethanol and 43 mg of 10% palladium/carbon was added, followed by stirring under a hydrogen atmosphere at room temperature for 45 minutes. The insoluble material was filtered and subsequently the solvent was distilled off under reduced pressure to afford 30.4 mg of the title compound.
¹H-NMR (CDCl₃); δ (ppm) 2.28 (3H, s), 2.33 (3H, s), 3.72 (2H, s), 5.99 (1H, s), 6.22 (1H, dd, J=2.4, 8.4 Hz), 6.40 (1H, d, J=2.4 Hz), 6.97 (1H, d, J=8.4 Hz), 9.27 (1H, s).
MS (FAB); m/z 204 (M+H)⁺

Preparation Example 32

5-Nitro-2-(3,4,5-trimethyl-1H-pyrazol-1-yl)phenol 289.5 mg of the title compound was afforded from 308 mg of 2-amino-5-nitrophenol and 233 μl of 3-methyl-2,4-pentanedione in a manner similar to Preparation example 2b).
¹H-NMR (CDCl₃); δ (ppm) 2.02 (3H, s), 2.24 (3H, s), 2.40 (3H, s), 7.33 (1H, d, J=8.8 Hz), 7.79 (1H, dd, J=2.4, 8.8 Hz), 7.94 (1H, d, J=2.4 Hz).
MS (FAB); m/z 248 (M+H)⁺

Preparation Example 33

4-(3,5-Dimethyl-1H-pyrazol-1-yl)benzene-1,3-diol a) 2,4-Dimethoxyphenylboronic acid 576 μl of 1-bromo-2,4-dimethoxybenzene was dissolved in 5.8 ml of tetrahydrofuran and 3 ml of a 1.6 mol/l solution of n-butyllithium in hexane was added dropwise under an argon atmosphere at −78° C. Then, 1.1 ml of triisopropyl borate was added, followed by stirring at −78° C. for 40 minutes and then stirring at room temperature for 2 hours. To the reaction mixture were added 40 ml of water and 1 ml of 5N-hydrochloric acid, followed by extracting with 50 ml of ethyl acetate. The organic layer was dried over anhydrous magnesium sulfate, subsequently the solvent was distilled off under reduced pressure, and purification using silica gel column chromatography (hexane:ethyl acetate=2:1) afforded 610.2 mg of the title compound.

$^1$H-NMR (CDCl$_3$); δ (ppm) 3.85 (3H, s), 3.89 (3H, s), 5.81 (2H, s), 6.46 (1H, s), 6.56 (1H, dd, J=2.0, 8.4 Hz), 7.77 (1H, d, J=8.4 Hz).

b) 1-(2,4-Dimethoxyphenyl)-3,5-dimethyl-1H-pyrazole 610.2 mg of 2,4-dimethoxyphenylboronic acid was dissolved in 6 ml of methylene chloride, 387 mg of 3,5-dimethylpyrazole, 730 mg of copper(II) acetate and 948 μl of pyridine were added, followed by stirring at room temperature overnight. To the reaction mixture was added 60 ml of water, followed by extracting with 60 ml of ethyl acetate. The organic layer was dried over anhydrous magnesium sulfate, subsequently the solvent was distilled off under reduced pressure, and purification using silica gel column chromatography (hexane:ethyl acetate=3:2) afforded 81.7 mg of the title compound.

$^1$H-NMR (CDCl$_3$); δ (ppm) 2.07 (3H, s), 2.29 (3H, s), 3.77 (3H, s), 3.85 (3H, s), 5.94 (1H, s), 6.52-6.54 (2H, m), 7.22-7.24 (1H, m).

MS (FAB); m/z 233 (M+H)$^+$ c) 4-(3,5-Dimethyl-1H-pyrazol-1-yl)benzene-1,3-diol 118.4 mg of 1-(2,4-dimethoxyphenyl)-3,5-dimethyl-1H-pyrazole was dissolved in 2.3 ml of methylene chloride and 1.7 ml of a 1M solution of boron tribromide in methylene chloride was added, followed by stirring at room temperature for 1 hour. The reaction mixture was added to 30 ml of water, followed by neutralizing with 1N-sodium hydroxide and extracting with 50 ml of ethyl acetate. The organic layer was dried over anhydrous magnesium sulfate, subsequently the solvent was distilled off under reduced pressure, and purification using preparative thin-layer silica gel column chromatography (hexane:ethyl acetate=1:2) afforded 71.7 mg of the title compound.

$^1$H-NMR (CDCl$_3$); δ (ppm) 2.29 (3H, s), 2.33 (3H,s), 6.01 (1H, s), 6.37 (1H, dd, J=2.8, 8.8 Hz), 6.53 (1H, d, J=2.8 Hz), 7.03 (1H, d, J=8.8 Hz).

MS (ESI); m/z 205 (M+H)$^+$

Preparation Example 34

5-Amino-2-(3,4,5-trimethyl-1H-pyrazol-1-yl)phenol 118.4 mg of the title compound was afforded from 200 mg of 5-nitro-2-(3,4,5-trimethyl-1H-pyrazol-1-yl)phenol in a manner similar to Preparation example 31.

$^1$H-NMR (CDCl$_3$); δ (ppm) 1.97 (3H, s), 2.23 (3H, s), 2.24 (3H, s), 3.70 (2H, s), 6.22 (1H, dd, J=2.4, 8.4 Hz), 6.40 (1H, d, J=2.4 Hz), 6.95 (1H, d, J=8.4 Hz), 9.34 (1H, s).

MS (FAB); m/z 218 (M+H)$^+$

Preparation Example 35

Methyl 4-(3,5-dimethyl-1H-pyrazol-1-yl)-3-hydroxybenzenecarboxylate 239.4 mg of the title compound was afforded from 334 mg of methyl 4-amino-3-hydroxybenzenecarboxylate in a manner similar to Preparation example 2b).

$^1$H-NMR (CDCl$_3$); δ (ppm) 2.31 (3H, s), 2.45 (3H, s), 3.92 (3H, s), 6.08 (1H, s), 7.26-7.29 (1H, m), 7.60 (1H, dd, J=1.6, 8.0 Hz), 7.76 (1H, d, J=1.6 Hz).

MS (ESI); m/z 247 (M+H)$^+$

Preparation Example 36

3-Amino-2-(3,5-dimethyl-1H-pyrazol-1-yl)phenol 38.9 mg of the title compound was afforded from 56.6 mg of 2-(3,5-dimethyl-1H-pyrazol-1-yl)-3-nitrophenol in a manner similar to Preparation example 31.

$^1$H-NMR (CDCl$_3$); δ (ppm) 2.14 (3H, s), 2.25 (3H, s), 3.57 (2H, s), 6.02 (1H, s), 6.32-6.37 (2H, m), 7.02 (1H, t, J=8.0 Hz).

MS (FAB); m/z 204 (M+H)$^+$

Preparation Example 37

4-(3,5-Dimethyl-1H-pyrazol-1-yl)-3-hydroxybenzene carboxylic acid 100 mg of methyl 4-(3,5-dimethyl-1H-pyrazol-1-yl)-3-hydroxybenzenecarboxylate was dissolved in 1 ml of methanol and 1.6 ml of 1N-sodium hydroxide was added, followed by stirring at room temperature for 3.5 hours. To the reaction mixture was added 20 ml of water, followed by neutralizing with 1N-hydrochloric acid and extracting with 20 ml of ethyl acetate. The organic layer was dried over anhydrous magnesium sulfate and subsequently the solvent was distilled off under reduced pressure to afford 40.8 mg of the title compound.

$^1$H-NMR (CD$_3$OD); δ (ppm) 2.16 (3H, s), 2.24 (3H, s), 6.04 (1H, s), 7.30 (1H, d, J=8.4 Hz), 7.59 (1H, dd, J=2.0, 8.4 Hz), 7.64 (1H, d, J=2.0 Hz).

MS (ESI); m/z 233 (M+H)$^+$

Preparation Example 38

4-(3,5-Dimethyl-1H-pyrazol-1-yl)-3-hydroxy-N,N-dimethylbenzamide 36 mg of 4-(3,5-dimethyl-1H-pyrazol-1-yl)-3-hydroxybenzene carboxylic acid was dissolved in 0.4 ml of dimethylformamide, and 36 mg of 1-(3-dimethylaminopropyl)-3-ethylcarbodiimide hydrochloride, 25 mg of 1-hydroxybenzotriazole and 93 μl of dimethylamine (a 2.0M THF solution) were added, followed by stirring at room temperature for 4 hours. To the reaction mixture was added 10 ml of water, followed by extracting with 15 ml of ethyl acetate. The organic layer was dried over anhydrous magnesium sulfate, subsequently the solvent was distilled off under reduced pressure, and purification using preparative thin-layer silica gel column chromatography (ethyl acetate) afforded 11.4 mg of the title compound.

$^1$H-NMR (CDCl$_3$); δ (ppm) 2.31 (3H, s), 2.41 (3H, s), 3.02 (3H, s), 3.11 (3H, s), 6.06 (1H, s), 6.97 (1H, d, J=8.0 Hz), 7.23 (1H, d, J=8.0 Hz), 7.26 (1H, s).

MS (ESI); m/z 259 (M+H)$^+$

Preparation Example 39

4-(3,5-Dimethyl-1H-pyrazol-1-yl)-3-hydroxybenzamide 34.3 mg of the title compound was afforded from 73.1 mg of 4-(3,5-dimethyl-1H-pyrazol-1-yl)-3-hydroxybenzene carboxylic acid and 38 μl of aqueous ammonia in a manner similar to Preparation example 38.

$^1$H-NMR (CD$_3$OD); δ (ppm) 2.16 (3H, s), 2.24 (3H, s), 6.04 (1H, s), 7.29 (1H, d, J=8.4 Hz), 7.41 (1H, dd, J=2.0, 8.4 Hz), 7.50 (1H, d, J=2.0 Hz).

MS (ESI); m/z 232 (M+H)$^+$

Preparation Example 40

3-Hydroxy-4-(3,4,5-trimethyl-1H-pyrazol-1-yl)benzene carboxylic acid a) Methyl 3-hydroxy-4-(3,4,5-trimethyl-1H-pyrazol-1-yl)-benzenecarboxylate 110.4 mg of the title compound was afforded from 167 mg of methyl 4-amino-3-hydroxybenzenecarboxylate and 116 μl of 3-methyl-2,4-pentanedione in a manner similar to Preparation example 2b).

$^1$H-NMR (CDCl$_3$); δ (ppm) 2.00 (3H, s), 2.26 (3H, s), 2.36 (3H, s), 3.92 (3H, s), 7.23-7.26 (1H, m), 7.58-7.60 (1H, m), 7.49 (1H, s), 10.53 (1H, s).

MS (ESI); m/z 261 (M+H)$^+$ b) 3-Hydroxy-4-(3,4,5-trimethyl-1H-pyrazol-1-yl)benzene carboxylic acid 68.7 mg of the title compound was afforded from 110 mg of methyl 3-hydroxy-4-(3,4,5-trimethyl-1H-pyrazol-1-yl)-benzene carboxylate in a manner similar to Preparation example 37.

$^1$H-NMR (CD$_3$OD); δ (ppm) 1.99 (3H, s), 2.09 (3H, s), 2.20 (3H, s), 7.28 (1H, d, J=8.0 Hz), 7.59 (1H, dd, J=2.0, 8.0 Hz), 7.63 (1H, d, J=2.0 Hz).

MS (ESI); m/z 247 (M+H)$^+$

Preparation Example 41

3-Hydroxy-4-(3,4,5-trimethyl-1H-pyrazol-1-yl)benzamide 33.3 mg of the title compound was afforded from 65 mg of 3-hydroxy-4-(3,4,5-trimethyl-1H-pyrazol-1-yl)benzene carboxylic acid and 32 μl of aqueous ammonia in a manner similar to Preparation example 38.

$^1$H-NMR (CD$_3$OD); δ (ppm) 1.99 (3H, s), 2.09 (3H, s), 2.19 (3H, s), 7.27 (1H, d, J=8.0 Hz), 7.40 (1H, dd, J=2.0, 8.0 Hz), 7.57 (1H, d, J=2.0 Hz).

MS (ESI); m/z 246 (M+H)$^+$

Preparation Example 42

4-(4-Chloro-3,5-dimethyl-1H-pyrazol-1-yl)-3-hydroxybenzamide a) Methyl 4-(4-chloro 3,5-dimethyl-1H-pyrazol-1-yl)-3-hydroxybenzoate 69.1 mg of the title compound was afforded from 167 mg of methyl 4-amino-3-hydroxybenzoate and 114 μl of 3-chloropentane-2,4-dione in a manner similar to Preparation example 2b).

$^1$H-NMR (CDCl$_3$); δ (ppm) 2.32 (3H, s), 2.42 (3H, s), 3.93 (3H, s), 7.24-7.26 (1H, m), 7.60-7.66 (1H, m), 7.77 (1H, s).

b) 4-(4-Chloro-3,5-dimethyl-1H-pyrazol-1-yl)-3-hydroxybenzoic acid 39.2 mg of the title compound was afforded from 6 9.1 mg of methyl 4-(4-chloro 3,5-dimethyl-1H-pyrazol-1-yl)-3-hydroxybenzoate in a manner similar to Preparation example 37.

$^1$H-NMR (CD$_3$OD); δ (ppm) 2.15 (3H, s), 2.24 (3H, s), 7.32-7.35 (1H, m), 7.59-7.66 (2H, m).

MS (ESI); m/z 267 (M+H)$^+$ c) 4-(4-Chloro-3,5-dimethyl-1H-pyrazol-1-yl)-3-hydroxybenzamide 12.3 mg of the title compound was afforded from 37.9 mg of 4-(4-chloro-3,5-dimethyl-1H-pyrazol-1-yl)-3-hydroxybenzoic acid and 17 μl of aqueous ammonia in a manner similar to Preparation example 38.

$^1$H-NMR (CD$_3$OD); δ (ppm) 2.14 (3H, s), 2.24 (3H, s), 7.29-7.32 (1H, m), 7.41-7.44 (1H, m), 7.50 (1H, s).

MS (ESI); m/z 266 (M+H)$^+$

Preparation Example 43

2-(3,5-Dimethyl-1H-pyrazol-1-yl)benzene-1,3-diol a) 2-Aminobenzene-1,3-diol 465 mg of 2-nitroresorcinol was dissolved in 9.3 ml of ethanol, 230 mg of 10% palladium/carbon was added, followed by stirring under a hydrogen atmosphere at room temperature for 1 hour. The insoluble material was filtered and subsequently the solvent was distilled off under reduced pressure to afford 338.5 mg of the title compound.

$^1$H-NMR (DMSO-d6); δ (ppm) 6.20-6.28 (3H, m).

MS (ESI); m/z 126 (M+H)$^+$ b) 2-Amino-1,3-phenylene bis(4-methylbenzenesulfonate)

100 mg of 2-aminobenzene-1,3-diol was dissolved in 2 ml of dichloromethane, 234 μl of triethylamine and 320 mg of p-toluenesulfonyl chloride were added, followed by stirring at room temperature for 1.5 hours. To the reaction mixture was added 20 ml of water, followed by extracting with 20 ml of ethyl acetate. The organic layer was dried over anhydrous magnesium sulfate, subsequently the solvent was distilled off under reduced pressure, and purification using silica gel column chromatography (hexane:ethyl acetate=4:1) afforded 278.1 mg of the title compound.

$^1$H-NMR (CDCl$_3$); δ (ppm) 2.46 (6H, s), 3.83 (2H, s), 6.48 (1H, t, J=8.1 Hz), 6.79 (2H, d, J=8.3 Hz), 7.32 (4H, d, J=8.1 Hz), 7.72 (4H, d, J=8.3 Hz).

MS (ESI); m/z 434 (M+H)$^+$ c) 2-(3,5-Dimethyl-1H-pyrazol-1-yl)-3-hydroxyphenyl 4-methylbenzenesulfonate To 278 mg of 2-amino-1,3-phenylene bis(4-methylbenzenesulfonate) was added 0.64 ml of 5N-hydrochloric acid, and a solution of 58 mg of sodium nitrite dissolved in 0.4 ml of water was added dropwise at 0° C., followed by stirring for 30 minutes. Then, a solution of 289 mg of stannous chloride dissolved in 0.32 ml of 5N-hydrochloric acid was added dropwise at 0° C., followed by stirring for 1 hour. The solvent was distilled off under reduced pressure, and 1.3 ml of ethanol and 66 μl of acetylacetone were added, followed by heating to reflux for 2 hours. To the reaction mixture was added 50 ml of water, followed by neutralizing with saturated sodium hydrogen carbonate solution and extracting with 50 ml of ethyl acetate. The organic layer was dried over anhydrous magnesium sulfate, subsequently the solvent was distilled off under reduced pressure, and purification using silica gel column chromatography (hexane:ethyl acetate=4:1-1:1) afforded 62.9 mg of the title compound.

$^1$H-NMR (CDCl$_3$); δ (ppm) 2.15 (3H, s), 2.17 (3H, s), 2.41 (3H, s), 5.91 (1H, s), 6.93-6.-96 (2H, m), 7.14 (2H, d, J=8.0 Hz), 7.18-7.26 (1H, m), 7.35 (2H, d, J=8.0 Hz).

MS (ESI); m/z 359 (M+H)$^+$ d) 2-(3,5-Dimethyl-1H-pyrazol-1-yl)benzene-1,3-diol

To 62 mg of 2-(3,5-dimethyl-1H-pyrazol-1-yl)-3-hydroxyphenyl 4-methylbenzenesulfonate was added a solution of 97 mg of potassium hydroxide dissolved in 1.5 ml of ethanol and 1.5 ml of water, followed by heating to reflux for 3.5 hours. To the reaction mixture was added 20 ml of water, followed by extracting with 20 ml of ethyl acetate. The organic layer was dried over anhydrous magnesium sulfate, subsequently the solvent was distilled off under reduced pressure, and purification using preparative thin-layer silica gel column chromatography (hexane:ethyl acetate=1:1) afforded 20.8 mg of the title compound.

$^1$H-NMR (CDCl$_3$); δ (ppm) 2.15 (3H, s), 2.16 (3H, s), 5.98 (1H, s), 6.45 (2H, d, J=8.4 Hz), 7.00 (1H, t, J=8.4 Hz).

MS (ESI); m/z 205 (M+H)$^+$

Preparation Example 44

2-(3,5-Dimethyl-1H-pyrazol-1-yl)-5-methylphenol a) 2-Amino-5-methylphenyl 4-methylbenzenesulfonate 400 mg of 2-amino-5-methylphenol was dissolved in 6.5 ml of dichloromethane, and 476 μl of triethylamine and 619 mg of p-toluenesulfonyl chloride were added, followed by stirring at room temperature for 1 hour. To the reaction mixture was added 60 ml of water, followed by extracting with 60 ml of ethyl acetate. The organic layer was dried over anhydrous magnesium sulfate, subsequently the solvent was distilled off under reduced pressure, and purification using silica gel column chromatography (hexane:ethyl acetate=3:1) afforded 730.1 mg of the title compound.

$^1$H-NMR (CDCl$_3$); δ (ppm) 2.15 (3H, s), 2.46 (3H, s), 3.63 (2H, brs), 6.61-6.63 (1H, m), 6.67 (1H, s), 6.82-6.85 (1H, m), 6.33 (2H, d, J=8.4 Hz), 7.78 (2H, d, J=8.4 Hz).

MS (ESI); m/z 278 (M+H)$^+$ b) 2-(3,5-Dimethyl-1H-pyrazol-1-yl)-5-methylphenyl 4-methylbenzenesulfonate To 453 mg of 2-amino-5-methylphenyl 4-methylbenzenesulfonate was added 1.6 ml of 5N-hydrochloric acid, and a solution of 146 mg of sodium nitrite dissolved in 1 ml of water was added dropwise at 0° C., followed by stirring for 30 minutes. Then, a solution of 736 mg of stannous chloride dissolved in 0.8 ml of 5N-hydrochloric acid was added dropwise at 0° C., followed by stirring for 1 hour. The solvent was distilled off under reduced pressure and 3.2 ml of ethanol and 167 μl of acetylacetone were added, followed by heating to reflux for 2 hours. To the reaction mixture was added 50 ml of water, followed by neutralizing with saturated sodium hydrogen carbonate solution and extracting with 80 ml of ethyl acetate. The organic layer was dried over anhydrous magnesium sulfate, subsequently the solvent was distilled off under reduced pressure, and purification using silica gel column chromatography (hexane:ethyl acetate=2:1) afforded 199.6 mg of the title compound.

$^1$H-NMR (CDCl$_3$); δ (ppm) 2.09 (3H, s), 2.11 (3H, s), 2.41 (3H,s), 2.43 (3H, s), 5.82 (1H, s), 7.15-7.21 (4H, m), 7.36-7.38 (3H, m).

MS (ESI); m/z 357 (M+H)$^+$ c) 2-(3,5-Dimethyl-1H-pyrazol-1-yl)-5-methylphenol

To 199.6 mg of 2-(3,5-dimethyl-1H-pyrazol-1-yl)-5-methylphenyl 4-methylbenzenesulfonate was added a solution of 314 mg of potassium hydroxide dissolved in 4 ml of ethanol and 4 ml of water, followed by heating to reflux for 1 hour. To the reaction mixture was added 20 ml of water, followed by extracting with 20 ml of ethyl acetate. The organic layer was dried over anhydrous magnesium sulfate, subsequently the solvent was distilled off under reduced pressure, purification was carried out using preparative thin-layer silica gel column chromatography (hexane:ethyl acetate=4:1), the desired fraction was dissolved in 1,4-dioxane, and subsequently lyophilization afforded 66.2 mg of the title compound.

$^1$H-NMR (CDCl$_3$); δ (ppm) 2.29 (3H, s), 2.33 (3H,s), 2.37 (3H,s), 6.01 (1H, s), 6.70 (1H, d, J=8.0 Hz), 6.90 (1H, s), 7.07 (1H, d, J=8.0 Hz), 9.64 (1H, brs).

MS (ESI); m/z 203 (M+H)$^+$

Preparation Example 45

2-(3,5-Dimethyl-1H-pyrazol-1-yl)-5-methoxyphenol a) 2-Amino-5-methoxyphenyl 4-methylbenzenesulfonate 220.1 mg of the title compound was afforded from 176 mg of 2-hydroxy-4-methoxyaniline hydrochloride in a manner similar to Preparation example 44 a).

$^1$H-NMR (CDCl$_3$); δ (ppm) 2.46 (3H, s), 3.62 (3H, s), 6.41 (1H, s), 6.65-6.66 (2H, m), 7.34 (2H, d, J=8.8 Hz), 7.79 (2H, d, J=8.8 Hz).

b) 2-(3,5-Dimethyl-1H-pyrazol-1-yl)-5-methoxyphenyl 4-methylbenzenesulfonate 93.7 mg of the title compound was afforded from 220 mg of 2-amino-5-methoxyphenyl 4-methylbenzenesulfonate in a manner similar to Preparation example 44b).

$^1$H-NMR (CDCl$_3$); δ (ppm) 2.08 (3H, s), 2.11 (3H, s), 2.41 (3H, s), 3.85 (3H, s), 5.82 (1H, s), 6.87 (1H, dd, J=2.4, 8.4 Hz), 7.06 (1H, d, J=2.4 Hz), 7.17 (2H, d, J=8.4 Hz), 7.20-7.24 (1H, m), 7.39 (2H, d, J=8.4 Hz).

MS (ESI); m/z 373 (M+H)$^+$ c) 2-(3,5-Dimethyl-1H-pyrazol-1-yl)-5-methoxyphenol 30.1 mg of the title compound was afforded from 93 mg of 2-(3,5-dimethyl-1H-pyrazol-1-yl)-5-methoxyphenyl 4-methylbenzenesulfonate in a manner similar to Preparation example 44c).

$^1$H-NMR (CDCl$_3$); δ (ppm) 2.27 (3H, s), 2.33 (3H, s), 3.80 (3H, s), 6.00 (1H, s), 6.45 (1H, dd, J=2.8, 8.4 Hz), 6.61 (1H, d, J=2.8 Hz), 7.08 (1H, d, J=8.4 Hz), 9.67 (1H, brs).

MS (ESI); m/z 219 (M+H)$^+$

Preparation Example 46

2-(3,5-Dimethyl-1H-pyrazol-1-yl)-3-methylphenol a) 2-Amino-3-methylphenyl 4-methylbenzenesulfonate 374.1 mg of the title compound was afforded from 200 mg of 2-amino-3-methylphenol in a manner similar to Preparation example 43b).

¹H-NMR (CDCl₃); δ (ppm) 2.14 (3H, s), 2.46 (3H, s), 3.79 (2H,s), 6.51 (1H, t, J=8.0 Hz), 6.63 (1H, d, J=8.0 Hz), 6.91 (1H, d, J=8.0 Hz), 7.32 (2H, d, J=8.4 Hz), 7.78 (2H, d, J=8.4 Hz).

MS (ESI); m/z 278 (M+H)⁺ b) 2-(3,5-Dimethyl-1H-pyrazol-1-yl)-3-methylphenyl 4-methylbenzenesulfonate 269.9 mg of the title compound was afforded from 374 mg of 2-amino-3-methylphenyl 4-methylbenzenesulfonate in a manner similar to Preparation example 43c).

¹H-NMR (CDCl₃); δ (ppm) 2.01 (3H, s), 2.02 (3H, s), 2.16 (3H, s), 2.43 (3H, s), 5.88 (1H, s), 7.19-7.24 (3H, m), 7.32 (2H, d, J=5.2 Hz), 7.51 (2H, d, J=8.4 Hz).

MS (ESI); m/z 357 (M+H)⁺ c) 2-(3,5-Dimethyl-1H-pyrazol-1-yl)-3-methylphenol 79.2 mg of the title compound was afforded from 269 mg of 2-(3,5-dimethyl-1H-pyrazol-1-yl)-3-methylphenyl 4-methylbenzenesulfonate in a manner similar to Preparation example 43d).

¹H-NMR (CD₃OD); δ (ppm) 1.92 (3H, s), 2.01 (3H, s), 2.24 (3H, s), 6.02 (1H, s), 6.79 (2H, d, J=7.6 Hz), 7.18 (1H, t, J=7.6 Hz).

MS (ESI); m/z 203 (M+H)⁺

Preparation Example 47

2-(3,5-Dimethyl-1H-pyrazol-1-yl)-5-hydroxymethylphenol 132 mg of methyl 4-(3,5-dimethyl-1H-pyrazol-1-yl)-3-hydroxybenzenecarboxylate was dissolved in 2.6 ml of tetrahydrofuran and 58 mg of lithium borohydride was added, followed by stirring at 50° C. for 3.5 hours. To the reaction mixture was added 20 ml of water, followed by extracting with 20 ml of ethyl acetate. The organic layer was dried over anhydrous magnesium sulfate, subsequently the solvent was distilled off under reduced pressure, and purification using preparative thin-layer silica gel column chromatography (hexane:ethyl acetate=1:2) afforded 12.4 mg of the title compound.

¹H-NMR (CDCl₃); δ (ppm) 2.28 (3H,s), 2.44 (3H, s), 4.64 (2H, s), 6.02 (1H, s), 6.90 (1H, d, J=8.0 Hz), 7.02 (1H, s), 7.17 (1H, d, J=8.0 Hz).

MS (ESI); m/z 219 (M+H)⁺

Preparation Example 48

2-(3,5-Dimethyl-1H-pyrazol-1-yl)-5-methylaminophenol a) 1-(2-Methoxy-4-nitrophenyl)-3,5-dimethyl-1H-pyrazole 498 mg of the title compound was afforded from 700 mg of 2-methoxy-4-nitroaniline in a manner similar to Preparation example 43c).

¹H-NMR (CDCl₃); δ (ppm) 2.13 (3H, s), 2.30 (3H, s), 3.93 (3H, s), 6.02 (1H, s), 7.53 (1H, d, J=8.4 Hz), 7.89 (1H, d, J=2.0 Hz), 7.95 (1H, dd, J=2.0, 8.4 Hz).

MS (ESI); m/z 248 (M+H)⁺ b) 4-(3,5-Dimethyl-1H-pyrazol-1-yl)-3-methoxyaniline 417.6 mg of the title compound was afforded from 495 mg of 1-(2-methoxy-4-nitrophenyl)-3,5-dimethyl-1H-pyrazole in a manner similar to Preparation example 31. ¹H-NMR (CDCl₃); δ (ppm) 2.06 (3H, s), 2.28 (3H, s), 3.72 (3H, s), 3.81 (2H, brs), 5.92 (1H, s), 6.28-6.31 (2H, m), 7.06 (1H, d, J=8.4 Hz).

MS (ESI); m/z 218 (M+H)⁺ c) 4-(3,5-Dimethyl-1H-pyrazol-1-yl)-3-methoxy-N-methylaniline 200 mg of 4-(3,5-dimethyl-1H-pyrazol-1-yl)-3-methoxyaniline was dissolved in 6 ml of dimethylformamide, and 160 μl of methyl iodide and 636 mg of potassium carbonate were added, followed by stirring at room temperature for 2.5 hours. To the reaction mixture was added 50 ml of water, followed by extracting with 50 ml of ethyl acetate. The organic layer was dried over anhydrous magnesium sulfate, subsequently the solvent was distilled off under reduced pressure, and purification using preparative thin-layer silica gel column chromatography (hexane:ethyl acetate=1:3) afforded 48.7 mg of the title compound.

¹H-NMR (CDCl₃); δ (ppm) 2.07 (3H, s), 2.28 (3H, s), 2.86 (3H, s), 3.74 (3H, s), 3.95 (1H, brs), 5.92 (1H, s), 6.17 (1H, d, J=2.4 Hz), 6.21 (1H, dd, J=2.4, 8.4 Hz), 7.09 (1H, d, J=8.4 Hz).

MS (ESI); m/z 232 (M+H)⁺ d) 2-(3,5-Dimethyl-1H-pyrazol-1-yl)-5-methylaminophenol 25 mg of the title compound was afforded from 58.7 mg of 4-(3,5-dimethyl-1H-pyrazol-1-yl)-3-methoxy-N-methylaniline in a manner similar to Preparation example 33c).

¹H-NMR (CDCl₃); δ (ppm) 2.28 (3H, s), 2.32 (3H, s), 2.83 (3H, d, J=1.2 Hz), 5.98 (1H, s), 6.13-6.16 (1H, m), 6.31-6.32 (1H, m), 6.99 (1H, dd, J=1.2, 8.4 Hz).

MS (ESI); m/z 218 (M+H)⁺

Preparation Example 49

2-(3,5-Dimethyl-1H-pyrazol-1-yl)-4-methylphenol a) 2-Amino-4-methylphenyl 4-methylbenzenesulfonate 770.1 mg of the title compound was afforded from 479 mg of 2-amino-4-methylphenol hydrochloride in a manner similar to Preparation example 43b).

¹H-NMR (CDCl₃); δ (ppm) 2.21 (3H, s), 2.46 (3H, s), 3.74 (2H, brs), 6.39 (1H, d, J=8.0 Hz), 6.53 (1H, s), 6.62 (1H, d, J=8.0 Hz), 7.32 (2H, d, J=8.0 Hz), 7.77 (2H, d, J=8.0 Hz).

MS (ESI); m/z 278 (M+H)⁺ b) 2-(3,5-Dimethyl-1H-pyrazol-1-yl)-4-methylphenyl 4-methylbenzenesulfonate 137.3 mg of the title compound was afforded from 400 mg of 2-amino-4-methylphenyl 4-methylbenzenesulfonate in a manner similar to Preparation example 43c).

¹H-NMR (CDCl₃); δ (ppm) 2.10 (3H, s), 2.12 (3H, s), 2.35 (3H, s), 2.41 (3H, s), 5.82 (1H, s), 7.13-7.15 (3H, m), 7.20-7.22 (1H, m), 7.33-7.36 (2H, m), 7.42 (2H, d, J=8.4 Hz).

MS (ESI); m/z 357 (M+H)⁺ c) 2-(3,5-Dimethyl-1H-pyrazol-1-yl)-4-methylphenol 60.4 mg of the title compound was afforded from 167 mg of 2-(3,5-dimethyl-1H-pyrazol-1-yl)-4-methylphenyl 4-methylbenzenesulfonate in a manner similar to Preparation example 43d).

¹H-NMR (CDCl₃); δ (ppm) 2.29 (3H, s), 2.31 (3H, s), 2.39 (3H, s), 6.02 (1H, s), 6.97-7.02 (3H, m), 9.43 (1H, s).

MS (ESI); m/z 203 (M+H)⁺

Preparation Example 50

2-(3,5-Dimethyl-1H-pyrazol-1-yl)-5-trifluoromethylphenol a) 1-(2-Methoxy-4-(trifluoromethylphenyl)-3,5-dimethyl-1H-pyrazole 95.5 mg of the title compound was afforded from 191 mg of 2-methoxy-4-trifluoromethylaniline in a manner similar to Preparation example 43c).

$^1$H-NMR (CDCl$_3$); δ (ppm) 2.05 (3H,s), 2.30 (3H, s), 3.86 (3H, s), 5.99 (1H,s), 7.22 (1H,s), 7.31 (1H, d, J=8.0 Hz), 7.46 (1H, d, J=8.0 Hz).

MS (ESI); m/z 271 (M+H)$^+$ b) 2-(3,5-Dimethyl-1H-pyrazol-1-yl)-5-trifluoromethylphenol 25.7 mg of the title compound was afforded from 95.5 mg of 1-(2-methoxy-4-trifluoromethylphenyl)-3,5-dimethyl-1H-pyrazole in a manner similar to Preparation example 33c).

$^1$H-NMR (CDCl$_3$); δ (ppm) 2.31 (3H, s), 2.45 (3H, s), 6.08 (1H,s), 7.15-7.18 (1H, m), 7.30-7.35 (2H, m), 10.64 (1H,s).

MS (ESI); m/z 257 (M+H)$^+$

Preparation Example 51

2-(3,5-Dimethyl-1H-pyrazol-1-yl)-6-methylphenol a) 2-Amino-6-methylphenyl 4-methylbenzenesulfonate 159.9 mg of the title compound was afforded from 200 mg of 6-amino-o-cresol hydrochloride in a manner similar to Preparation example 43b).

$^1$H-NMR (CDCl$_3$); δ (ppm) 2.06 (3H, s), 2.48 (3H, s), 3.96 (2H, s), 6.53-6.55 (1H, m), 6.59-6.61 (1H, m), 6.93 (1H, t, J=7.6 Hz), 7.37 (2H, d, J=8.0 Hz), 7.90 (2H, d, J=8.0 Hz).

MS (ESI); m/z 278 (M+H)$^+$ b) 2-(3,5-Dimethyl-1H-pyrazol-1-yl)-6-methylphenyl 4-methylbenzenesulfonate 48.8 mg of the title compound was afforded from 159.5 mg of 2-amino-6-methylphenyl 4-methylbenzenesulfonate in a manner similar to Preparation example 43c).

$^1$H-NMR (CDCl$_3$); δ (ppm) 2.09 (3H, s), 2.10 (3H, s), 2.43 (3H, s), 2.49 (3H, s), 5.67 (1H, s), 7.13-7.32 (5H, m), 7.48 (2H, d, J=8.0 Hz).

MS (ESI); m/z 357 (M+H)$^+$ c) 2-(3,5-Dimethyl-1H-pyrazol-1-yl)-6-methylphenol 12 mg of the title compound was afforded from 48.5 mg of 2-(3,5-dimethyl-1H-pyrazol-1-yl)-6-methylphenyl 4-methylbenzenesulfonate in a manner similar to Preparation example 43d).

$^1$H-NMR (CDCl$_3$); δ (ppm) 2.30 (3H, s), 2.31 (3H, s), 2.38 (3H, s), 6.03 (1H, s), 6.81 (1H, t, J=8.0 Hz), 7.03-7.09 (2H, m), 9.79 (1H, s).

MS (ESI); m/z 203 (M+H)$^+$

Preparation Example 52

2-(3,5-Dimethyl-1H-pyrazol-1-yl)-5-ethylphenol a) 4-Chloro-5-ethyl-2-nitrophenyl methanesulfonate 150 mg of 4-chloro-5-ethyl-2-nitrophenol was dissolved in 1.5 ml of dichloromethane, and 156 μl of triethylamine and 69 μl of methanesulfonyl chloride were added, followed by stirring at room temperature for 30 minutes. To the reaction mixture was added 50 ml of water, followed by extracting with 60 ml of ethyl acetate. The organic layer was dried over anhydrous magnesium sulfate, and subsequently the solvent was distilled off under reduced pressure to afford 200.7 mg of the title compound.

$^1$H-NMR (CDCl$_3$); δ (ppm) 1.28 (3H, t, J=7.6 Hz), 2.83 (2H, q, J=7.6 Hz), 3.37 (3H, s), 7.42 (1H, s), 8.09 (1H, s).

b) 2-Amino-5-ethylphenyl methanesulfonate 200 mg of 4-chloro-5-ethyl-2-nitrophenyl methanesulfonate was dissolved in 4 ml of ethanol and 200 mg of 10% palladium/carbon was added, followed by stirring under a hydrogen atmosphere at room temperature for 4 hours. The insoluble material was filtered, and subsequently the solvent was distilled off under reduced pressure to afford 74.9 mg of the title compound.

$^1$H NMR (CD$_3$OD); δ (ppm) 1.26 (3H, t, J=7.6 Hz), 2.73 (2H, q, J=7.6 Hz), 3.47 (3H, s), 7.28-7.46 (3H, m).

MS (ESI); m/z 216 (M+H)$^+$ c) 2-(3,5-Dimethyl-1H-pyrazol-1-yl)-5-ethylphenyl methanesulfonate 28.1 mg of the title compound was afforded from 74.5 mg of 2-amino-5-ethylphenyl methanesulfonate in a manner similar to Preparation example 43c).

$^1$H-NMR (CDCl$_3$); δ (ppm) 1.28 (3H, t, J=7.6 Hz), 2.17 (3H, s), 2.26 (3H, s), 2.65 (3H, s), 2.73 (2H, q, J=7.6 Hz), 6.00 (1H, s), 7.24-7.26 (1H, m), 7.33-7.37 (2H, m).

MS (ESI); m/z 295 (M+H)$^+$ d) 2-(3,5-Dimethyl-1H-pyrazol-1-yl)-5-ethylphenol 28 mg of 2-(3,5-dimethyl-1H-pyrazol-1-yl)-5-ethylphenyl methanesulfonate was dissolved in 0.1 ml of methanol and 0.07 ml of 5N-hydrochloric acid was added, followed by heating to reflux for 30 minutes. To the reaction mixture was added 15 ml of water, followed by extracting with 15 ml of ethyl acetate. The organic layer was dried over anhydrous magnesium sulfate, subsequently the solvent was distilled off under reduced pressure, and purification using preparative thin-layer silica gel column chromatography (hexane:ethyl acetate=4:1) afforded 7.4 mg of the title compound.

$^1$H NMR (CDCl$_3$); δ (ppm) 1.24 (3H, t, J=7.6 Hz), 2.29 (3H, s), 2.38 (3H, s), 2.63 (2H, q, J=7.6 Hz), 6.02 (1H, s), 6.73-6.75 (1H, m), 6.94 (1H, s), 7.10 (1H, d, J=8.0 Hz), 9.67 (1H, s).

MS (ESI); m/z 217 (M+H)$^+$

Preparation Example 53

2-(4-Fluoro-3,5-dimethyl-1H-pyrazol-1-yl)phenol a) 1-(2-Benzyloxyphenyl)-4-fluoro-3,5-dimethyl-1H-pyrazole 500 mg of 2-benzyloxyphenylhydrazine hydrochloride and 251 mg of 3-fluoropentane-2,4-dione were added to 12 ml of ethanol, followed by heating to reflux for 1.5 hours. The reaction solution was concentrated under reduced pressure as such, and purification using silica gel column chromatography (hexane:ethyl acetate=6:1-5:1) afforded 417 mg of the title compound.

$^1$H-NMR (CDCl$_3$); δ (ppm) 2.07 (3H, s), 2.30 (3H, s), 5.04 (2H, s), 7.03-7.07 (2H, m), 7.24-7.37 (7H, m).

MS (ESI); m/z 297 (M+H)$^+$ b) 2-(4-Fluoro-3,5-dimethyl-1H-pyrazol-1-yl)phenol 416 mg of 1-(2-benzyloxyphenyl)-4-fluoro-3,5-dimethyl-1H-pyrazole was dissolved in 16 ml of methanol and 42.6 mg of 10% palladium/carbon was added, followed by stirring under a hydrogen atmosphere at room temperature for 24 hours. The insoluble material was filtered, subsequently the filtrate was distilled off under reduced pressure, and the resulting residue was purified using silica gel column chromatography (hexane:ethyl acetate=5:1) to give 290 mg of the title compound.

1H-NMR (CDCl$_3$); δ (ppm) 2.28 (3H, s), 2.33 (3H, s), 6.90 (1H, t, J=8.0 Hz), 7.06 (1H, d, J=8.0 Hz), 7.15 (1H, d, J=8.0 Hz), 7.19 (1H, t, J=8.0 Hz).

MS (ESI); m/z 207 (M+H)$^+$

Preparation Example 54

5-Bromo-2-(3,5-dimethyl-1H-pyrazol-1-yl)phenol a) 5-Bromo-2-hydrazinylphenol 4-methylbenzenesulfonate 1.0 g of 2-amino-5-bromophenol was suspended in 7 ml of ethanol and 1.5 ml of concentrated hydrochloric acid was added dropwise at −10° C. Furthermore, 636 mg of tert-butyl nitrite was added dropwise at the same temperature, followed by stirring at the same temperature for 1 hour to afford a diazonium salt solution. Another flask was charged with 2.49 g of stannous chloride dihydrate, 1.08 g of p-toluenesulfonic acid monohydrate and 15 ml of ethanol, followed by stirring at −10° C. for 15 minutes. Into this solution was added dropwise the above prepared diazonium salt solution at −10° C., followed by stirring at the same temperature for 1 hour. 30 ml of tert-butyl methylether was added, followed by stirring for 15 minutes. Subsequently, the resulting precipitate was filtered off to afford 0.9 g of the title compound.

b) 5-Bromo-2-(3,5-dimethyl-1H-pyrazol-1-yl)phenol 0.9 g of 5-bromo-2-hydrazinylphenol 4-methylbenzenesulfonate and 0.8 g of acetylacetone were added into 25 ml of ethanol, followed by heating to reflux for 1 hour. The reaction was cooled to room temperature and concentrated under reduced pressure as such, and the resulting residue was dissolved in 50 ml of ethyl acetate, followed by washing twice with 20 ml of saturated aqueous sodium bicarbonate. The organic layer was dehydrated with anhydrous sodium sulphate and subsequently concentrated under reduced pressure, and the resulting residue was purified by silica gel column chromatography (hexane:ethyl acetate=4:1) to afford 650 mg of the title compound.

1H-NMR (CDCl$_3$); δ (ppm) 2.30 (3H, s), 2.40 (3H, s), 6.05 (1H, s), 7.01-7.08 (2H, m), 7.26 (1H, s).

MS (ESI); m/z 267 (M+H)$^+$

Preparation Example 55

5-Bromo-2-(4-chloro-3,5-dimethyl-1H-pyrazol-1-yl)phenol 558 mg of the title compound was afforded from 0.9 g of 5-bromo-2-hydrazinylphenol 4-methylbenzenesulfonate prepared in analogy to Preparation example 54a) and 1.07 g of 3-chloropentane-2,4-dione in a manner similar to Preparation example 54b).

1H-NMR (CDCl$_3$); δ (ppm) 2.30 (3H, s), 2.38 (3H, s), 7.02-7.08 (2H, m), 7.27 (1H, d, J=2.0 Hz), 9.62 (1H, s).

MS (ESI); m/z 303 (M+H)$^+$

Preparation Example 56

5-Bromo-2-(3,4,5-trimethyl-1H-pyrazol-1-yl)phenol 320 mg of the title compound was afforded from 0.9 g of 5-bromo-2-hydrazinylphenol 4-methylbenzenesulfonate prepared in analogy to Preparation example 54a) and 0.9 g of 3-methylpentane-2,4-dione in a manner similar to Preparation example 54b).

1H-NMR (CDCl$_3$); δ (ppm) 1.98 (3H, s), 2.24 (3H, s), 2.31 (3H, s), 7.00-7.06 (2H, m), 7.25 (1H, d, J=1.6 Hz)), 10.34 (1H, s).

MS (ESI); m/z 281 (M+H)$^+$

Preparation Example 57

4-(3,5-Dimethyl-1H-pyrazol-1-yl)-3-hydroxyphenyl acetate a) 4-Nitro-1,3-phenylene diacetate Under a nitrogen atmosphere, 5.0 g of 4-nitrobenzene-1,3-diol was dissolved in 50 ml of methylene chloride, and under ice cooling, 5.35 g of pyridine, 0.39 g of 4-dimethylaminopyridine and 8.12 g of acetic anhydride were sequentially added. The temperature of the reaction was raised to room temperature, followed by stirring for 1 hour. The reaction solution was washed with 50 ml of water, 100 ml of 1N-hydrochloric acid, 100 ml of saturated aqueous sodium bicarbonate, and 100 ml of saturated brine sequentially, dehydrated with anhydrous sodium sulphate, and subsequently concentrated under reduced pressure to afford 7.4 g of the title compound. 1H-NMR (CDCl$_3$); δ (ppm) 2.33 (3H, s), 2.37 (3H, s), 7.09 (1H, d, J=2.4 Hz), 7.18 (1H, dd, J=2.4, 9.2 Hz), 8.16 (1H, d, J=9.2 Hz).

b) 3-Hydroxy-4-nitrophenyl acetate

Under a nitrogen atmosphere, 1.0 g of 4-nitro-1,3-phenylene diacetate was dissolved in 25 ml of chloroform, and under ice cooling, 2.23 g of aluminium chloride was added. The temperature of the reaction was raised to room temperature, followed by stirring for 3 hours. 100 ml of water was added, followed by extracting three times with 30 ml of methylene chloride. The organic layers were combined, washed with 25 ml of 1N-hydrochloric acid and 25 ml of saturated brine sequentially, dehydrated with anhydrous sodium sulphate, and subsequently concentrated under reduced pressure. The resulting residue was purified by silica gel column chromatography (hexane:ethyl acetate=20:1) to afford 610 mg of the title compound.

1H-NMR (CDCl$_3$): δ (ppm) 2.32 (3H, s), 6.77 (1H, dd, J=2.4 Hz, J=9.2 Hz), 6.95 (1H, d, J=2.4 Hz), 8.14 (1H, d, J=9.2 Hz), 10.70 (1H, s).

MS (ESI); m/z 196 (M−H)$^-$ c) 4-Amino-3-hydroxyphenyl acetate 3.0 g of 3-hydroxy-4-nitrophenyl acetate was dissolved in 50 ml of ethyl acetate and 300 mg of 10% palladium/carbon was added, followed by stirring under a hydrogen atmosphere at room temperature for 10 hours. The insoluble material was filtered, subsequently the filtrate was distilled off under reduced pressure, and the resulting residue was purified by silica gel column chromatography (hexane:ethyl acetate=1:1) to afford 2.48 g of the title compound.

1H-NMR (DMSO-d6); δ (ppm) 2.17 (3H, s), 4.45 (2H, brs), 6.28 (1H, dd, J=2.4, 8.4 Hz), 6.40 (1H, d, J=2.4 Hz), 6.53 (1H, d, J=8.4 Hz), 9.26 (1H, brs).

MS (ESI); m/z 167 (M+)

d) 4-(3,5-Dimethyl-1H-pyrazol-1-yl)-3-hydroxyphenyl acetate 330 mg of the title compound was afforded from 0.9 g of 4-hydrazinyl-3-hydroxyphenyl acetate 4-methylbenzenesulfonate prepared using 1.0 g of 4-amino-3-hydroxyphenyl acetate in analogy to Preparation example 54a) and 0.9 g of acetylacetone, in a manner similar to Preparation example 54b).

1H-NMR (CDCl$_3$); δ (ppm) 2.29 (3H, s), 2.30 (3H, s), 2.41 (3H, s), 6.04 (1H, s), 6.68 (1H, dd, J=2.4, 8.8 Hz), 6.85 (1H, d, J=2.4 Hz), 7.19 (1H, d, J=8.8 Hz), 10.14 (1H, s).
MS (ESI); m/z 247 (M+H)$^+$ Preparation Example 58

4-(4-Chloro-3,5-dimethyl-1H-pyrazol-1-yl)-3-hydroxyphenyl acetate 30 mg of the title compound was afforded from 0.9 g of 4-hydrazinyl-3-hydroxyphenyl acetate 4-methylbenzenesulfonate prepared using 1.0 g of 4-amino-3-hydroxyphenyl acetate in analogy to Preparation example 54a) and 1.2 g of 3-chloropentane-2,4-dione, in a manner similar to Preparation example 54b).

1H-NMR (CDCl$_3$); δ (ppm) 2.30 (3H, s), 2.31 (3H, s), 2.39 (3H, s), 6.70 (1H, dd, J=2.8, 8.8 Hz), 6.86 (1H, d, J=2.8 Hz), 7.17 (1H, d, J=8.8 Hz), 9.50 (1H, s).
MS (ESI); m/z 281 (M+H)$^+$ Preparation Example 59

3-Hydroxy-4-(3,4,5-trimethyl-1H-pyrazol-1-yl)phenyl acetate 230 mg of the title compound was afforded from 0.6 g of 4-hydrazinyl-3-hydroxyphenyl acetate 4-methylbenzenesulfonate prepared using 1.0 g of 4-amino-3-hydroxyphenyl acetate in analogy to Preparation example 54a) and 1.0 g of 3-methylpentane-2,4-dione, in a manner similar to Preparation example 54b). 1H-NMR (CDCl$_3$); δ (ppm) 1.99 (3H, s), 2.24 (3H, s), 2.30 (3H, s), 2.32 (3H, s), 6.66 (1H, dd, J=2.8, 8.4 Hz), 6.83 (1H, d, J=2.8 Hz), 7.17 (1H, d, J=8.4 Hz), 10.22 (1H, s).
MS (ESI); m/z 261 (M+H)$^+$ Preparation Example 60

2-(3,5-Dimethyl-1H-pyrazol-1-yl)-4-methoxy-5-methylphenol a) 1,4-Dimethoxy-2-methyl-5-nitrobenzene 6.0 g of 2,5-dimethoxytoluene was dissolved in 20 ml of acetic acid, and at 40° C., a solution of 4.32 g of fuming nitric acid (d=1.50) in 10 ml of acetic acid was added dropwise over 5 minutes. The reaction was stirred at the same temperature for 30 minutes, cooled to room temperature, and subsequently stirred for another 30 minutes. The reaction solution was diluted with 300 ml of cold water, and the resulting precipitate was filtering off and washed with 100 ml of cold water. Drying under reduced pressure gave 7.5 g of the title compound. 1H-NMR (CDCl$_3$); δ (ppm) 2.28 (3H, s), 3.84 (3H, s), 3.92 (3H, s), 6.90 (1H, s), 7.40 (1H, s).
MS (ESI); m/z 198 (M+H)$^+$ b) 4-Methoxy-5-methyl-2-nitrophenol A solution of 6.0 g of 1,4-dimethoxy-2-methyl-5-nitrobenzene in 30 ml of methylene chloride was cooled to −20° C. and 30 ml of 1M solution of boron trichloride in methylene chloride was added dropwise at the same temperature. The temperature of the reaction was raised to room temperature and subsequently the reaction solution was stirred for 16 hours and added to 50 ml of saturated aqueous sodium bicarbonate, followed by extracting three times with 100 ml of ethyl acetate. The organic layers were combined, washed with 100 ml of water and 50 ml of saturated brine, subsequently dehydrated with anhydrous sodium sulphate, and concentrated under reduced pressure. The resulting residue was purified by silica gel column chromatography (hexane:ethyl acetate=9:1) to afford 4.25 g of the title compound.

1H-NMR (CDCl$_3$); δ (ppm) 2.26 (3H, s), 3.84 (3H, s), 6.94 (1H, s), 7.39 (1H, s), 10.46 (1H, s).
MS (ESI); m/z 182 (M−H)$^-$ c) 4-Methoxy-5-methyl-2-nitrophenyl 4-methylbenzenesulfonate Under a nitrogen atmosphere, to a solution of 8.0 g of 4-methoxy-5-methyl-2-nitrophenol in 80 ml of methylene chloride was added 9.15 g of p-toluenesulfonyl chloride at room temperature, followed by cooling to 0° C. 4.86 g of triethylamine was added thereto, followed by stirring for 2 hours. The reaction solution was poured to 150 ml of water, followed by extracting with 150 ml of methylene chloride. The organic layer was washed with 100 ml of water and 50 ml of saturated brine, dehydrated with anhydrous sodium sulphate, and subsequently concentrated under reduced pressure. The resulting residue was purified by silica gel column chromatography (hexane:ethyl acetate=9:1) to afford 12.0 g of the title compound.

1H-NMR (CDCl$_3$); δ (ppm) 2.26 (3H, s), 2.46 (3H, s), 3.87 (3H, s), 7.19 (1H, s), 7.33 (1H, s), 7.34 (2H, d, J=8.4 Hz), 7.77 (2H, d, J=8.4 Hz).
MS (ESI); m/z 336 (M−H)$^-$ d) 2-Amino-4-methoxy-5-methylphenyl 4-methylbenzenesulfonate 3.2 g of the title compound was afforded in a manner similar to Preparation example 57c) using 4.0 g of 4-methoxy-5-methyl-2-nitrophenyl 4-methylbenzenesulfonate.

1H-NMR (DMSO-d6); δ (ppm) 1.91 (3H, s), 2.41 (3H, s), 3.64 (3H, s), 4.73 (2H, brs), 6.25 (1H, s), 6.64 (1H, s), 7.43 (2H, d, J=8.4 Hz), 7.79 (2H, d, J=8.4 Hz).
MS (ESI); m/z 308 (M+H)$^+$ e) 2-(3,5-Dimethyl-1H-pyrazol-1-yl)-4-methoxy-5-methylphenyl 4-methylbenzenesulfonate 400 mg of the title compound was afforded in a manner similar to Preparation examples 54a) and 54b) using 1.0 g of 2-amino-4-methoxy-5-methylphenyl 4-methylbenzenesulfonate.

1H-NMR (CDCl$_3$); δ (ppm) 2.10 (6H, s), 2.25 (3H, s), 2.41 (3H, s), 3.79 (3H, s), 5.80 (1H, s), 6.71 (1H, s), 7.15 (2H, d, J=8.4 Hz), 7.27 (1H, s), 7.35 (2H, d, J=8.4 Hz).
MS (ESI); m/z 387 (M+H)$^+$ f) 2-(3,5-Dimethyl-1H-pyrazol-1-yl)-4-methoxy-5-methylphenol 70 mg of the title compound was afforded in a manner similar to Preparation example 29 using 200 mg of 2-(3,5-dimethyl-1H-pyrazol-1-yl)-4-methoxy-5-methylphenyl 4-methylbenzenesulfonate.

1H-NMR (CDCl$_3$); δ (ppm) 2.21 (3H, s), 2.29 (3H, s), 2.39 (3H, s), 3.78 (3H, s), 6.02 (1H, s), 6.67 (1H, s), 6.89 (1H, s), 8.87 (1H, s).
MS (ESI); m/z 233 (M+H)+

Preparation Example 61

4-Chloro-2-(3,5-dimethyl-1H-pyrazol-1-yl)-5-methylphenol a) 2-Amino-4-chloro-5-methylphenol Into a solution of 5.0 g of 4-chloro-5-methyl-2-nitrophenol in 100 ml of methanol were added 8.71 g of zinc dust activated by hydrochloric acid and a solution of 7.1 g of ammonium chloride in 20 ml of water at 0° C. This suspension was stirred at room temperature for 4 hours and subsequently the insoluble material was filtered through Celite, followed by washing with 100 ml of ethyl acetate. The filtrate and washings were combined and concentrated under reduced pressure. The resulting residue was purified by silica gel column chromatography (hexane:ethyl acetate=3:2) to afford 1.4 g of the title compound.

1H-NMR (DMSO-d6); δ (ppm) 2.10 (3H, s), 4.57 (2H, brs), 6.54 (1H, s), 6.58 (1H, s), 9.11 (1H, s).

MS (ESI); m/z 157 (M)$^+$ b) 4-Chloro-2-(3,5-dimethyl-1H-pyrazol-1-yl)-5-methylphenol 120 mg of the title compound was afforded using 1.0 g of 2-amino-4-chloro-5-methylphenol in a manner similar to Preparation examples 54a) and 54b).

1H-NMR (CDCl$_3$); δ (ppm) 2.29 (3H, s), 2.34 (3H, s), 2.41 (3H, s), 6.03 (1H, s), 6.96 (1H, s), 7.19 (1H, s), 9.88 (1H, s).

MS (ESI); m/z 237 (M+H)$^+$

Preparation Example 62

2-(3,5-Dimethyl-1H-pyrazol-1-yl)-4,5-dimethylphenol 630 mg of the title compound was afforded using 1.0 g of 2-amino-4,5-dimethylphenol in a manner similar to Preparation examples Ma) and 54b).

1H-NMR (CDCl$_3$); δ (ppm) 2.21 (3H, s), 2.24 (3H, s), 2.29 (3H, s), 2.38 (3H, s), 6.00 (1H, s), 6.88 (1H, s), 6.94 (1H, s), 9.28 (1H, s).

MS (ESI); m/z 217 (M+H)$^+$

Preparation Example 63

4-(4-Chloro-3,5-dimethyl-1H-pyrazol-1-yl)-benzene-1,3-diol 200 mg of the title compound was afforded as a by-product during the silica gel column chromatography purification in Preparation example 58.

1H-NMR (CD$_3$OD); δ (ppm) 2.07 (3H, s), 2.20 (3H, s), 6.36 (1H, dd, J=2.4, 8.4 Hz), 6.42 (1H, d, J=2.4 Hz), 6.98 (1H, d, J=8.4 Hz).

MS (ESI); m/z 239 (M+H)$^+$

2. Preparation Example of a Pressure Sensitive Adhesive in the Patch of the Present Invention Preparation examples of the various kinds of pressure sensitive adhesives to be used in the patch of the present invention are shown below. Incidentally, all "%" and "parts" mean "% by mass" and "part by mass", respectively.

Pressure Sensitive Adhesive Preparation Example 1

Acrylic-Based Pressure Sensitive Adhesive A

99% of 2-ethylhexyl acrylate and 1% of acrylic acid were polymerized according to a conventional solution polymerization method using 0.5 part of lauroyl peroxide as a polymerization initiator in ethyl acetate at a concentration of 50% to obtain Acrylic-based pressure sensitive adhesive A.

Pressure Sensitive Adhesive Preparation Example 2

Acrylic-Based Pressure Sensitive Adhesive B

96% of 2-ethylhexyl acrylate and 4% of acrylic acid were polymerized according to a conventional solution polymerization method using 0.5 part of lauroyl peroxide as a polymerization initiator in ethyl acetate at a concentration of 50% to obtain Acrylic-based pressure sensitive adhesive B.

Pressure Sensitive Adhesive Preparation Example 3

Acrylic-Based Pressure Sensitive Adhesive C

92% of 2-ethylhexyl acrylate and 8% of acrylic acid were polymerized according to a conventional solution polymerization method using 0.5 part of lauroyl peroxide as a polymerization initiator in ethyl acetate at a concentration of 50% to obtain Acrylic-based pressure sensitive adhesive C.

Pressure Sensitive Adhesive Preparation Example 4

Acrylic-Based Pressure Sensitive Adhesive D a 2-ethylhexyl acrylate. N-vinylpyrrolidone copolymer solution (product listed in Japanese Pharmaceutical Excipients) was adjusted to 35% of solid content concentration in ethyl acetate to obtain Acrylic-based pressure sensitive adhesive.

Pressure Sensitive Adhesive Preparation Example 5

Acrylic-Based Pressure Sensitive Adhesive E

By using 99.5% of a mixture comprising 2-ethylhexyl acrylate, 2-ethylhexyl methacrylate and dodecyl methacrylate with a molar ratio of 1:8:1, and 0.5% of lauroyl peroxide as a polymerization initiator, the resulting mixture was polymerized according to a conventional solution polymerization method in ethyl acetate at a concentration of 35% to obtain Acrylic-based pressure sensitive adhesive E.

Pressure Sensitive Adhesive Preparation Example 6

Acrylic-Based Pressure Sensitive Adhesive F

Non-functional acrylic-based pressure sensitive adhesive GMS3253 (Cytec)

Pressure Sensitive Adhesive Preparation Example 7

Acrylic-Based Pressure Sensitive Adhesive G

Hydroxy functional acrylic-based pressure sensitive adhesive GMS7883 (Cytec)

Pressure Sensitive Adhesive Preparation Example 8

Acrylic-Based Pressure Sensitive Adhesive H

Carboxylic acid functional acrylic-based pressure sensitive adhesive GMS9083 (Cytec)

Pressure Sensitive Adhesive Preparation Example 9

Acrylic-Based Pressure Sensitive Adhesive I carboxylic acid functional acrylic-based pressure sensitive adhesive GMS9073 (Cytec)

Pressure Sensitive Adhesive Preparation Example 10

Silicone-Based Pressure Sensitive Adhesive silicone-based pressure sensitive adhesive Bio-PSA 7-4501 (TORAY DOW CORNING Corp.)

Pressure Sensitive Adhesive Preparation Example 11

Rubber-Based Pressure Sensitive Adhesive A

By using 50% of a styrene-isoprene-styrene block copolymer (SIS5002, JSR) and 50% of a hydrogenated rosin ester resin (Pine Crystal KE-311, ARAKAWA CHEMICAL INDUSTRIES, LTD.), a toluene/hexane (mixture ratio: 2/1) solution thereof was so prepared that the solid component concentration of the solution became 40%, and the mixture was stirred until the solution became uniform to obtain rubber-based pressure sensitive adhesive A.

Pressure Sensitive Adhesive Preparation Example 12

Rubber-Based Pressure Sensitive Adhesive B

By using 50% of a styrene-isoprene-styrene block copolymer (SIS5002, JSR) and 50% of a terpene resin (YS resin PX1150N, YASUHARA CHEMICAL CO., LTD.), a toluene/hexane (mixture ratio: 2/1) solution thereof was so prepared that the solid component concentration of the solution became 40%, and the mixture was stirred until the solution became uniform to obtain rubber-based pressure sensitive adhesive B.

Pressure Sensitive Adhesive Preparation Example 13

Urethane-Based Pressure Sensitive Adhesive

Toluene and ethyl acetate were added to 43% of a polyether polyol (1) (copolymer of ethylene oxide unit and propyleneoxide unit using glycerine as an initiator, number average molecular weight: 10,000, number of average functional group(s): 3), 21% of a polyether polyol (2) (copolymer of propylene oxide units, number average molecular weight: 10,000, number of average functional group(s): 2), and 36% of a polyether monool (polymer of propylene oxide units using methanol as an initiator, number average molecular weight: 3,500, number of average functional group(s): 1), to adjust the solid component to 50%, then, 0.02% of dibutyl tin dilaurate was added as the urethanization catalyst to the above-mentioned solid component, and hexamethylene diisocyanate prepolymer (weight average molecular weight: 600, number of average functional group(s): 2) was added as the organic diisocyanate so that a molar ratio thereof become 90 of the isocyanate group in the isocyanate prepolymer based on 100 of the hydroxyl group in the active hydrogen compound to obtain Urethane-based pressure sensitive adhesive.

3. Preparation Example of the Patch of the Present Invention

Preparation Examples of Patches 1 to 33 Using Acrylic-Based Pressure Sensitive Adhesives After weighing 2-(3,5-dimethyl-1H-pyrazol-1-yl)-5-methylphenol (hereinafter referred to as the compound of Preparation example 44) prepared in Preparation example 44, and Acrylic-based pressure sensitive adhesives A to I (weight as solid component) prepared in Pressure sensitive adhesive preparation examples 1 to 9, the whole solid component was adjusted to 35% in ethyl acetate, and the mixture was stirred until it became uniform. The pressure sensitive adhesive solution was applied onto a 75 µm PET (polyethyleneterephthalate) film (FILMBYNA 75E-0010BD, FUJIMORI KOGYO CO., LTD.) one surface of which had been subjected to silicone-treatment so that a thickness of the pressure sensitive adhesive layer after drying became 70 µm, and dried at 85° C. for 3 minutes. Then, one surface of the pressure sensitive adhesive layer was laminated with a 12 µm PET film (Lumirror S10, Toray Industries, Inc.) to obtain a patch using acrylic-based pressure sensitive adhesive.

Preparation Examples of Patches 34 and 35 Using Silicone-Based Pressure Sensitive Adhesives In the same manner as in Preparation example of the patches using the above-mentioned acrylic-based pressure sensitive adhesive except that Acrylic-based pressure sensitive adhesive A was changed to Silicone-based pressure sensitive adhesive prepared in pressure sensitive adhesive preparation example 10, and the concentration of the whole solid components was adjusted to 65% in ethyl acetate to obtain a patch using silicone-based pressure sensitive adhesive.

Preparation Examples of Patches 36 and 37 Using Rubber-Based Pressure Sensitive Adhesives In the same manner as in Preparation example of the patches using the above-mentioned acrylic-based pressure sensitive adhesive except that Acrylic-based pressure sensitive adhesive A was changed to Rubber-based pressure sensitive adhesive A or B prepared in Pressure sensitive adhesive preparation examples 11 and 12, dibutylhydroxytoluene (SWANOX BHT, Seiko Chemical Co., Ltd.) (1% based on the whole solid components) was added as an antioxidant, and the concentration of the whole solid components was adjusted to 40% in a toluene/hexane (mixture ratio: 2/1) solution to obtain a patch using Rubber-based pressure sensitive adhesive.

Preparation Example of Patch 38 Using Urethane-Based Pressure Sensitive Adhesive In the same manner as in Preparation example of the patches using the above-mentioned acrylic-based pressure sensitive adhesive except that Acrylic-based pressure sensitive adhesive A was changed to Urethane-based pressure sensitive adhesive prepared in Pressure sensitive adhesive preparation example 13, and a polyisocyanate (COLONATE L, NIPPON POLYURETHANE INDUSTRY CO., LTD.) (1.7% based on the whole solid components) was added as a curing agent to obtain a patch using Urethane-based pressure sensitive adhesive.

Concrete prescriptions of the patches prepared in the above-mentioned patch preparation examples are shown in the following table.

TABLE 1

| | Patch No. | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| Drug | Compound of Preparation example 44 | 5 | 5 | 5 | 5 | 5 | 5 | 5 | 5 | 5 | 10 | 10 | 10 | 10 | 10 | 10 | 10 | 10 | 30 | 30 |

TABLE 1-continued

| | | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| Adhesive agent | Acrylic-based pressure sensitive adhesive A | 95 | | | | | | | | | 90 | | | | | | | 70 | |
| | Acrylic-based pressure sensitive adhesive B | | 95 | | | | | | | | | 90 | | | | | | | 70 |
| | Acrylic-based pressure sensitive adhesive C | | | 95 | | | | | | | | | 90 | | | | | | |
| | Acrylic-based pressure sensitive adhesive D | | | | 95 | | | | | | | | | 90 | | | | | |
| | Acrylic-based pressure sensitive adhesive E | | | | | 95 | | | | | | | | | 90 | | | | |
| | Acrylic-based pressure sensitive adhesive F | | | | | | 95 | | | | | | | | | 90 | | | |
| | Acrylic-based pressure sensitive adhesive G | | | | | | | 95 | | | | | | | | | 90 | | |
| | Acrylic-based pressure sensitive adhesive H | | | | | | | | 95 | | | | | | | | | 90 | |
| | Acrylic-based pressure sensitive adhesive I | | | | | | | | | 95 | | | | | | | | | |
| | Silicone-based pressure sensitive adhesive | | | | | | | | | | | | | | | | | | |
| | Rubber-based pressure sensitive adhesive A | | | | | | | | | | | | | | | | | | |
| | Rubber-based pressure sensitive adhesive B | | | | | | | | | | | | | | | | | | |
| | Urethane-based pressure sensitive adhesive | | | | | | | | | | | | | | | | | | |
| Antioxidant | | | | | | | | | | | | | | | | | | | |
| Curing agent | | | | | | | | | | | | | | | | | | | |
| Thickness of pressure sensitive adhesive layer | (μm) | 70 | 70 | 70 | 70 | 70 | 70 | 70 | 70 | 70 | 70 | 70 | 70 | 70 | 70 | 70 | 70 | 70 | 70 |

| | Patch No. | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|---|
| Drug | Compound of Preparation example 44 | 30 | 30 | 30 | 30 | 30 | 30 | 50 | 50 | 50 | 50 | 50 | 50 | 50 | 50 | 5 | 10 | 10 | 10 | 10 |
| Adhesive agent | Acrylic-based pressure sensitive adhesive A | | | | | | | 50 | | | | | | | | | | | | |
| | Acrylic-based pressure sensitive adhesive B | | | | | | | | 50 | | | | | | | | | | | |
| | Acrylic-based pressure sensitive adhesive C | 70 | | | | | | | | 50 | | | | | | | | | | |
| | Acrylic-based pressure sensitive adhesive D | | 70 | | | | | | | | 50 | | | | | | | | | |
| | Acrylic-based pressure sensitive adhesive E | | | 70 | | | | | | | | 50 | | | | | | | | |

TABLE 1-continued

| | | C1 | C2 | C3 | C4 | C5 | C6 | C7 | C8 | C9 | C10 | C11 | C12 | C13 | C14 | C15 | C16 | C17 | C18 |
|---|---|---|---|---|---|---|---|---|---|---|---|---|---|---|---|---|---|---|---|
| | Acrylic-based pressure sensitive adhesive F | | | 70 | | | | | 50 | | | | | | | | | | |
| | Acrylic-based pressure sensitive adhesive G | | | | 70 | | | | | 50 | | | | | | | | | |
| | Acrylic-based pressure sensitive adhesive H | | | | | 70 | | | | | 50 | | | | | | | | |
| | Acrylic-based pressure sensitive adhesive I | | | | | | | | | | | | | | | | | | |
| | Silicone-based pressure sensitive adhesive | | | | | | | | | | | | | | 95 | 90 | | | |
| | Rubber-based pressure sensitive adhesive A | | | | | | | | | | | | | | | | 89 | | |
| | Rubber-based pressure sensitive adhesive B | | | | | | | | | | | | | | | | | 89 | |
| | Urethane-based pressure sensitive adhesive | | | | | | | | | | | | | | | | | | 88.3 |
| Antioxidant | BHT | | | | | | | | | | | | | | 1 | 1 | | | |
| Curing agent | Polyisocyanate | | | | | | | | | | | | | | | | | | 1.7 |
| Thickness of pressure sensitive adhesive layer | (μm) | 70 | 70 | 70 | 70 | 70 | 70 | 70 | 70 | 70 | 70 | 70 | 70 | 70 | 70 | 70 | 70 | 70 | 70 |

4. Antifungal Activity Test Against Dermatophytes

Measurement of the anti-*trichophyton* activity of the compound of the formula (I) comprised in the patch of the present invention was carried out by the following method. The compound to be evaluated was used by dissolving in dimethyl sulfoxide (DMSO). As a medium for the test, RPMI1640 medium containing 0.165M of 3-morpholino-propanesulfonic acid (MOPS) was used. As fungi to be tested, *Trichophyton mentagrophytes* (*T. mentagrophytes*) ATCC18748 or *Trichophyton rubrum* (*T. rubrum*) ATCC10218 was used. The testing fungal strain was apportioned to 100 μl with a concentration of $1 \times 10^4$ conidia/ml, mixed with a compound to be evaluated on a 96-well half area plate so that the DMSO concentration became 1%, and cultured at a cultivation temperature of 28° C. for 3 days (*Trichophyton mentagrophytes*) or 4 days (*Trichophyton rubrum*). Thereafter, 5 μl of Cell Counting Kit 8 (WST8) was added thereto, and absorbances at 450 nm and 595 nm were measured to use these as background values. Thereafter, these were cultivated at 28° C. for 5 hours (*Trichophyton mentagrophytes*) or overnight (*Trichophyton rubrum*) to cause a color, and absorbances at 450 nm and 595 nm were measured again. A growth inhibiting rate was calculated from the difference to the background values, and a 80% growth inhibiting concentration was made an MIC value (μg/ml).

TABLE 2

| Preparation example No. | MIC (*T. mentagrophytes*) | MIC (*T. rubrum*) |
|---|---|---|
| 1 | B | B |
| 5 | C | D |
| 6 | C | E |
| 7 | C | E |
| 8 | C | E |
| 9 | A | A |
| 10 | D | E |
| 11 | C | D |
| 12 | C | E |
| 13 | A | B |
| 14 | B | B |
| 15 | C | C |
| 16 | C | E |
| 17 | A | A |
| 18 | B | B |
| 19 | C | C |
| 20 | C | D |
| 21 | A | B |
| 22 | C | D |
| 23 | C | D |
| 24 | A | C |
| 25 | B | B |
| 26 | A | A |
| 28 | B | C |
| 30 | A | A |
| 31 | B | B |
| 32 | B | B |
| 33 | B | A |
| 34 | B | B |
| 35 | C | C |
| 36 | E | D |
| 37 | B | B |
| 38 | C | B |
| 39 | C | C |
| 40 | E | D |
| 41 | D | D |
| 42 | C | D |
| 43 | E | D |
| 44 | A | A |
| 45 | A | A |
| 46 | E | D |
| 47 | B | B |
| 48 | B | B |
| 49 | E | D |
| 50 | B | B |
| 51 | E | D |
| 52 | A | A |
| 53 | B | B |
| 54 | A | A |

TABLE 2-continued

| Preparation example No. | MIC (T. mentagrophytes) | MIC (T. rubrum) |
|---|---|---|
| 55 | A | A |
| 56 | A | A |
| 57 | B | B |
| 58 | B | A |
| 59 | B | B |
| 61 | C | C |
| 63 | A | A |
| Amorolfine hydrochloride | A | A |
| Terbinafine hydrochloride | A | A |

MIC
(T. mentagrophytes)
A ≤1 μg/ml
B 2 to 8 μg/ml
C 16 to 32 μg/ml
D Inhibited 50% or more and less than 80% with 32 μg/ml
E Inhibited less than 50% with 32 μg/ml
MIC
(T. rubrum)
A ≤2 μg/ml
B 4-16 μg/ml
C 16-32 μg/ml
D >32-64 μg/ml
E >64 μg/ml 5. Nail Permeability Test Method By using the same method as in Patch Preparation examples 1 to 33, the patches of the present invention with the formulations shown in the following Table in which the compound of Preparation example 44 had been used were prepared, and permeability of said compound to human nail was evaluated.

To the center of a human nail formed to a round shape having a diameter of 9 mm was adhered a patch formed to a round shape having a diameter of 4 mm, and after covering the patch with a cover tape*[1], it was placed on a receiver layer*[2], and allowed to stand under the atmosphere at a temperature of 32° C. and a relative humidity of 85% for one week. On the second day and fifth day from allowing to stand, 30 μl of a 20% aqueous polyethylene glycol solution was added to the receiver layer.

The patch and the cover tape were removed from the human nail which had been allowed to stand for one week. The human nail was dissolved in an aqueous sodium hydroxide solution, the compound of Preparation example 44 was extracted and quantitated by high performance liquid chromatography, which was made a nail storage amount. The nail storage amount was converted to an amount of the compound per 1 g weight of the respective nails which had previously measured, and an average value of the three specimens was calculated.

Also, said compound in the receiver layer was extracted with methanol, and quantitated by high performance liquid chromatography, which was made a nail permeated amount. The nail permeated amount was converted to an amount of the compound per 1 $cm^2$, and an average value of the three specimens was calculated.

*[1]: It was prepared by forming a tape in which an acrylic-based pressure sensitive adhesive had been applied on a PET film having a thickness of 12 μm to a round shape which has a diameter of 6.5 mm, and adhering a PET film having a thickness of 12 μm formed to a round shape which has a diameter of 4.5 mm to the center of the pressure sensitive adhesive surface.

*[2]: An absorbent cotton formed to a round shape with the same size as that of the human nail, to which 30 μl of a 20% aqueous polyethylene glycol solution had been added.

Results

As shown in the following Table, it could be confirmed that the compound was transferred into the nail with a sufficient amount in all the patches.

TABLE 3

| | Formulation (% by mass) | | | | | |
|---|---|---|---|---|---|---|
| | Test Example 1 | Test Example 2 | Test Example 3 | Test Example 4 | Test Example 5 | Test Example 6 |
| Compound of Preparation example 44 | 5 | 10 | 10 | 10 | 20 | 20 |
| Acrylic-based pressure sensitive adhesive D | — | 90 | 70 | — | 53.3 | — |
| Acrylic-based pressure sensitive adhesive H | 63.3 | — | — | 46.7 | — | 46.7 |
| Acrylic-based pressure sensitive adhesive I | 31.7 | — | — | 23.3 | 26.7 | 23.3 |
| N-acetyl cysteine | — | — | 10 | 10 | — | 10 |
| Aminoalkyl methacrylate copolymer E | — | — | 10 | 10 | — | — |
| Nail storage amount (μg/g) | 427 | 466 | 837 | 593 | 1080 | 1204 |
| Nail permeated amount (μg/$cm^2$) | 2.6 | 4.0 | 4.0 | 3.5 | 4.2 | 7.0 |

6. Antimicrobial Activity Test of Patches
Method

By using the same method as in Patch Preparation examples 1 to 38, the patches of the present invention with the formulation shown in the following Table in which the compound of Preparation example 44 had been used were prepared, and antimicrobial activity of the patch to the human nail was confirmed.

To the center of a human nail formed to a round shape having a diameter of 6 mm was adhered a patch formed to a round shape having a diameter of 3 mm, and after covering the patch with a cover tape*[1], it was placed on a receiver layer*[2], and allowed to stand under the atmosphere at a temperature of 32° C. and a relative humidity of 85% for one week. At the second day and fifth day after allowed to stand, 30 μl of a 20% aqueous polyethylene glycol solution was added to the receiver layer. The patch was removed from the human nail which had been allowed to stand for one week, and the cover tape was changed, then, the human nail was placed at the center of the test medium*[3], and cultivated under the atmosphere at a temperature of 28° C. for one week. For evaluation, the medium at the human nail and peripheral thereof were observed, and lengths of the inhibition zone were measured*[4].

*1: It was prepared by forming a tape in which a pressure sensitive adhesive had been applied on a PET film having a thickness of 12 μm to a round shape which has a diameter of 6.5 mm, and adhering a PET film having a thickness of 12 μm formed to a round shape which has a diameter of 4.5 mm to the center of the pressure sensitive adhesive surface.

*2: An absorbent cotton formed to a round shape with the same size as that of the human nail, to which 30 μl of a 20% aqueous polyethylene glycol solution had been added.

*3: On the surface of the Sabouraud's agar plating medium (available from Japan Becton Dickinson and Company), 50 μl of a suspension containing $1 \times 10^7$/mL of conidium of trichophyton (Trichophyton mentagrophytes (T. mentagrophytes) NBRC 32410) was uniformly coated.

*4: The length of the inhibition zone was obtained by measuring a transparent portion around the human nail in which growth of trichophyton had been inhibited, and calculating an average value of three specimens.

Results

In all the human nails to which the patch comprising the compound of Preparation example 44, inhibition zones in which growth of trichophyton was inhibited were formed, whereby it could be shown that a sufficient amount of the compound which is sufficient for showing antimicrobial activity had been transferred from the patch to the nail and stored. On the other hand, in the nail to which the patch (placebo patch) comprising no compound of Preparation example 44 was adhered, and in the nail to which no patch was adhered, no inhibition zone was formed.

TABLE 4

|  | Formulation (% by mass) | | | | | | |
| --- | --- | --- | --- | --- | --- | --- | --- |
|  | Test Example 7 | Test Example 8 | Test Example 9 | Test Example 10 | Test Example 11 | Test Example 12 | Test Example 13 |
| Compound of Preparation example 44 | 10 | 10 | 10 | 10 | 10 | 10 | 10 |
| Acrylic-based pressure sensitive adhesive D | 90 | — | 75 | — | — | — | — |
| Acrylic-based pressure sensitive adhesive E | — | 90 | — | — | — | — | — |
| Acrylic-based pressure sensitive adhesive I | — | — | 15 | — | — | — | — |
| Silicone-based pressure-sensitive adhesive | — | — | — | 90 | — | — | — |
| Rubber-based pressure-sensitive adhesive A | — | — | — | — | 90 | — | — |
| Rubber-based pressure-sensitive adhesive B | — | — | — | — | — | 90 | — |
| Urethane-based pressure-sensitive adhesive | — | — | — | — | — | — | 90 |
| Inhibition zone (mm) | 6.9 | 6.1 | 5.5 | 4.9 | 10.7 | 8.1 | 2.2 |

7. Adhesiveness Test of Patch
Method

By using the same method as in Patch Preparation examples 1 to 13, the patches comprising the compound of Preparation example 44 were prepared with the formulation shown in the following Table, and their adhesive forces and adhesivenesses were measured by the method regulated in Japanese Industrial Standard JIS Z0237. More specifically, a patch with a width of 10 mm was adhered to a stainless test plate with a surface finish of BA, and an adhesive force thereof when it is peeled off by an Instron type tensile tester with a peeling angle of 180° was measured. Based on the measurement of this adhesive force, evaluation was carried out according to the following criteria.

I: Adhesive force is 2.0N/10 mm or more
II: Adhesive force is 0.1N/10 mm or more
III: Adhesive force is less than 0.1N/10 mm Also, a patch test piece cut to a size of 10 mm×10 mm was adhered to each toenail of four subjects, and the adhered conditions for 7 days were evaluated by whether it is adhered (good), or dropped out.

Results

As shown in the following Table, adhesive forces sufficient as the patch were shown in all the patches. Also, these were adhered for a long term of 7 days without dropping out, whereby these were practically excellent in adhesiveness.

TABLE 5

| | Formulation (% by mass) | | | | | | |
|---|---|---|---|---|---|---|---|
| | Test Example 14 | Test Example 15 | Test Example 16 | Test Example 17 | Test Example 18 | Test Example 19 | Test Example 20 |
| Compound of Preparation example 44 | 10 | 10 | 10 | 10 | 15 | 20 | 20 |
| Acrylic-based pressure sensitive adhesive D | 85 | 75 | 60 | 45 | 46.7 | 53.3 | 46.7 |
| Acrylic-based pressure sensitive adhesive I | 5 | 15 | 30 | 25 | 23.3 | 26.7 | 23.3 |
| N-acetyl cysteine | — | — | — | 10 | 10 | — | 10 |
| Aminoalkyl methacrylate copolymer E | — | — | — | 10 | 5 | — | — |
| Adhesive force | I | I | I | I | I | I | I |
| Nail Adhesiveness | Good | Good | Good | Good | Good | Good | Good |

INDUSTRIAL APPLICABILITY

According to the present invention, a patch for nail and/or skin having antifungal activity against dermatophytes, and having higher nail permeability can be provided.

The invention claimed is:

1. A patch for a nail for treating dermatophytosis which comprises a pressure sensitive adhesive layer comprising an acrylic-based pressure-sensitive adhesive and 2-(3, 5-dimethyl-1H-pyrazol-1-yl)-5-methylphenol or a salt thereof, wherein the acrylic-based pressure sensitive adhesive consists of a copolymer consisting of 2-ethylhexyl acrylate and N-vinylpyrrolidone, and wherein a mass ratio of the 2-ethylhexyl acrylate to the N-vinylpyrrolidone is 70:30 to 90:10.

2. The patch for a nail according to claim 1, wherein the 2-(3, 5-dimethyl-1H-pyrazol-1-yl)-5-methylphenol or a salt thereof is contained in an amount of 5 to 30% by mass based on the total mass of the pressure sensitive adhesive layer.

3. The patch for a nail according to claim 1, wherein the 2-(3, 5-dimethyl-1H-pyrazol-1-yl)-5-methylphenol or a salt thereof is contained in an amount of 5 to 20% by mass based on the total mass of the pressure sensitive adhesive layer.

4. The patch for nail according to claim 1, wherein 2-(3, 5-dimethyl-1H-pyrazol-1-yl)-5-methylphenol or a salt thereof is contained in an amount of 5 to 15% by mass based on the total mass of the pressure sensitive adhesive layer.

5. The patch for a nail according to claim 1, wherein the dermatophytosis is caused by tinea unguium.

6. The patch for a nail according to claim 1, wherein the nail is a human nail.

7. The patch for a nail according to claim 1, wherein the pressure-sensitive adhesive layer has a thickness of 20 to 200 μm.

8. A method for treating dermatophytosis in a patient in need thereof comprising applying the patch according to claim 1 to a nail of the patient.

9. The method according to claim 8, wherein the nail is a human nail.

10. The method according to claim 8, wherein the dermatophytosis is caused by tinea unguium.

* * * * *